United States Patent
Ding et al.

(10) Patent No.: US 7,851,626 B2
(45) Date of Patent: Dec. 14, 2010

(54) 4,4,5,5, TETRASUBSTITUTED IMIDAZOLINES

(75) Inventors: Qingjie Ding, Bridgewater, NJ (US); Bradford James Graves, Nutley, NJ (US); Norman Kong, West Caldwell, NJ (US); Jin-Jun Liu, Warren Township, NJ (US); Allen John Lovey, North Caldwell, NJ (US); Giacomo Pizzolato, Glen Ridge, NJ (US); John Lawson Roberts, Budd Lake, NJ (US); Sung-Sau So, Nutley, NJ (US); Binh Thanh Vu, North Caldwell, NJ (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 933 days.

(21) Appl. No.: 11/604,558

(22) Filed: Nov. 27, 2006

(65) Prior Publication Data

US 2007/0129416 A1 Jun. 7, 2007

Related U.S. Application Data

(60) Provisional application No. 60/852,747, filed on Oct. 19, 2006, provisional application No. 60/741,223, filed on Dec. 1, 2005.

(51) Int. Cl.
C07D 403/02 (2006.01)
C07D 233/06 (2006.01)
A61K 31/497 (2006.01)
A01N 43/50 (2006.01)

(52) U.S. Cl. ............... 544/370; 548/354.1; 514/254.05; 514/385

(58) Field of Classification Search ................. 544/370; 548/354.1; 514/254.05, 385
See application file for complete search history.

(56) References Cited

U.S. PATENT DOCUMENTS

| 6,617,346 | B1 | 9/2003 | Kong et al. |
| 6,734,302 | B2 | 5/2004 | Kong et al. |
| 2004/0259867 | A1 | 12/2004 | Fotouhi et al. |
| 2004/0259884 | A1 | 12/2004 | Haley et al. |
| 2005/0282803 | A1 | 12/2005 | Haley et al. |
| 2005/0288287 | A1 | 12/2005 | Fotouhi et al. |

FOREIGN PATENT DOCUMENTS

| WO | WO 00/78725 | 12/2000 |
| WO | WO 03/101969 | 12/2003 |
| WO | WO 2005/002575 | 1/2005 |
| WO | WO 2005/110996 | * 11/2005 |

OTHER PUBLICATIONS

CAPLUS Abstract of Frandsen et al., Acta Chemica Scandinavica (1991), 45(6), 627-31.*
Wells et al. *J. Org. Chem.*, 1972, 37, 2158-2161.
Hunter et al., *Can. J. Chem.*, 1972, vol. 50, pp. 669-677.
McCapra et al. *Photochem. and Photobiol.* 1965, 4, 1111-1121.
Zupanc et al. *Bull. Soc. Chem. & Tech.* (Yugoslavia) 1980-81, 27/28, 71-80.
H. Ansel et al., Pharmaceutical Dosage Forms and Drug Delivery Systems (6th Ed. 1995) at pp. 108-109.
Krogsgaard-Larsen, et al., Textbook of Drug Design and Development (2d Ed. 1996) at pp. 152-191.
H. Ansel et al., Pharmaceutical Dosage Forms and Drug Delivery Systems (6th Ed. 1995) at pp. 196 and 1456-1457.
Vassilev, L. et al. *Science* 2004, 303, 844-848.
B. Bracke, et al, Bulletin des Societes Chimiques Belges, 1990, 99, 797-801.
S. V. Pansare, A. N. Rai, S. N. Kate, Synlett, 1998, 623-624.

* cited by examiner

*Primary Examiner*—Robert Havlin
(74) *Attorney, Agent, or Firm*—George W. Johnston; Patricia S. Rocha-Tramaloni

(57) ABSTRACT

There is provided a compound of formula I

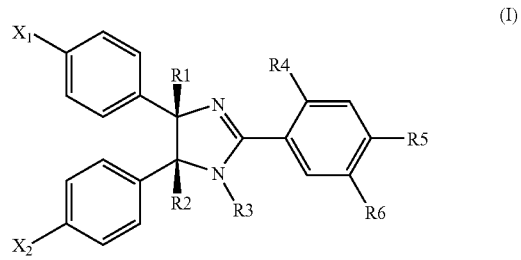

and the pharmaceutically acceptable salts and esters thereof wherein $X_1$, $X_2$, $R^1$, $R^2$, $R^3$, $R^4$, $R^5$ and $R^6$ are herein described.

The compounds exhibit activity as anticancer agents.

33 Claims, No Drawings

4,4,5,5, TETRASUBSTITUTED IMIDAZOLINES

PRIORITY TO RELATED APPLICATIONS

This application claims the benefit of U.S. Provisional Application No. 60/741,223, filed Dec. 1, 2005 and U.S. Provisional Application No. 60/852,747, filed Oct. 19, 2006. The entire contents of the above-identified applications are hereby incorporated by reference.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

Wells et al. *J. Org. Chem.* 1972, 37, 2158-2161, report synthesis of imidazolines. Hunter et al. *Can. J. Chem.* 1972, 50, 669-77, report the preparation of amarine and isoamarine compounds which had previously been studied for chemiluminescence (McCapra et al. *Photochem. and Photobiol.* 1965, 4, 1111-1121). Zupanc et al. *Bull. Soc. Chem. & Tech.* (Yugoslavia) 1980-81, 27/28, 71-80, report the use of triaryl imidazolines as starting materials in the preparation of EDTA derivatives.

EP 363 061 to Matsumoto reports imidazoline derivatives useful as immunomodulators. The compounds were indicated to have low toxicity. Treatment and/or prevention of rheumatoid arthritis, multiple sclerosis, systemic lupus, erythemathodes, and rheumatic fever were implicated. WO 00/78725 to Choueiry et al. report a method for making substituted amidine compounds, and indicate that imidazoline-type compounds may be useful in the treatment of diabetes or related diseases involving impaired glucose disposal.

U.S. Pat. No. 6,617,346 B1 (issued Sep. 9, 2003), U.S. Pat. No. 6,734,302 B2 (issued May 11, 2004), US20040259884A1 (published Dec. 23, 2004), US20040259867A1 (published Dec. 23, 2004), US20050282803A1 (published Dec. 22, 2005) and US20050288287A1 (published Dec. 29, 2005) disclose related cis-imidazolines.

SUMMARY OF THE INVENTION

The present invention provides at least one compound of formula I

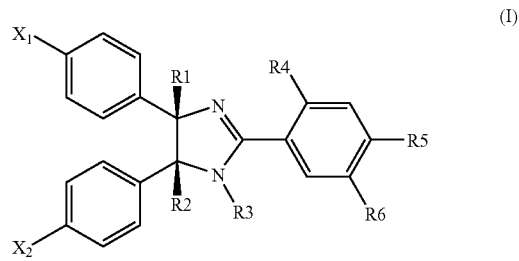

and the pharmaceutically acceptable salts and esters thereof wherein $X_1$, $X_2$, $R^1$, $R^2$, $R^3$, $R^4$, $R^5$ and $R^6$ are herein described.

DETAILED DESCRIPTION OF THE INVENTION

The present invention provides chiral cis-imidazolines which are small molecule inhibitors of the MDM2-p53 interaction. In cell-free and cell-based assays, compounds of the present invention are shown to inhibit the interaction of MDM2 protein with a p53-like peptide with a potency that is approximately 100 fold greater than a p53-derived peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations.

Therefore, the activity of MDM2 antagonists is likely linked to its mechanism of action. These compounds can be potent and selective anticancer agents.

The present invention provides at least one compound of formula I

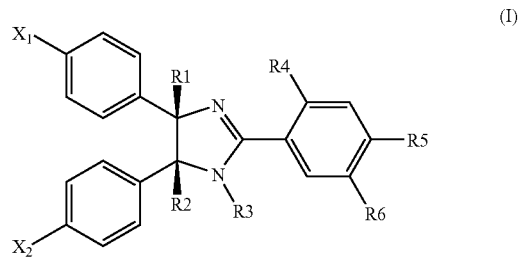

wherein $X_1$ and $X_2$ are halogen, acetylene, cyano, trifluoromethyl or nitro;

$R^1$ and $R^2$ are selected from the group consisting of H, $CH_3$, $CH_2CH_3$, $CH_2OH$ and $CH_2OCH_3$ with the proviso that $R^1$ and $R^2$ are not both hydrogen;

$R^3$ is H or —C(=O)—$R^7$;

and where $R^6$ is hydrogen then $R^4$ is —$OCH_3$, —$OCH_2CH_3$, —$OCH_2CH_2F$, —$OCH_2CH_2OCH_3$, or —$OCH(CH_3)_2$;

$R^5$ is

—H

-halogen,

—$CH_3$,

—$CF_3$,

—$OCH_3$,

—$C(CH_3)_2$,

-cyclopropyl,

-cyano,

—$C(CH_3)_3$,

—$C(CH_3)_2$OR (where R is H, $CH_3$ or $CH_2CH_3$),

—$C(CH_3)_2$CH—OR (where R is H, $CH_3$, $CH(CH_3)_2$, $CH_2CH_2OH$ or $CH_2CH_2OCH_3$),

—$C(CH_3)_2$CN,

—$C(CH_3)_2$COR (where R is $CH_3$),

—$C(CH_3)_2$COOR (where R is H, $CH_3$, $CH_2CH_3$ or CH$(CH_3)_2$),

—$C(CH_3)_2$CONR$^a$R$^b$ (where R$^a$ is H or $CH_3$ and R$^b$=H or $CH_3$),

—SR (where R is $CH_3$ or $CH_2CH_3$), or

—$SO_2$R (where R is $CH_3$, $CH_2CH_3$, 1-pyrrolidine, NH-tert-butyl or $N(CH_3)_2$);

and where $R^6$ is not hydrogen then $R^4$ is —$OCH_3$, —$OCH_2CH_3$, —$OCH_2CH_2F$, —$OCH_2CH_2OCH_3$, or —$OCH(CH_3)_2$;

$R^5$ is hydrogen, —Cl, —$OCH_3$, tert-butyl or —$N(CH_3)_2$;

$R^6$ is —Cl, cyclopropyl, —$SO_2$R (where R is $CH_3$, $CH_2CH_3$, 1-pyrrolidine, NH-tert-butyl, $NH_2$, or $N(CH_3)_2$);

and $R^7$ is selected from the group consisting of

—$CH_3$, —$CH(CH_3)_2$, —$CH_2CH(CH_3)_2$, cyclopropyl, cyclobutyl, —$CH_2CH_2Ph$, 2-furanyl, phenyl, or phenyl substituted by chloro, $OCH_3$ or cyano, 4-morpholinyl, 1-piperidinyl, 4-thiomorpholinyl, or 4-thiomorpholinyl-1,1-dioxide, —NR$^c_2$ (wherein R$^c$ is hydrogen, —$CH_3$, —$CH_2CH_3$, —$CH_2CH_2OH$, —$CH_2CH_2OCH_3$, or —$CH_2CH(OH)CH_2OH$), a substituted piperazine of the formula

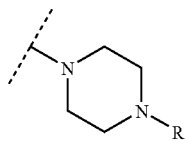

wherein R is selected from the group consisting of hydrogen, lower alkyl, $CH(CH_3)_2$,d) $CH(CH_2CH_3)_2$, cyclopentyl,

—$CH_2CH(OH)CH_3$,

—$CH_2CF_3$,

—$CH_2CH(OH)CF_3$,

—$CH_2C(CH_3)_2OH$,

—$CH_2$-[4-N-methylpiperidinyl],

—$CH_2CH_2R^d$ (wherein R$^d$ is —OH, —$OCH_3$, —$OCH_2CH_2OH$, —$OCH_2CH_2OCH_3$, —CN, —$CF_3$, —$SO_2CH_3$, —$SO_2NH_2$, —$SO_2N(CH_3)_2$, —$CONH_2$, —$CON(CH_3)_2$, —$NH_2$, —$NHCOCH_3$, —$NHSO_2CH_3$, —$N(CH_3)_2$, —$N(CH_2CH_3)_2$, —$N(CH_2CH_2CH_3)_2$, 1-pyrrolidinyl, 1-piperidinyl, 4-morpholinyl, 2-isothiazolidinyl-1,1-dioxide, or 2-tetrahydrofuranyl), l) —$CH_2CH_2CH_2R^e$ (wherein R$^e$ is —OH, —$OCH_3$, —$SO_2CH_3$, —$SO_2CH_2CH_3$, —$SO_2N(CH_3)_2$, —CN, —$N(CH_3)_2$, —$N(CH_2CH_2CH_3)_2$, 1-imidazoyl, 1-pyrrolidinyl, 1-piperidinyl, 4-morpholinyl, —$COOCH_3$, —$COOCH_2CH_3$, —$COOC(CH_3)_3$, —$CON(CH_3)_2$, —CO—R$^f$ (wherein R$^f$ is $CH_3$, $CH_2CH_3$, cyclopropyl, phenyl, 2-thienyl, 3-thienyl, 2-furanyl, 3-furanyl), —$COCH_2$—R$^g$ (wherein R$^g$ is H, —$NHCH_2CH_2OH$, —$NHCH_2CH_2OCH_3$, —$NHCH_2CH_2N(CH_3)_2$, 1-piperidinyl, 1-(piperidinyl-4-methanol), 4-morpholinyl, or —$N(CH_3)$-(3-(1-methylpyrrolidinyl))), m) —$CH_2$—CO—R$^h$ (wherein R$^h$ is —$OCH_3$, $OCH_2CH_3$, —$NH_2$, —$NHCH_2CH(CH_3)_2$, —$NHCH_2CF_3$, —NH-cyclopropyl, —NH-tert-butyl, —$NHCH_2CH_2OH$, —N$(CH_3)_2$, —$N(CH_2CH_3)_2$, —$N(CH_2CH_2OH)_2$, —$N(CH_2CH_2OCH_3)_2$, —$N(CH_3)CH_2CH_2OH$, —$N(CH_3)CH_2CH_2OCH_3$, —$NHCH_2CH_2OCH_3$, 1-pyrrolidinyl, 1-piperidinyl, 1-(piperidinyl-4-methanol), 1-(piperidinyl-3-carboxamide), 4-morpholinyl, 4-thiomorpholinyl, 4-thiomorpholinyl-1,1-dioxide, 1-piperazinyl, 1-(4-acetylpiperazinyl), 1-(3-oxopiperazinyl), n) —$SO_2R^i$ (wherein R$^i$ is —$CH_3$, —$CH_2CH_3$, —$CH(CH_3)_2$, phenyl, 4-methylphenyl, 4-propylphenyl, $CF_3$, 2-thienyl, 3-thienyl, $NH_2$, $NHCH_3$, $N(CH_3)_2$, $NHCH_2CH_2OCH_3$, $N(CH_2CH_2OCH_3)_2$, 1-pyrrolidinyl, 1-piperidinyl, 4-morpholinyl, 1-piperazyl-4-ethanol, 1-(4-acetylpiperazinyl), 1-(3-oxopiperazinyl)), o) —COR$^j$ (wherein R$^j$ is —$CH_3$, —$CH_2CH_3$, —$CH(CH_3)_2$, 2-tetrahydrofuranyl, 2-thienyl, 3-thienyl, $NH_2$, $NHCH_3$, $N(CH_3)_2$, 1-pyrrolidinyl, 1-piperidinyl, 4-morpholinyl, 1-piperazinyl-4-ethanol, 1-(4-acetylpiperazinyl), or 1-(3-oxopiperazinyl)), p) 4-tetrahydro-2H-thiopyranyl-1,1-dioxide, q) 4-piperidinyl-1-acetyl, r) 4-piperidinyl-1-dimethylcarboxamide, and s) 3-tetrahydro-thiophenyl-1,1-dioxide;

v) a substituted oxopiperazine of the formula

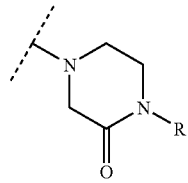

wherein R is H, —CH$_3$, —CH$_2$CH$_3$, —CH$_2$CH$_2$CH$_3$, —CH$_2$CH$_2$OH, or —CH$_2$CH$_2$OCH$_3$ and a substituted piperidine of the formula

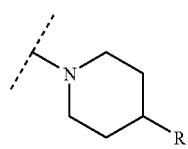

wherein R is H, COOCH$_3$, COOCH$_2$CH$_3$, CONH$_2$, —OH, CH$_2$OH, CH$_2$CH$_2$OH, CH$_2$—N(CH$_2$CH$_3$)$_2$, —CH$_2$-(1-piperazinyl), CH$_2$-(1-(3-oxopiperazinyl)), NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$-(1-piperidinecarboxamide), NHCOCH$_2$—(N, N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$, 1-pyrrolidinyl, 1-piperidinyl, 1-(4-methylpiperazinyl), or 4-morpholinyl;

and the pharmaceutically acceptable salts and esters thereof.

More preferred compounds are those wherein $X_1$ and $X_2$ are —Cl.

More preferred compounds are those wherein $R^3$ is —C(=O)—$R^7$.

More preferred compounds are those wherein $R^6$ is hydrogen; $R^4$ is —OCH$_3$, —OCH$_2$CH$_3$, or —OCH(CH$_3$)$_2$; and $R^5$ is —C(CH$_3$)$_3$, —C(CH$_3$)$_2$OR (where R is H or CH$_3$), —C(CH$_3$)$_2$CH—OR (where R is H or CH$_3$), —C(CH$_3$)$_2$CN, —C(CH$_3$)$_2$COR (where R is CH$_3$), —SO$_2$R (where R is CH$_3$, 1-pyrrolidine, NH-tert-butyl or N(CH$_3$)$_2$).

Also preferred compounds are those wherein $R^4$ is —OCH$_3$, —OCH$_2$CH$_3$, or —OCH(CH$_3$)$_2$; $R^5$ is —Cl; and $R^6$ is —SO$_2$R (where R is CH$_3$, 1-pyrrolidine, NH-tert-butyl, NH$_2$, or N(CH$_3$)$_2$).

More preferred compounds are those wherein $R^7$ is

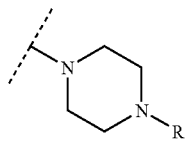

wherein R is —CH$_2$COR$^h$.

Yet more preferred compounds are those where R$^h$ is 4-morpholinyl, 1-pyrrolidinyl, 1-piperidinyl, NH$_2$, or N(CH$_3$)$_2$.

More preferred compounds are those wherein $R^7$ is

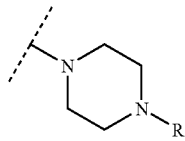

wherein R is —CH$_2$CH$_2$CH$_2$R$^e$.

Yet more preferred compounds are those wherein R$^e$ is —SO$_2$CH$_3$ or —SO$_2$CH$_2$CH$_3$.

More preferred compounds are those wherein $R^7$ is

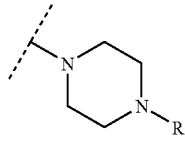

wherein R is —CH$_2$CH$_2$R$^d$.

Yet more preferred compounds are those wherein R$^d$ is —SO$_2$CH$_3$, —NHSO$_2$CH$_3$, —NHCOCH$_3$, or CF$_3$.

More preferred compounds are those wherein $R^7$ is

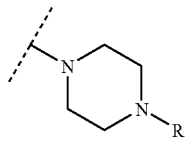

wherein R is 4-tetrahydro-2H-thiopyranyl-1,1-dioxide.

Especially preferred compounds are from the group consisting of:

rac-(4S*,5R*)-4,5-Bis(4-chlorophenyl)-2-(4-(tert-butyl)-2-ethoxy-phenyl)-4,5-dimethyl-4,5-dihydro-1H-imidazole, (4S,5R)-4,5-Bis(4-chlorophenyl)-2-(4-(tert-butyl)-2-ethoxy-phenyl)-4,5-dimethyl-4,5-dihydro-1H-imidazole-1-carbonyl chloride, (4S,5R)-4-[[4-[[4,5-Bis(4-chlorophenyl)-2-[4-(tert-butyl)-2-ethoxy-phenyl]-4,5-dimethyl-4,5-dihydro-1H-imidazol-1-yl]carbonyl]-1-piperazinyl]acetyl]-morpholine, (4S,5R)-4-[[4-[[4,5-bis(4-chlorophenyl)-2-[4-(tert-butyl)-2-ethoxy-phenyl]-4,5-dimethyl-4,5-dihydro-1H-imidazol-1-yl]carbonyl]-1-piperidine, (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine, (4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3,3,3-trifluoropropyl]-piperazine, 2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-acetamide, 2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-1-pyrrolidin-1-yl-ethanone, N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-acetamide, N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-methanesulfonamide,

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(2-hydroxy-ethyl)-piperazin-1-yl]-methanone, (S)-4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-1-methyl-piperazine-2-carboxylic acid methyl ester, 5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-2-tert-butyl-4-ethoxy-N,N-dimethyl-benzenesulfonamide, rac-2-{4-[(4S*,5R*)-4,5-Bis-(4-chloro-phenyl)-4,5-dimethyl-4,5-dihydro-1H-imidazol-2-yl]-3-ethoxy-phenyl}-2-methyl-propionitrile, 2-(4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-2-methyl-propionitrile, N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-methanesulfonamide, N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-acetamide, 2-(4-{(4S,5R)-4,5-Bis-(4-chloro-phenyl)-1-[4-(2-hydroxy-ethyl)-piperazine-1-carbonyl]-4,5-dimethyl-4,5-dihydro-1H-imidazol-2-yl}-3-ethoxy-phenyl)-2-methyl-propionitrile, 2-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-2-methyl-propionitrile, 2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-acetamide, 2-[4-((4S,5R)-4,5-Bis-(4-chloro-phenyl)-1-{4-[2-(1,1-dioxo-isothiazolidine-2-yl)-ethyl]-piperazine-1-carbonyl}-4,5-dimethyl-4,5-dihydro-1H-imidazol-2-yl)-3-ethoxy-phenyl]-2-methyl-propionitrile, 2-(4-{(4S,5R)-4,5-Bis-(4-chloro-phenyl)-4,5-dimethyl-1-[4-(2-oxo-2-pyrrolidin-1-yl-ethyl)-piperazine-1-carbonyl]-4,5-dihydro-1H-imidazol-2-yl}-3-ethoxy-phenyl)-2-methyl-propionitrile, 2-{4-[(4S,5R)-1-[4-(1-Acetyl-piperidin-4-yl)-piperazine-1-carbonyl]-4,5-bis-(4-chloro-phenyl)-4,5-dimethyl-4,5-dihydro-1H-imidazol-2-yl]-3-ethoxy-phenyl}-2-methyl-propionitrile, 4-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-piperidine-1-carboxylic acid isopropylamide, rac-(4S*,5R*)-4,5-Bis-(4-chloro-phenyl)-2-[2-ethoxy-4-(pyrrolidine-1-sulfonyl)-phenyl]-4,5-dimethyl-4,5-dihydro-1H-imidazole, rac-(4S*,5R*)-4-[(4,5-Bis-(4-chloro-phenyl)-4,5-dimethyl-4,5-dihydro-1H-imidazol-2-yl]-N-tert-butyl-3-ethoxy-benzenesulfonamide, {(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(3-methanesulfonyl-propyl)-piperazin-1-yl]-methanone, 2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-acetamide, 2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-1-pyrrolidin-1-yl-ethanone, N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-methanesulfonamide, N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-acetamide, {(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(2-hydroxy-ethyl)-piperazin-1-yl]-methanone, 4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-3-ethoxy-benzenesulfonamide, 2-{4-[(4S,5R)-2-(4-tert-Butylsulfamoyl-2-ethoxy-phenyl)-4,5-bis-(4-chloro-phenyl)-4,5-dimethyl-4,5-dihydro-imidazole-1-carbonyl]-piperazin-1-yl}-acetamide, rac-(4S*,5R*)-5-[4,5-Bis-(4-chlorophenyl)-4,5-dimethyl-4,5-dihydro-1H-imidazol-2-yl]-N-tert-butyl-2-chloro-4-ethoxybenzenesulfonamide, 5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-2-chloro-4-ethoxy-benzenesulfonamide, 5-{(4S,5R)-4,5-Bis-(4-chlorophenyl)-1-[4-(2-methanesulfonylaminoethyl)piperazine-1-carbonyl]-4,5-dimethyl-4,5-dihydro-1H-imidazol-2-yl}-N-tert-butyl-2-chloro-4-ethoxybenzenesulfonamide, N-{(4S,5R)-(2-{4-[2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}ethyl)acetamide, 5-{(4S,5R)-4,5-Bis-(4-chlorophenyl)-1-[4-(2-hydroxyethyl)piperazine-1-carbonyl]-4,5-dimethyl-4,5-dihydro-1H-imidazol-2-yl}-N-tert-butyl-2-chloro-4-ethoxybenzenesulfonamide, 5-{(4S,5R)-4,5-Bis-(4-chlorophenyl)-4,5-dimethyl-1-[4-(2-oxo-2-pyrrolidin-1-yl-ethyl)-piperazine-1-carbonyl]-4,5-dihydro-1H-imidazol-2-yl}-N-tert-butyl-2-chloro-4-ethoxybenzenesulfonamide, 2-{4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}-acetamide, (S)-4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-1-methylpiperazine-2-carboxylic acid methyl ester, rac-(4S*,5R*)-2-[4-Chloro-2-ethoxy-5-(pyrrolidine-1-sulfonyl)phenyl]-4,5-bis-(4-chlorophenyl)-4,5-dimethyl-4,5-dihydro-1H-imidazole, 5-{(4S,5R)-2-[4-Chloro-2-ethoxy-5-(pyrrolidine-1-sulfonyl)phenyl]-4,5-bis-(4-chloro-phenyl)-4,5-dimethyl-4,5-dihydroimidazol-1-yl]-[4-(3-methanesulfonylpropyl)-piperazin-1-yl]methanone, rac-(4S*,5R*)-4,5-Bis-(4-chlorophenyl)-2-[2-ethoxy-4-methoxy-5-(pyrrolidine-1-sulfonyl)phenyl]-4,5-dimethyl-4,5-dihydro-1H-imidazole, {(4S,5R)-4,5-Bis-(4-chlorophenyl)-2-[2-ethoxy-4-methoxy-5-(pyrrolidine-1-sulfonyl)-phenyl]-4,5-dimethyl-4,5-dihydroimidazol-1-yl}-[4-(3-methanesulfonylpropyl)-piperazin-1-yl]methanone, rac-(4S*,5R*)-2-(4-Chloro-2-ethoxy-5-methanesulfonylphenyl)-4,5-bis-(4-chlorophenyl)-4,5-dimethyl-4,5-dihydro-1H-imidazole,

[(4S,5R)-2-(4-Chloro-2-ethoxy-5-methanesulfonyl-phenyl)-4,5-bis-(4-chlorophenyl)-4,5-dimethyl-4,5-dihydroimidazol-1-yl]-[4-(3-methanesulfonylpropyl)-piperazin-1-yl]methanone, rac-(4S*,5R*)-4,5-Bis-(4-chlorophenyl)-2-[2-ethoxy-5-(pyrrolidine-1-sulfonyl)phenyl]-4,5-dimethyl-4,5-dihydro-1H-imidazole, {(4S,5R)-4,5-Bis-(4-chlorophenyl)-2-[2-ethoxy-5-(pyrrolidine-1-sulfonyl)phenyl]-4,5-dimethyl-4,5-dihydroimidazol-1-yl}-[4-(3-methanesulfonylpropyl)-piperazin-1-yl]methanone, rac-4-[(4S*,5R*)-4,5-Bis-(4-chloro-phenyl)-4,5-dimethyl-4,5-dihydro-1H-imidazol-2-yl]-3-ethoxy-benzonitrile, 4-{(4S,5R)-4,5-Bis-(4-chlorophenyl)-1-[4-(3-methanesulfonylpropyl)-piperazine-1-carbonyl]-4,5-dimethyl-4,5-dihydro-1H-imidazol-2-yl}-3-ethoxybenzonitrile,

[(4S,5R)-2-(4-tert-Butyl-2-ethoxy-phenyl)-4,5-bis-(4-chloro-phenyl)-4,5-dimethyl-4,5-dihydro-imidazol-1-yl]-piperazin-1-yl-methanone, 1-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethanone, N-tert-Butyl-2-{4-[(4S,5R)-2-(4-tert-butyl-2-ethoxy-phenyl)-4,5-bis-(4-chloro-phenyl)-4,5-dimethyl-4,5-dihydro-imidazole-1-carbonyl]-piperazin-1-yl}-acetamide, rac-(4S*,5R*)-2-(4-Bromo-2-ethoxy-phenyl)-4,5-bis-(4-chloro-phenyl)-4,5-dimethyl-4,5-dihydro-1H-imidazole, rac-(4S*,5R*)-2-(4-Bromo-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone, rac-2-{4-[(4S*,5R*)-4,5-Bis-(4-chloro-phenyl)-4,5-dimethyl-4,5-dihydro-1H-imidazol-2-yl]-3-ethoxy-phenyl}-propan-2-ol,

[(4S,5R)-4,5-Bis-(4-chloro-phenyl)-2-(2-ethoxy-phenyl)-4,5-dimethyl-4,5-dihydro-imidazol-1-yl]-[4-(3-methanesulfonyl-propyl)-piperazin-1-yl]-methanone, 2-{4-[(4S,5R)-4,5-Bis-(4-chloro-phenyl)-2-(2-ethoxy-phenyl)-4,5-dimethyl-4,5-dihydro-imidazole-1-carbonyl]-piperazin-1-yl}-acetamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(3-methanesulfonyl-propyl)-piperazin-1-yl]-methanone, 2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-acetamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(2-hydroxy-ethyl)-piperazin-1-yl]-methanone, 2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-1-pyrrolidin-1-yl-ethanone, N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-acetamide, N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-methanesulfonamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone, rac-(4S*,5R*)-4,5-Bis-(4-chloro-phenyl)-2-(2-isopropoxy-4-methoxy-phenyl)-4,5-dimethyl-4,5-dihydro-1H-imidazole, rac-(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(3-methanesulfonyl-propyl)-piperazin-1-yl]-methanone, rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-acetamide, rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-1-morpholin-4-yl-ethanone, rac-4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-2-one, rac-[(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(2-methanesulfonyl-ethyl)-piperazin-1-yl]-methanone, rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-1H-imidazole, 2-(4-{(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl}-piperazin-1-yl)-acetamide, {rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(3-methanesulfonyl-propyl)-piperazin-1-yl]-methanone, {(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone, rac-1-[(4S*,5R*)-2-(4-tert-Butyl-2-ethoxy-phenyl)-4,5-bis-(4-chloro-phenyl)-4,5-dimethyl-4,5-dihydro-imidazol-1-yl]-ethanone, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-2-methyl-propan-1-one,

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclopropyl-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclobutyl-methanone, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-methyl-butan-1-one, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-phenyl-propan-1-one, 4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-benzonitrile,

[(4S,5R)-2-(4-tert-Butyl-2-ethoxy-phenyl)-4,5-bis-(4-chloro-phenyl)-4,5-dimethyl-4,5-dihydro-imidazol-1-yl]-furan-2-yl-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-phenyl-methanone, rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-methoxy-phenyl)-methanone, rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-chloro-phenyl)-methanone, rac-(4S*,5R*)-2-(4-tert-Butyl-5-chloro-2-ethoxy-phenyl)-4,5-bis-(4-chloro-phenyl)-4,5-dimethyl-4,5-dihydro-1H-imidazole,

[(4S,5R)-2-(4-tert-Butyl-5-chloro-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone, 2-{4-[(4S,5R)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-acetamide, rac-(2-{4-[4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-1-morpholin-4-yl-ethanone, rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-dimethylamino-piperidin-1-yl)-methanone, rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-pyrrolidin-1-yl-piperidin-1-yl)-methanone, rac-[1,4']Bipiperidinyl-1'-yl-[(4S*,5R*)-2-(4-tert-butyl-5-chloro-2-ethoxy-phenyl)-4,5-bis-(4-chloro-phenyl)-4,5-dimethyl-4,5-dihydro-imidazol-1-yl]-methanone, rac-{1-[(4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperidin-4-yl}-carbamic acid tert-butyl ester, rac-(4S*,5R*)-4,5-Bis-(4-chloro-phenyl)-2-(2-ethoxy-4-trifluoromethyl-phenyl)-4,5-dimethyl-4,5-dihydro-1H-imidazole, rac-4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-2-one, rac-1-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-ethanone,

[(4S,5R)-4,5-Bis-(4-chloro-phenyl)-2-(2-ethoxy-4-trifluoromethyl-phenyl)-4,5-dimethyl-4,5-dihydro-imidazol-1-yl]-[4-(3-methanesulfonyl-propyl)-piperazin-1-yl]-methanone, rac-2-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-1-morpholin-4-yl-ethanone, rac-(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-ethanesulfonyl-piperazin-1-yl)-methanone, rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (1-methanesulfonyl-piperidin-4-yl)-amide, rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(4-methyl-piperazin-1-yl)-piperidin-1-yl]-methanone, rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-morpholin-4-yl-piperidin-1-yl)-methanone, rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxy-piperidin-1-yl)-methanone, rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxymethyl-piperidin-1-yl)-methanone, rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(2-hydroxy-ethyl)-piperidin-1-yl]-methanone, rac-1-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperidine-4-carboxylic acid amide, rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid bis-(2-hydroxy-ethyl)-amide, rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (2,3-dihydroxy-propyl)-amide, 3-{4-[4,5-Bis-(4-chloro-phenyl)-4,5-dimethyl-4,5-dihydro-1H-imidazol-2-yl]-3-ethoxy-phenyl}-3-methyl-butan-2-one, 3-(4-{4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-3-methyl-butan-2-one, 3-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-3-methyl-butan-2-one, 2-(4-{(4S,5R)-4,5-Bis-(4-chloro-phenyl)-2-[4-(1,1-dimethyl-2-oxo-propyl)-2-ethoxy-phenyl]-4,5-dimethyl-4,5-dihydro-imidazole-1-carbonyl}-piperazin-1-yl)-acetamide, rac-(4S*,5R*)-2-(4-tert-Butyl-2-isopropoxy-phenyl)-4,5-bis-(4-chloro-phenyl)-4,5-dimethyl-4,5-dihydro-1H-imidazole, rac-1-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-ethanone, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(4-isopropyl-piperazin-1-yl)-methanone, rac-4-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-butyronitrile, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(3-methoxy-propyl)-piperazin-1-yl]-methanone, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-morpholin-4-yl-ethyl)-piperazin-1-yl]-methanone, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(tetrahydro-furan-2-ylmethyl)-piperazin-1-yl]-methanone, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(hexahydro-pyrrolo[1,2-a]pyrazin-2-yl)-methanone, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(octahydro-pyrido[1,2-a]pyrazin-2-yl)-methanone, rac-(4S*,5R*)-2-(4-tert-Butyl-2-isopropoxy-phenyl)-4,5-bis-(4-chloro-phenyl)-4,5-dimethyl-4,5-dihydro-imidazole-1-carboxylic acid bis-(2-methoxy-ethyl)-amide, rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-methoxy-ethyl)-piperazin-1-yl]-methanone,

[(4S,5R)-2-(4-tert-Butyl-2-isopropoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-4-isopropyl-phenyl)-4,5-dimethyl-4,5-dihydro-imidazol-1-yl]-[4-(3-methanesulfonyl-propyl)-piperazin-1-yl]-methanone,

[(4S,5R)-2-(5-tert-Butyl-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-5-methanesulfonyl-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-4-methanesulfonyl-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(4-cyclopropyl-2-ethoxy-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(5-cyclopropyl-2-ethoxy-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(4-ethanesulfonyl-2-ethoxy-phenyl)-4,5-dimethyl-4,5-dihydro-imidazol-1-yl]-[4-(3-methanesulfonyl-propyl)-piperazin-1-yl]-methanone,

[(4S,5R)-2-(4-tert-Butyl-2-ethoxy-phenyl)-4,5-bis-(4-chloro-phenyl)-4,5-diethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-4-ethylsulfanyl-phenyl)-4,5-dimethyl-4,5-dihydro-imidazol-1-yl]-[4-(3-methanesulfonyl-propyl)-piperazin-1-yl]-methanone,

[(4S,5R)-2-(4-tert-Butyl-2-methoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-2-(4-Chloro-2-ethoxy-5-methanesulfonyl-phenyl)-4,5-bis-(4-chloro-phenyl)-4,5-dimethyl-4,5-dihydro-imidazol-1-yl]-[4-(1,1-dioxo-tetrahydro-2H-thiopyran-4-yl)-piperazin-1-yl]-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(1,1-dioxo-tetrahydro-thiophen-3-yl)-piperazin-1-yl]-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(3-ethanesulfonyl-propyl)-piperazin-1-yl]-methanone, 2-(4-{(4S,5R)-4,5-Bis-(4-chloro-phenyl)-1-[4-(3-ethanesulfonyl-propyl)-piperazine-1-carbonyl]-4,5-dimethyl-4,5-dihydro-1H-imidazol-2-yl}-3-ethoxy-phenyl)-2-methyl-propionitrile, (4S,5R)-2-(4-tert-Butyl-2-ethoxy-phenyl)-4,5-bis-(4-chloro-phenyl)-4-methyl-4,5-dihydro-1H-imidazole,

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone,

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone, 1-[(4S,5R)-2-(4-tert-Butyl-2-ethoxy-phenyl)-4,5-bis-(4-chloro-phenyl)-4-methyl-4,5-dihydro-imidazole-1-carbonyl]-piperidine-4-carboxylic acid amide, 1-{4-[(4S,5R)-2-(4-tert-Butyl-2-ethoxy-phenyl)-4,5-bis-(4-chloro-phenyl)-4-methyl-4,5-dihydro-imidazole-1-carbonyl]-piperazin-1-yl}-ethanone, rac-(4S*,5R*)-2-(4-tert-Butyl-2-ethoxy-phenyl)-4,5-bis-(4-chloro-phenyl)-4-methyl-4,5-dihydro-imidazole-1-carboxylic acid (2-dimethylamino-ethyl)-amide, rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-2-one, rac-2-{4-[(4S,5R)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-morpholin-4-yl-ethanone, rac-[(4S,5R)-2-(4-tert-Butyl-2-ethoxy-phenyl)-4,5-bis-(4-chloro-phenyl)-4-methyl-4,5-dihydro-imidazol-1-yl]-(4-methanesulfonyl-piperazin-1-yl)-methanone, rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-pyrrolidin-1-yl-ethanone, rac-[(4S*,5R*)-2-(4-tert-Butyl-2-ethoxy-phenyl)-4,5-bis-(4-chloro-phenyl)-4-methyl-4,5-dihydro-imidazol-1-yl]-[4-(tetrahydro-furan-2-carbonyl)-piperazin-1-yl]-methanone, rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazine-1-carboxylic acid dimethylamide, rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-acetamide, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-pyrrolidin-1-yl-ethanone, rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-2-one, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-morpholin-4-yl-ethanone, rac-[(4S*,5R*)-4,5-Bis-(4-chloro-phenyl)-2-(2-isopropoxy-4-methoxy-phenyl)-4-methyl-4,5-dihydro-imidazol-1-yl]-(4-methanesulfonyl-piperazin-1-yl)-methanone, rac-1-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-ethanone, rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(tetrahydro-furan-2-carbonyl)-piperazin-1-yl]-methanone, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-acetamide, rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazine-1-carboxylic acid dimethylamide, rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(2-isopropoxy-4-methoxy-phenyl)-4-methyl-4,5-dihydro-imidazol-1-yl]-piperazin-1-yl-methanone, rac-(4S*,5R*)-4,5-Bis-(4-chloro-phenyl)-2-(2-isopropoxy-4-methoxy-phenyl)-4-methyl-4,5-dihydro-imidazole-1-carboxylic acid (2-dimethylamino-ethyl)-amide, rac-1-[(4S*,5R*)-4,5-Bis-(4-chloro-phenyl)-2-(2-isopropoxy-4-methoxy-phenyl)-4-methyl-4,5-dihydro-imidazole-1-carbonyl]-piperidine-4-carboxylic acid amide, rac-4-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperazin-2-one, rac-1-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperidine-4-carboxylic acid amide, rac-[(4S*,5R*)-4,5-Bis-(4-chloro-phenyl)-4-ethyl-2-(2-isopropoxy-4-methoxy-phenyl)-4,5-dihydro-imidazol-1-yl]-[4-(tetrahydro-furan-2-carbonyl)-piperazin-1-yl]-methanone, rac-2-{4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazin-1-yl}-1-morpholin-4-yl-ethanone and rac-4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazine-1-carboxylic acid dimethylamide.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds.

The term "halogen" as used in the definitions means fluorine, chlorine, bromine, or iodine, preferably fluorine and chlorine.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

The compounds of formula I as well as their salts that have at least one asymmetric carbon atom may be present as racemic mixtures or different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in formula I above.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid.

Information concerning esters and the use of esters for the delivery of pharmaceutical compounds is available in Design of Prodrugs. Bundgaard H ed. (Elsevier, 1985). See also, H. Ansel et al., Pharmaceutical Dosage Forms and Drug Delivery Systems (6th Ed. 1995) at pp. 108-109; Krogsgaard-Larsen, et al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted" means that the substitution can occur at one or more positions and, unless otherwise indicated, that the substituents at each substitution site are independently selected from the specified options.

"Therapeutically effective amount" means an amount of at least one designated compound, that significantly inhibits proliferation and/or prevents differentiation of a human tumor cell, including human tumor cell lines.

Compounds of the present invention as exemplified advantageously show IC50s from about 1 nM to about 1000 nM.

The present invention also provides pharmaceutical compositions comprising at least one compound of formula I, or a pharmaceutically acceptable salt or ester thereof, and a pharmaceutically acceptable carrier or excipient.

Schemes

The general methods for the preparation of compounds of formula I are given in schemes 1, 2, 3 and 4. Briefly, the process involves the formation of imidazoline (V) either by condensation of a tetrasubstituted 1,2-diamine (II) with an aromatic acid (III) to form a monoamide derivative (IV) followed by cyclodehydration (method 1, scheme 1) or by reaction of a tetrasubstituted 1,2-diamine (II) with an aromatic ester (VI) in the presence of a trialkyl aluminum (method 2, scheme 2). The imidazoline (V) is reacted with phosgene to form carbamoyl chloride (VII) which is then reacted with primary or secondary amines to form urea derivatives (I) (scheme 3). The imidazoline (V) can also be reacted with acid chlorides (VIII) in the presence of a base such as triethylamine to form amide derivatives (I) (scheme 3).

The absolute stereochemistry of the active enantiomer of I is determined based on the crystal structure of its complex with human MDM2 (see Vassilev, L. et al. *Science* 2004, 303, 844-848).

Preparation of Imidazolines

Method 1: Diamines with Acids

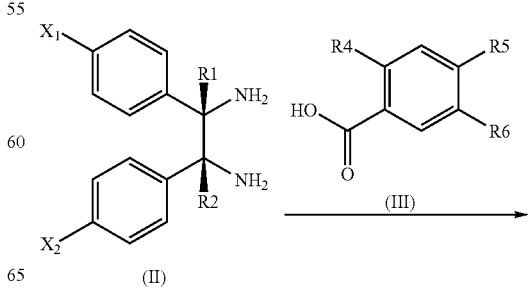

Method 2: Diamines with Esters
Scheme 2
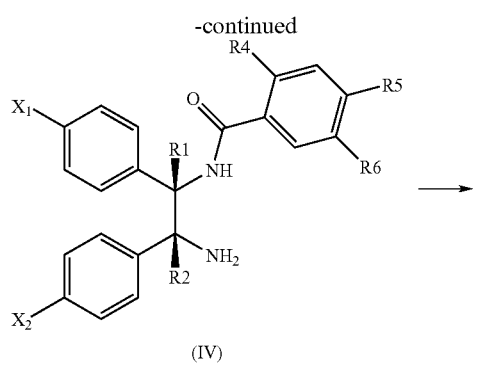
(IV)
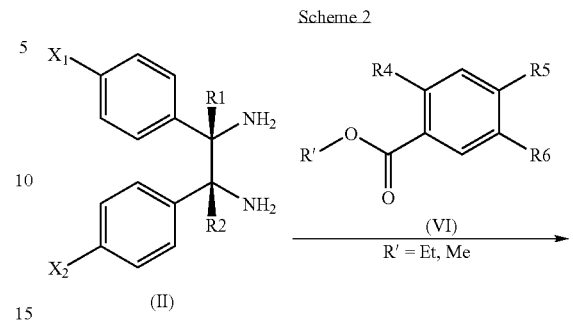
(II) + (VI), R' = Et, Me
(V)
Derivatization of Imidazolines
Scheme 3
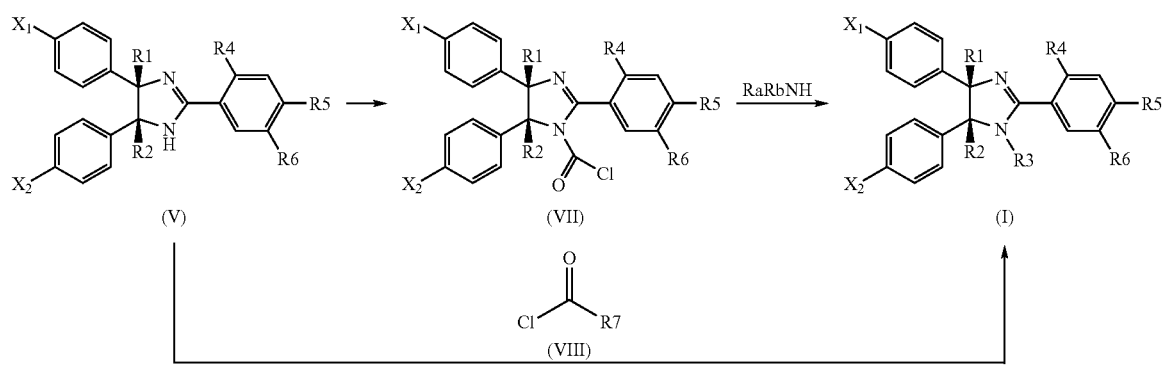

Preparation of Diamine Intermediates

The diamine intermediates were prepared either by the reductive coupling of imines via the process described by Volckaerts [B. Bracke, E. Voickaerts, A. T. H. Lenstra, H. J. Geise, H. J., Bulletin des Societes Chimiques Belges, 1990, 99, 797-801.] (method 3) or by the reaction of 1,2,5-thiadiazole 1,1-dioxides with Grignard reagents via a process described by Pansare [S. V. Pansare, A. N. Rai, S. N. Kate, Synlett, 1998, 623-624] (method 4).

Method 3:

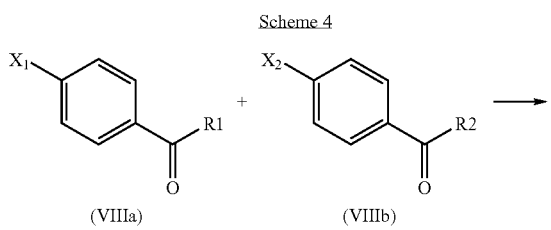

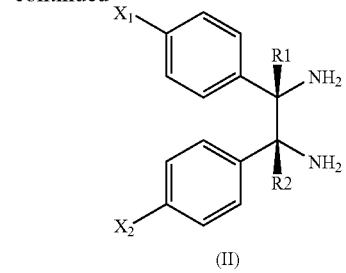

The following examples and references are provided to aid the understanding of the present invention, the true scope of which is set forth in the appended claims.

General: In the examples temperatures are indicated in degrees C. For mass spectral data, values are given as the MH+/Z ion obtained in the positive mode, electrospray measured on a Micromass Platform II mass spectrometer.

EXAMPLE 1 meso-2,3-bis-(4-chlorophenyl)-2,3-butanediamine

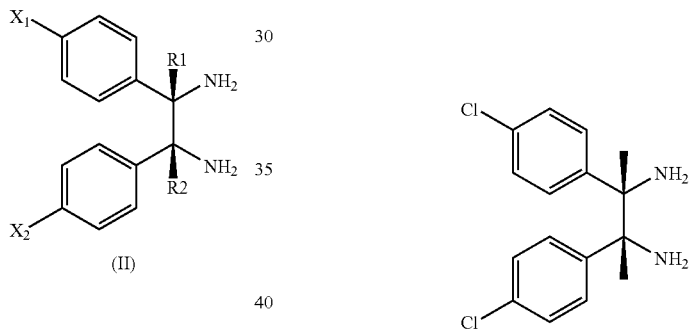

Method 4:

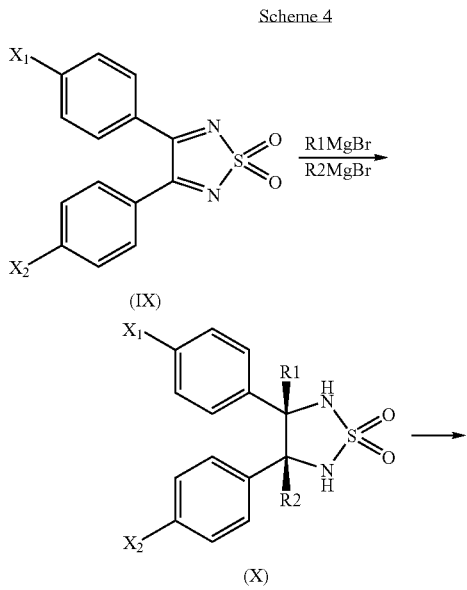

A mixture of 15.0 g (97.3 mmol) of titanium trichloride and 480 mL of tetrahydrofuran under an argon atmosphere was cooled to −15° C. and then 48.64 mL of a 1 M solution of lithium aluminum hydride in tetrahydrofuran was added dropwise. The mixture was stirred for 10 min, then heated to reflux for 1 h. The mixture was cooled to room temperature and solutions of 50 mL of ammonia in 192 mL of tetrahydrofuran and 15.04 g (97.3 mmol) of 4-chloroacetophenone in 240 mL of tetrahydrofuran were added simultaneously over 40 min. The mixture was stirred overnight at room temperature, then cooled to 0° C. and acidified by addition of 2 M hydrochloric acid. The aqueous phase was extracted with dichloromethane, then made basic by the addition of 2 M sodium hydroxide solution and extracted with dichloromethane. The latter dichloromethane phase was dried over anhydrous sodium sulfate, filtered and concentrated under reduced pressure to give 4.64 g of 2,3-bis-(4-chlorophenyl)-2,3-butanediamine as a mixture of meso and dl-isomers. This material was used without further purification in subsequent reactions.

EXAMPLE 2 rac-(4S*,5R*)-4,5-Bis(4-chlorophenyl)-2-(4-(tert-butyl)-2-ethoxy-phenyl)-4,5-dimethyl-4,5-dihydro-1H-imidazole

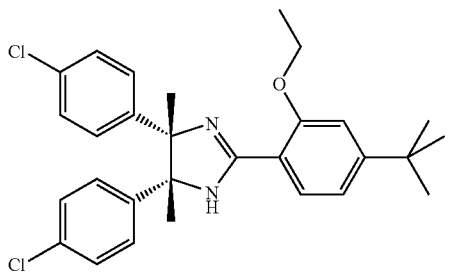

Method 1:

A mixture of meso-2,3-bis-(4-chlorophenyl)-2,3-butanediamine (70 mg, 0.226 mmol, example 1) and triethylamine (62 uL, 0.226 mmol) in 2 mL of dichloromethane was reacted with 0.225 mmol of 4-(tert-butyl)-2-ethoxy-benzoyl chloride (prepared from the reaction of 0.225 mmol of 4-(tert-butyl)-2-ethoxy-benzoic acid and 0.34 mmol of oxalyl chloride) for 30 min at room temperature. The mixture was partitioned between 10% sodium bicarbonate solution and dichloromethane. The dichloromethane extract was washed with water, dried over anhydrous sodium sulfate, filtered and concentrated under reduced pressure to give the crude amide mixture. Purification by chromatography on silica gel, eluting with hexane-ethyl acetate (3:1) provided 20 mg of N-[2-amino-1,2-bis-(4-chloro-phenyl)-1-methyl-propyl]-4-(tert-butyl)-2-ethoxy-benzamide. The intermediate was refluxed under argon with 0.5 mg of toluenesulfonic acid monohydrate and 7 mL of toluene for 3.5 h, then cooled, taken up in ethyl acetate and washed successively with saturated sodium bicarbonate, water and brine. The ethyl acetate layer was dried over anhydrous sodium sulfate, filtered, and concentrated under reduced pressure. Purification by chromatography on silica gel, eluting with ethyl acetate, followed by ethyl acetate-methanol (95:5) provided 9.5 mg of rac-(4S*,5R*)-4,5-bis(4-chlorophenyl)-2-(4-(tert-butyl)-2-ethoxy-phenyl)-4,5-dimethyl-4,5-dihydro-1H-imidazole. LR-MS: 495.0 [(M+H)$^+$]

Method 2:

A solution of meso-2,3-bis-(4-chlorophenyl)-2,3-butanediamine (2.5 g, 8.08 mmol, example 1) in 100 mL of toluene was added to a solution of trimethylaluminum (4 mL, 2M solution in toluene, Aldrich) in 24 mL of toluene at 0° C. The mixture was stirred 10 min at 0° C., 20 min at room temperature and then 4-(tert-butyl)-2-ethoxy-benzoic acid methyl ester (2.1 g, 8.9 mmol) in 10 mL of toluene was added. The mixture was heated to reflux for 2.5 h then cooled to 0° C. and quenched by the dropwise addition of saturated potassium sodium tartrate solution. The mixture was extracted with ethyl acetate and the ethyl acetate layer washed successively with 10% sodium bicarbonate solution and brine, then dried over anhydrous sodium sulfate, filtered and concentrated under reduced pressure. Purification by chromatography on silica gel, eluting with hexane-ethyl acetate (1:1) provided 710 mg of rac-(4S*,5R*)-4,5-bis(4-chlorophenyl)-2-(4-(tert-butyl)-2-ethoxy-phenyl)-4,5-dimethyl-4,5-dihydro-1H-imidazole. LR-MS: 495.0 [(M+H)$^+$]

EXAMPLE 3 rac-(4S*,5R*)-4,5-Bis(4-chlorophenyl)-2-(4-(tert-butyl)-2-ethoxy-phenyl)-4,5-dimethyl-4,5-dihydro-1H-imidazole-1-carbonyl chloride

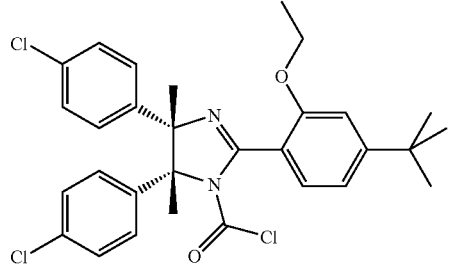

To a solution of rac-(4S*,5R*)-4,5-bis(4-chlorophenyl)-2-(4-(tert-butyl)-2-ethoxy-phenyl)-4,5-dimethyl-4,5-dihydro-1H-imidazole (710 mg, 1.43 mmol, example 2) and triethylamine (400 uL, 2.86 mmol) in 12 mL of dichloromethane at 0° C. was added 1.13 mL of 1.9 M phosgene in toluene solution (Fluka). After stirring for 30 min the mixture was taken up in dichloromethane and washed with water, dried over anhydrous sodium sulfate, filtered and concentrated under reduced pressure. Purification by chromatography on silica gel, eluting with hexane-ethyl acetate (4:1) provided 689 mg of rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride as a white solid.

EXAMPLE 4

(4S,5R)-4,5-Bis(4-chlorophenyl)-2-(4-(tert-butyl)-2-ethoxy-phenyl)-4,5-dimethyl-4,5-dihydro-1H-imidazole-1-carbonyl chloride

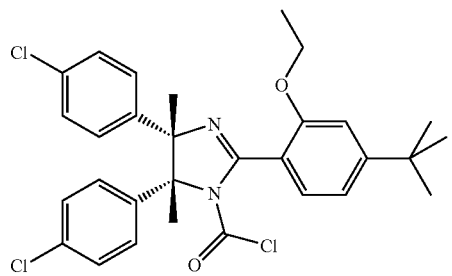

Chiral separation of rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride (example 4) by supercritical fluid chromatography (Berger Instrument Multi-Gram II, Daicel ChiralPak OD-H 3×25 cm, 35 CC at 100 bar, eluting with 15% acetonitrile in carbon dioxide) gave the title compound.

EXAMPLE 5

(4S,5R)-4-[[4-[[4,5-Bis(4-chlorophenyl)-2-[4-(tert-butyl)-2-ethoxy-phenyl]-4,5-dimethyl-4,5-dihydro-1H-imidazol-1-yl]carbonyl]-1-piperazinyl]acetyl]-morpholine

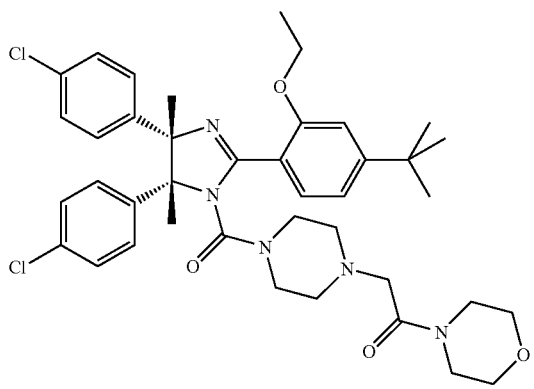

To a solution of rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride (50 mg, 0.09 mmol, example 4) in 5 mL of dichloromethane at 0° C. were added triethylamine (165 uL, 1.186 mmol) and 4-(1-piperazinylacetyl)-morpholine (20 mg (0.097 mmol, Oakwood Products). The mixture was allowed to react for 20 h and then taken up in dichloromethane and washed successively with 10% sodium bicarbonate and water. The dichloromethane phase was dried over anhydrous sodium sulfate, filtered and concentrated under reduced pressure. Purification by chromatography on silica gel eluting with ethyl acetate-methanol (95:5) provided 55.4 mg of rac-(4S*,5R*)-4-[[4-[[4,5-bis(4-chlorophenyl)-2-[4-(tert-butyl)-2-ethoxy-phenyl]-4,5-dimethyl-4,5-dihydro-1H-imidazol-1-yl]carbonyl]-1-piperazinyl]acetyl]-morpholine. Separation of the enantiomers by chiral HPLC gave 24 mg of (4S,5R)-4-[[4-[[4,5-bis(4-chlorophenyl)-2-[4-(tert-butyl)-2-ethoxy-phenyl]-4,5-dimethyl-4,5-dihydro-1H-imidazol-1-yl]carbonyl]-1-piperazinyl]acetyl]-morpholine. HR-MS (ES, m/z) calculated for $C_{40}H_{50}N_5O_4Cl_2$ [(M+H)$^+$] 734.3235, observed 734.3237.

EXAMPLE 6

(4S,5R)-4-[[4-[[4,5-bis(4-chlorophenyl)-2-[4-(tert-butyl)-2-ethoxy-phenyl]-4,5-dimethyl-4,5-dihydro-1H-imidazol-1-yl]carbonyl]-1-piperidine

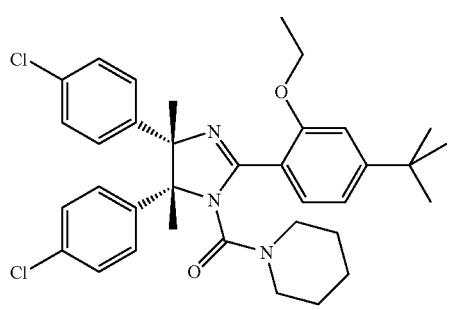

In a manner analogous to the method described in example 5, rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride (50 mg, 0.09 mmol) was reacted with piperidine (Aldrich) to give 24 mg of the title compound after chiral separation. HR-MS (ES, m/z) calculated for $C_{35}H_{42}N_3O_2Cl_2$ [(M+H)$^+$] 606.2649, observed 606.2650.

EXAMPLE 7

(4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine

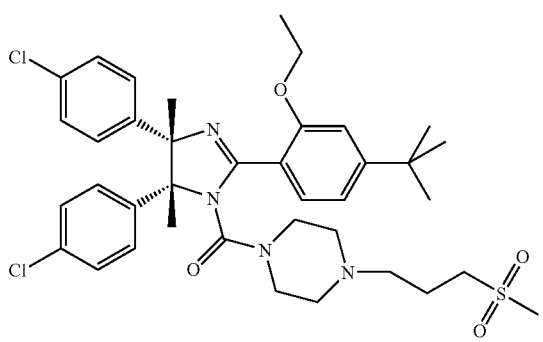

In a manner analogous to the method described in example 5, rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride (50 mg, 0.09 mmol) was reacted with 4-[3-(methylsulfonyl)propyl]-piperazine (0.09 mmol, prepared as described in Fotouhi, N. et al. WO 2005110996) to give 24 mg of the title compound after chiral separation. HR-MS (ES, m/z) calculated for $C_{38}H_{49}N_4O_4SCl_2$ [(M+H)$^+$] 727.2846, observed 727.2846.

EXAMPLE 8

(4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3,3,3-trifluoropropyl]-piperazine

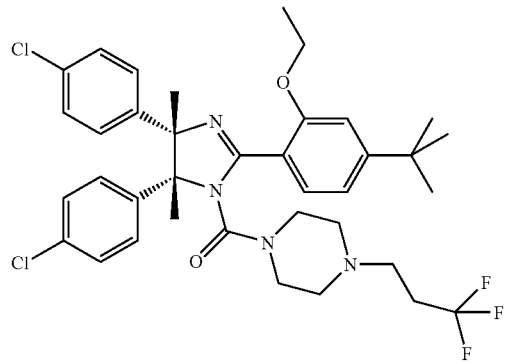

In a manner analogous to the method described in example 5, rac-(4S*,5R*)-4,5-bis(4-chlorophenyl)-2-(4-(tert-butyl)-2-ethoxy-phenyl)-4,5-dimethyl-4,5-dihydro-1H-imidazole-1-carbonyl chloride (50 mg, 0.09 mmol) was reacted with 4-[3-(methylsulfonyl)-propyl]-piperazine (0.09 mmol, prepared as described in Fotouhi, N. et al. WO 2005110996) to give 38 mg of the title compound after chiral separation. HR-MS (ES, m/z) calculated for $C_{37}H_{44}N_4O_2F_3Cl_2$ [(M+H)$^+$] 727.2846, observed 727.2846.

EXAMPLE 9

2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-acetamide

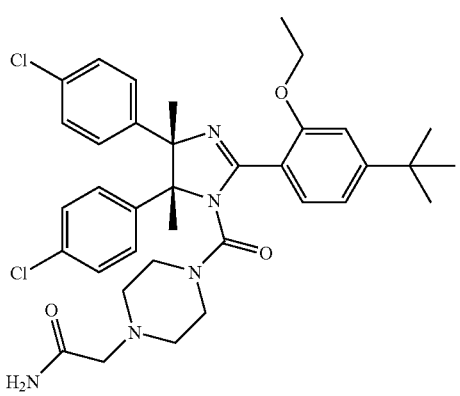

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with 2-piperazin-1-yl-acetamide dihydrochloride (Matrix Scientific) to give the title compound. HR-MS (ES, m/z) calculated for $C_{36}H_{44}N_5O_3Cl_2$ [(M+H)$^+$] 664.2816, observed 664.2810.

EXAMPLE 10

2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-1-pyrrolidin-1-yl-ethanone

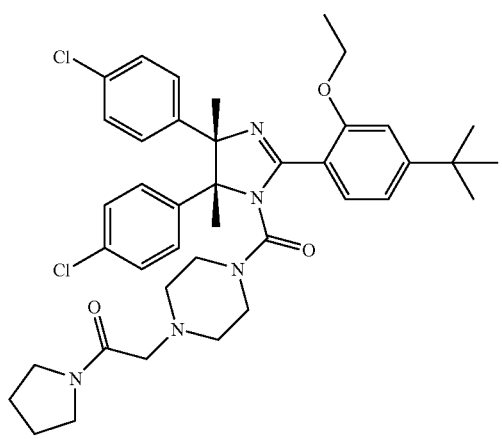

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with 2-piperazin-1-yl-1-pyrrolidin-1-yl-ethanone (Aldrich) to give the title compound. HR-MS (ES, m/z) calculated for $C_{40}H_{50}N_5O_3Cl_2$ [(M+H)$^+$] 718.3285, observed 718.3286.

EXAMPLE 11

N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-acetamide

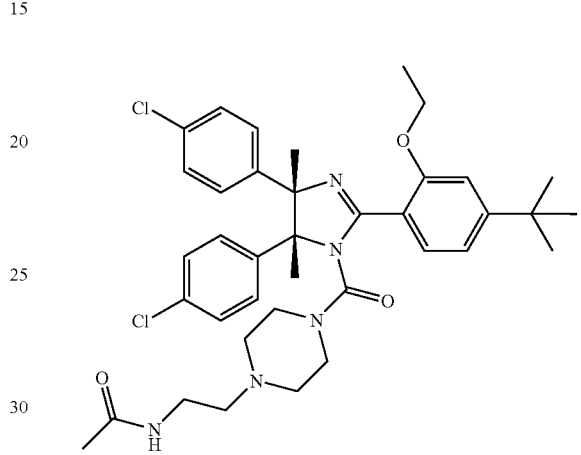

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with N-(2-piperazin-1-yl-ethyl)-acetamide dihydrochloride (prepared as described in Fotouhi, N. et al. WO 2005110996) to give the title compound. HR-MS (ES, m/z) calculated for $C_{38}H_{48}N_5O_3Cl_2$ [(M+H)$^+$] 692.3129, observed 692.3125.

EXAMPLE 12

N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-methanesulfonamide

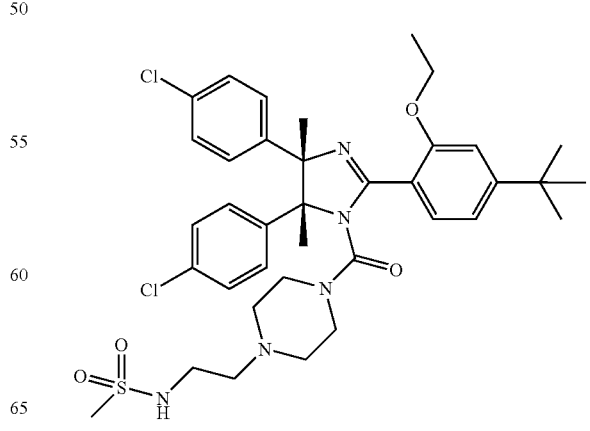

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with N-(2-piperazin-1-yl-ethyl)-methanesulfonamide dihydrochloride (prepared as described in Fotouhi, N. et al. WO 2005110996) to give the title compound. HR-MS (ES, m/z) calculated for $C_{37}H_{48}N_5O_4SCl_2$ $[(M+H)^+]$ 782.2799, observed 782.2787.

EXAMPLE 13

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(2-hydroxy-ethyl)-piperazin-1-yl]-methanone

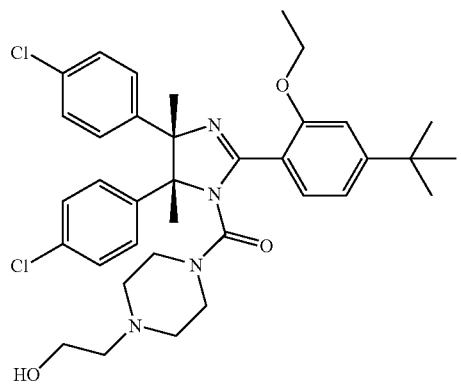

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with 2-piperazin-1-yl-ethanol (Chemical Dynamics) to give the title compound. HR-MS (ES, m/z) calculated for $C_{36}H_{45}N_4O_3Cl_2$ $[(M+H)^+]$ 651.2863, observed 651.2863.

EXAMPLE 14

(S)-4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-1-methyl-piperazine-2-carboxylic acid methyl ester

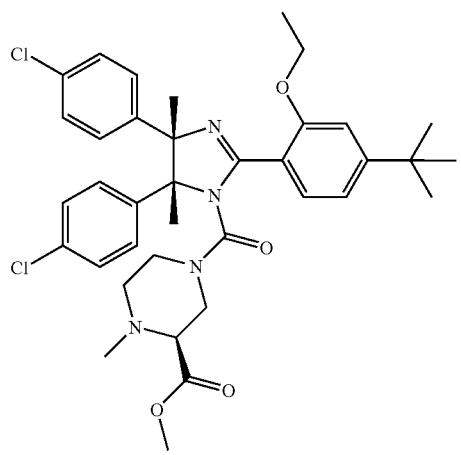

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with (S)-1-methyl-piperazine-2-carboxylic acid methyl ester (Aldrich) to give the title compound. HR-MS (ES, m/z) calculated for $C_{37}H_{45}N_4O_4Cl_2$ $[(M+H)^+]$ 679.2813, observed 679.2805.

EXAMPLE 15

5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-2-tert-butyl-4-ethoxy-N,N-dimethyl-benzenesulfonamide

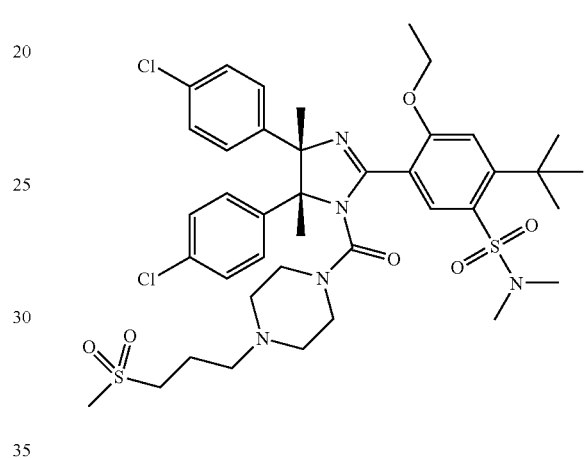

In a manner analogous to the method described in example 2, meso-2,3-bis-(4-chlorophenyl)-2,3-butanediamine (example 1) was reacted with 4-tert-butyl-5-dimethylsulfamoyl-2-ethoxy-benzoic acid methyl ester (prepared in an analogous manner as described in example 43) in the presence of trimethylaluminum to give rac-5-[(4S*,5R*)-4,5-bis-(4-chloro-phenyl)-4,5-dimethyl-4,5-dihydro-1H-imidazol-2-yl]-2-tert-butyl-4-ethoxy-N,N-dimethyl-benzenesulfonamide.

In a manner analogous to the method described in example 3, rac-5-[(4S*,5R*)-4,5-bis-(4-chloro-phenyl)-4,5-dimethyl-4,5-dihydro-1H-imidazol-2-yl]-2-tert-butyl-4-ethoxy-N,N-dimethyl-benzenesulfonamide was reacted with phosgene in the presence of triethylamine to give rac-(4S*,5R*)-2-(4-tert-butyl-5-dimethylsulfamoyl-2-ethoxy-phenyl)-4,5-bis-(4-chloro-phenyl)-4,5-dimethyl-4,5-dihydro-imidazole-1-carbonyl chloride. The carbamoyl chloride was then reacted with 1-(3-methanesulfonyl-propyl)-piperazine dihydrochloride (prepared as described in Fotouhi, N. et al. WO 2005110996) in the presence of triethylamine to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{40}H_{53}N_5O_6S_2Cl_2$ $[(M+H)^+]$ 834.2887, observed 834.2878.

EXAMPLE 16 rac-2-{4-[(4S*,5R*)-4,5-Bis-(4-chloro-phenyl)-4,5-dimethyl-4,5-dihydro-1H-imidazol-2-yl]-3-ethoxy-phenyl}-2-methyl-propionitrile

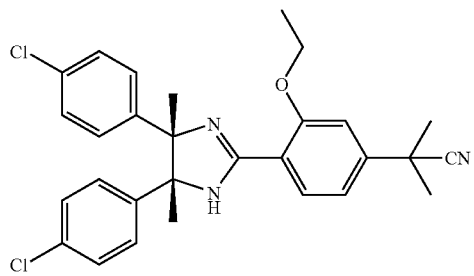

In a manner analogous to the method described in example 2, meso-2,3-bis-(4-chlorophenyl)-2,3-butanediamine was reacted with 4-(cyanodimethyl-methyl)-2-ethoxybenzoic acid methyl ester (prepared as described in Fotouhi, N. et al. WO 2005110996) in the presence of trimethylaluminum to give the title compound. LR-MS: 506.0 [(M+H)+]

EXAMPLE 17 rac-(4S*,5R*)-4,5-Bis-(4-chloro-phenyl)-2-[4-(cyano-dimethyl-methyl)-2-ethoxy-phenyl]-4,5-dimethyl-4,5-dihydro-imidazole-1-carbonyl chloride

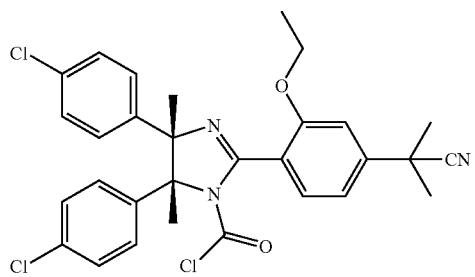

In a manner analogous to the method described in example 3, 2-{4-[rac-(4S*,5R*)-4,5-bis-(4-chloro-phenyl)-4,5-dimethyl-4,5-dihydro-1H-imidazol-2-yl]-3-ethoxy-phenyl}-2-methyl-propionitrile (example 17) was reacted with phosgene in the presence of triethylamine to give the title compound.

EXAMPLE 18

2-(4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-2-methyl-propionitrile

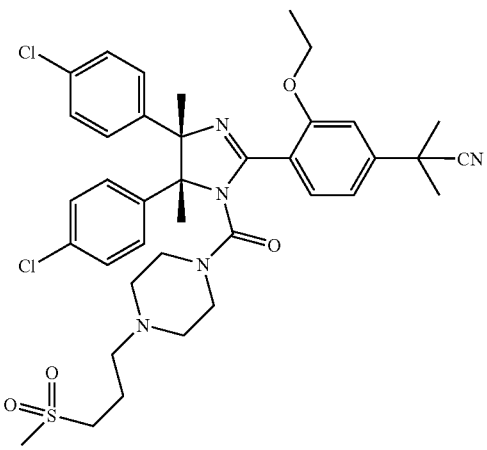

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 738.0 [(M+H)+]

EXAMPLE 19

N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-methanesulfonamide

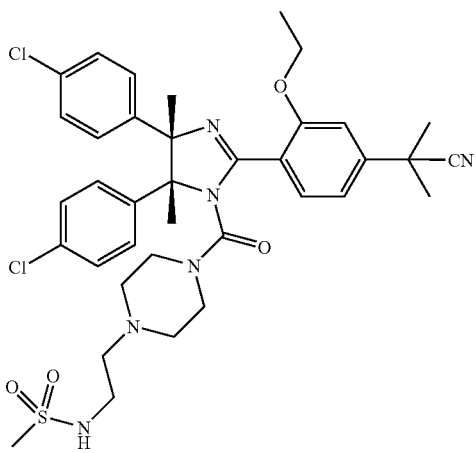

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with N-(2-piperazin-1-yl-ethyl)-methanesulfonamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 739.3 [(M+H)$^+$]

EXAMPLE 20

N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-acetamide

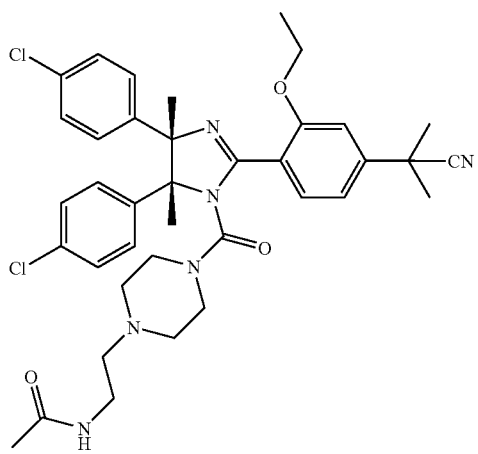

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with N-(2-piperazin-1-yl-ethyl)-acetamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 703.3 [(M+H)$^+$]

EXAMPLE 21

2-(4-{(4S,5R)-4,5-Bis-(4-chloro-phenyl)-1-[4-(2-hydroxy-ethyl)-piperazine-1-carbonyl]-4,5-dimethyl-4,5-dihydro-1H-imidazol-2-yl}-3-ethoxy-phenyl)-2-methyl-propionitrile

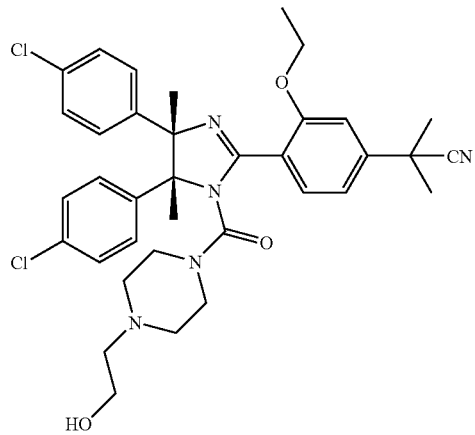

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 2-piperazin-1-yl-ethanol (Chemical Dynamics) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 662.2 [(M+H)$^+$]

EXAMPLE 22

2-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-2-methyl-propionitrile

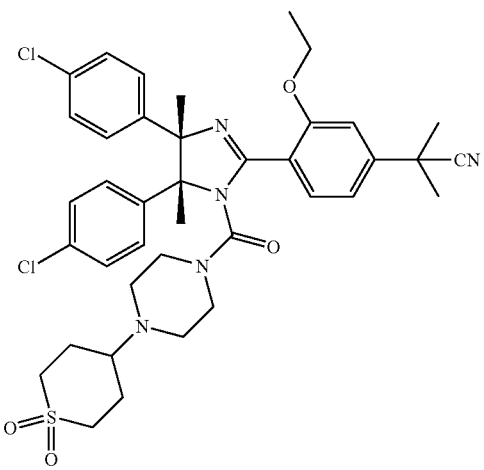

To a stirred solution of tetrahydrothiopyran-4-one (5.30 g, 43.1 mmol, Aldrich) in 50 mL of ethyl acetate was added dropwise 32% peracetic acid (24 g, 110 mmol) at a rate to avoid reflux. After the addition, the mixture was cooled to room temperature and the solid filtered to give 1,1-dioxo-tetrahydro-thiopyran-4-one as a white solid (5.69 g, 89%).

Tetrahydro-4H-thiopyran-4-one (6 g, 40.5 mmol) was dissolved in 1,2-dichloroethane (250 mL) with some help of heating. When the temperature goes back to room temperature, 1-Boc-piperazine (7.62 g, 41 mmol), sodium triacetoxyborohydride (17.01 g, 56.7 mmol) were added followed by glacial acetic acid (2.4 g, 41 mmol). The reaction mixture was stirred at room temperature overnight. It was quenched with water, and the layers were separated. The aqueous layer was extracted with 1,2-dichloroethane (3×20 mL). The combined organic extracts were dried over sodium sulfate, filtered and concentrated to give a white solid. The white solid was purified by flash chromatography (ISCO machine, silica gel, eluting with 2-7% methanol-ethyl acetate in a period of 30 min) to give 4-(1,1-dioxo-tetrahydro-2H-thiopyran-4-yl)-piperazine-1-carboxylic acid tert-butyl ester as a white solid (9.3 g, 69%). LR-MS: 334 [(M+H)$^+$]

To a stirred solution of 4-(1,1-dioxo-tetrahydro-2H-thiopyran-4-yl)-piperazine-1-carboxylic acid tert-butyl ester (8.02 g, 25 mmol) in methanol at 45° C. (150 mL) was added 4 N hydrochloric acid in 1,4-dioxane (100 mmol, 25 mL, Aldrich). The mixture was stirred at 45° C. for 7 h until thin layer chromatography (5% methanol in ethyl acetate) indicated that the reaction was complete. The solvent was removed under reduced pressure to give 1-(1,1-dioxo-tetrahydro-2H-thiopyran-4-yl)-piperazine dihydrochloride as a white solid (7.24 g, 99.5%). LR-MS: 218 [(M+H)$^+$]

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 1-(1,1-dioxo-tetrahydro-2H-thiopyran-4-yl)-piperazine dihydrochloride to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 749.63 [(M+H)$^+$]

EXAMPLE 23

2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-acetamide

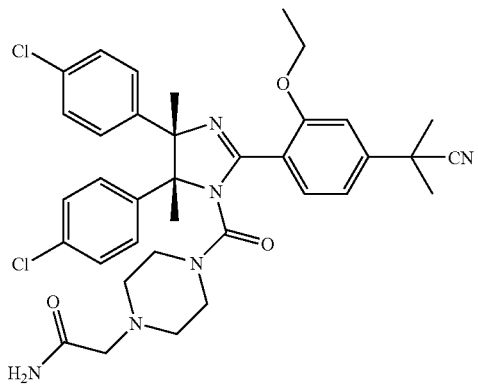

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 675.2 [(M+H)$^+$]

EXAMPLE 24

2-[4-((4S,5R)-4,5-Bis-(4-chloro-phenyl)-1-{4-[2-(1,1-dioxo-isothiazolidine-2-yl)-ethyl]-piperazine-1-carbonyl}-4,5-dimethyl-4,5-dihydro-1H-imidazol-2-yl)-3-ethoxy-phenyl]-2-methyl-propionitrile

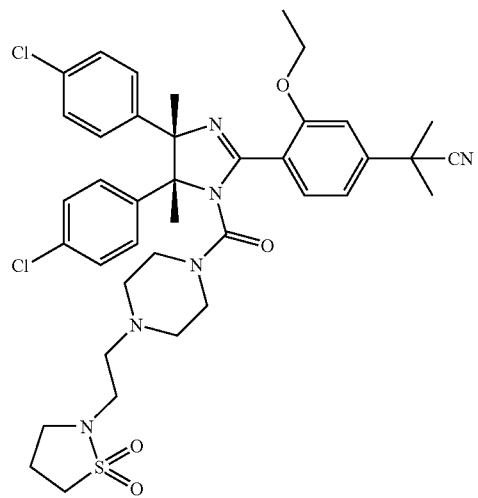

To a stirred solution of 1-Boc-4-(2-aminoethyl)-piperazine (1.26 g, 6.8 mmol, Aldrich) and triethylamine (1 mL) in tetrahydrofuran (10 mL), 3-chloro-propylsulfonyl chloride (0.68 mL, 6.94 mmol, Aldrich) was added slowly at room temperature. The mixture was stirred for 30 min at room temperature and the reaction was quenched with water. It was extracted with ethyl acetate and the extracts were combined and dried over anhydrous sodium sulfate. The solids were filtered off, and the filtrate was concentrated in vacuo to give 4-[2-(3-chloro-propane-1-sulfonylamino)-ethyl]-piperazine-1-carboxylic acid tert-butyl ester. It was taken in tetrahydrofuran (20 mL), and cesium carbonate (500 mg) sodium iodide (80 mg) were added and the mixture was stirred at reflux overnight. The mixture was cooled to room temperature and poured into water. It was extracted with ethyl acetate (3×15 mL), and the extracts were combined and dried over anhydrous sodium sulfate. The solids were filtered off, and the filtrate was concentrated in vacuo to give 2.01 g of 4-[2-(1,1-dioxo-isothiazolidine-2-yl)-ethyl]-piperazine-1-carboxylic acid tert-butyl ester as a solid. LR-MS: 334 [(M+H)$^+$]

4-[2-(1,1-Dioxo-isothiazolidine-2-yl)-ethyl]-piperazine-1-carboxylic acid tert-butyl ester (2.01 g) was treated with 30% trifluoroacetic acid in dichloromethane (10 mL), and the mixture was stirred at room temperature for 30 min. The mixture was concentrated in vacuo to give 2.46 g of 1-[2-(1,1-dioxo-isothiazolidine-2-yl)-ethyl]-piperazine trifluoroacetate as a solid. LR-MS: 234 [(M+H)$^+$]

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 1-[2-(1,1-dioxo-isothiazolidine-2-yl)-ethyl]-piperazine trifluoroacetate to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 765.0 [(M+H)$^+$]

EXAMPLE 25
2-(4-{(4S,5R)-4,5-Bis-(4-chloro-phenyl)-4,5-dimethyl-1-[4-(2-oxo-2-pyrrolidin-1-yl-ethyl)-piperazine-1-carbonyl]-4,5-dihydro-1H-imidazol-2-yl}-3-ethoxy-phenyl)-2-methyl-propionitrile

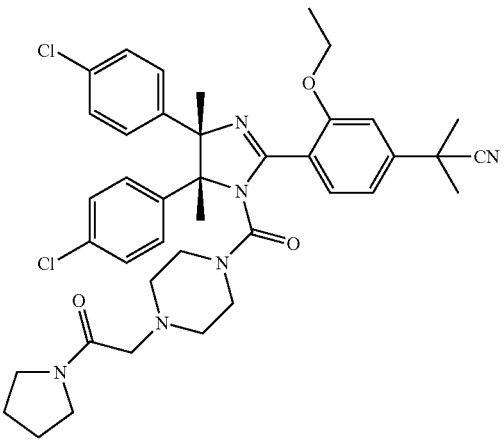

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 2-piperazin-1-yl-1-pyrrolidin-1-yl-ethanone (Aldrich) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 20% methanol in carbon dioxide). LR-MS: 729.4 [(M+H)$^+$]

EXAMPLE 26
2-{4-[(4S,5R)-1-[4-(1-Acetyl-piperidin-4-yl)-piperazine-1-carbonyl]-4,5-bis-(4-chloro-phenyl)-4,5-dimethyl-4,5-dihydro-1H-imidazol-2-yl]-3-ethoxy-phenyl}-2-methyl-propionitrile

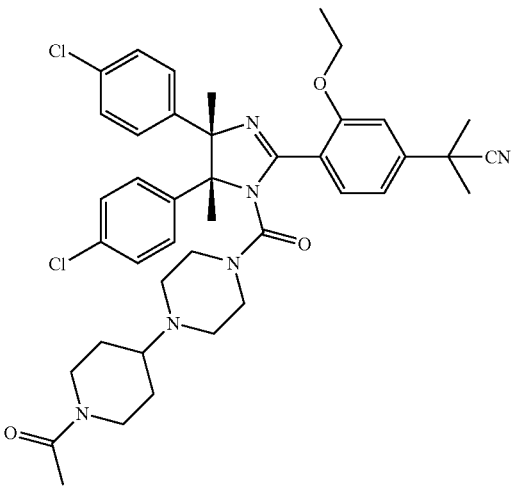

N-tert-butoxycarbonyl-piperazine (1.86 g, 10 mmol, Lancaster), N-Fmoc-4-oxo-piperidine (3.21 g, 10 mmol, Aldrich) and titanium(IV) isopropoxide (3.72 mL, Aldrich) were combined, and the mixture was stirred at room temperature for 1 h. Then ethyl alcohol (10 mL) was added followed by sodium cyanoborohydride (0.47 g, 7.48 mmol, Aldrich), and the mixture was stirred overnight. Water (2 mL) was added and the mixture was filtered. The solid was washed with ethyl alcohol and the filtrate was combined. The solvent was removed under reduced pressure and the residue was purified by flash chromatography (ISCO machine, silica gel, eluting with 20% ethyl acetate in hexane for a period of 30 min) to give 4-(1-Fmoc-piperidin-4-yl)-piperazine-1-carboxylic acid tert-butyl ester as a white foam (1.02 g).

4-(1-Fmoc-piperidin-4-yl)-piperazine-1-carboxylic acid tert-butyl ester (0.3 g, 0.61 mmol) was stirred with 20% piperidine in methylene chloride for 40 min. The mixture was concentrated to dryness to give 4-piperidin-4-yl-piperazine-1-carboxylic acid tert-butyl ester. It was then dissolved in tetrahydrofuran (5 mL), and triethylamine (308 mg, 3.05 mmol) and acetic anhydride (86 mg, 0.9 mmol) were added, respectively. After the reaction mixture was stirred for 2 h, water and ethyl acetate were added. The layers were separated, and the aqueous layer was extracted with ethyl acetate. The combined organic extracts were dried over anhydrous sodium sulfate. The solids were filtered off, and the filtrate was concentrated to give 4-(1-acetyl-piperidin-4-yl)-piperazine-1-carboxylic acid tert-butyl ester. It was dissolved in methylene chloride (7 mL), cooled with an ice bath and trifluoroacetic acid was added. The reaction mixture was stirred for 30 min, and the solvent was removed. The residue was triturated with diethyl ether and the solvent was removed to give 1-(4-piperazin-1-yl-piperidin-1-yl)-ethanone trifluoroacetate as a light-yellow foam (151 mg, 76%). LR-MS: 212 [(M+H)$^+$]

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 1-(4-piperazin-1-yl-piperidin-1-yl)-ethanone trifluoroacetate to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). LR-MS: 743.4 [(M+H)+]

EXAMPLE 27

4-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-piperidine-1-carboxylic acid isopropylamide

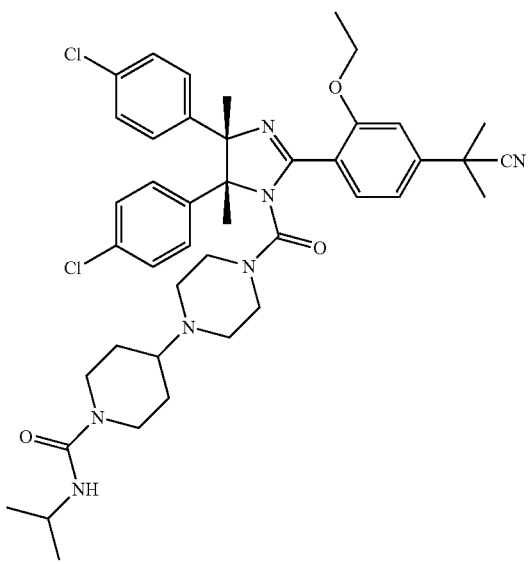

To a solution of 4-piperidin-4-yl-piperazine-1-carboxylic acid tert-butyl ester (108 mg, 0.4 mmol, example 27) in dichloromethane (2 mL) was added isopropyl isocyanate. The mixture was stirred for 1 h and quenched with water. After aqueous workup with water and dichloromethane, the organic layers was dried over anhydrous magnesium sulfate. The solids were filtered off, and the filtrate was concentrated to give 4-(1-isopropylcarbamoyl-piperidin-4-yl)-piperazine-1-carboxylic acid tert-butyl ester as a viscous oil.

In a manner analogous to the method described in example 27, 4-(1-isopropylcarbamoyl-piperidin-4-yl)-piperazine-1-carboxylic acid tert-butyl ester was treated with trifluoroacetic acid to give 4-piperazin-1-yl-piperidine-1-carboxylic acid isopropylamide trifluoroacetate as a yellow solid. LR-MS: 255 [(M+H)+]

In a manner analogous to the method described in example 5, rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 4-piperazin-1-yl-piperidine-1-carboxylic acid isopropylamide trifluoroacetate to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). LR-MS: 786.0 [(M+H)+]

EXAMPLE 28

2-Ethoxy-4-(pyrrolidine-1-sulfonyl)-benzoic acid methyl ester

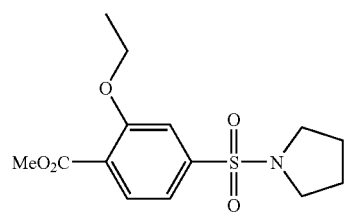

2-Ethoxy-4-thiol-benzoic acid (1.6 g, 8.08 mmol, prepared according to Robertson, D. et al. *J. Med. Chem.* 1985, 28, 717-727) was taken up in methanol (80 mL) and cooled to 0° C. Thionyl chloride (1.2 mL, 16.2 mmol) was added slowly. The reaction mixture was allowed to warm slowly to room temperature and stirred overnight. Evaporation of the solvents afforded a mixture of sulfide and disulfide methyl ester (1.9 g, 100%) as yellow oil, which was used without further purification. This crude sulfide/disulfide ester was taken up in acetic acid and cooled to 0° C. A small amount of toluene was added to the reaction mixture to prevent the reaction mixture from freezing. Chlorine gas ($Cl_2$) was bubbled into the reaction mixture until thin layer chromatography (50% ethyl acetate in hexanes) showed consumption of starting material. Argon gas (Ar) was bubbled into the reaction mixture to remove excess chlorine. The reaction mixture was concentrated to dryness in vacuo to give quantitative yield of the methyl 4-chlorosulfonyl-2-ethoxy-benzoate. It was taken up in anhydrous methylene chloride (50 mL) and cooled to 0° C. Triethylamine (8.5 mL, 62 mmol) and pyrrolidine (2.7 mL, 32.3 mmol) were added. The reaction mixture was allowed to slowly warm to room temperature and stirred at room temperature for 16 h. The reaction mixture was washed with water, dried over magnesium sulfate and concentrated. Purification of the crude residue by flash column chromatography (40 g of silica gel, eluting with 15-30% ethyl acetate in hexanes) gave -ethoxy-4-(pyrrolidine-1-sulfonyl)-benzoic acid methyl ester. HR-MS (ES, m/z) calculated for $C_{14}H_{20}NO_5$ [(M+H)+] 314.1057, observed 314.1056.

EXAMPLE 29

4-tert-Butylsulfamoyl-2-ethoxy-benzoic acid methyl ester

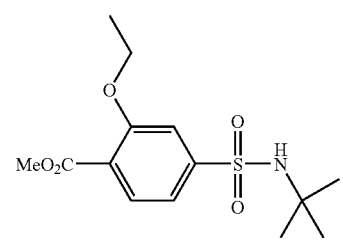

In a manner analogous to the method described in example 29, methyl 4-chlorosulfonyl-2-ethoxy-benzoate was reacted with tert-butylamine to give 4-tert-butylsulfamoyl-2-ethoxy-benzoic acid methyl ester.

EXAMPLE 30 rac-(4S*,5R*)-4,5-Bis-(4-chloro-phenyl)-2-[2-ethoxy-4-(pyrrolidine-1-sulfonyl)-phenyl]-4,5-dimethyl-4,5-dihydro-1H-imidazole

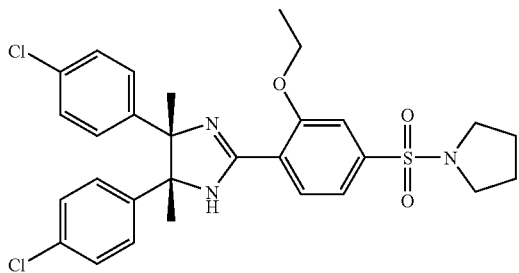

In a manner analogous to the method described in example 2, meso-2,3-bis-(4-chlorophenyl)-2,3-butanediamine was reacted with 2-ethoxy-4-(pyrrolidine-1-sulfonyl)-benzoic acid methyl ester in the presence of trimethylaluminum to give the title compound. HR-MS (ES, m/z) calculated for $C_{29}H_{32}N_3O_3SCl_2$ [(M+H)$^+$] 572.1536, observed 572.1534.

EXAMPLE 31 rac-(4S*,5R*)-4-[(4,5-Bis-(4-chloro-phenyl)-4,5-dimethyl-4,5-dihydro-1H-imidazol-2-yl]-N-tert-butyl-3-ethoxy-benzenesulfonamide

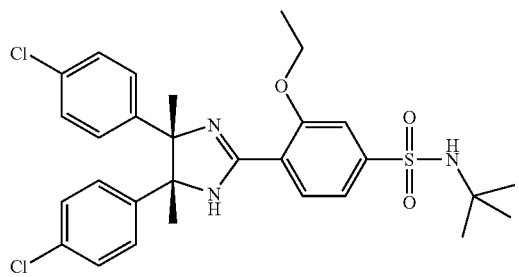

In a manner analogous to the method described in example 2, meso-2,3-bis-(4-chlorophenyl)-2,3-butanediamine was reacted with 4-tert-butylsulfamoyl-2-ethoxy-benzoic acid methyl ester in the presence of trimethylaluminum to give the title compound. HR-MS (ES, m/z) calculated for $C_{29}H_{34}N_3O_3SCl_2$ [(M+H)$^+$] 574.1693, observed 574.1589.

EXAMPLE 32 rac-(4S*,5R*)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl chloride

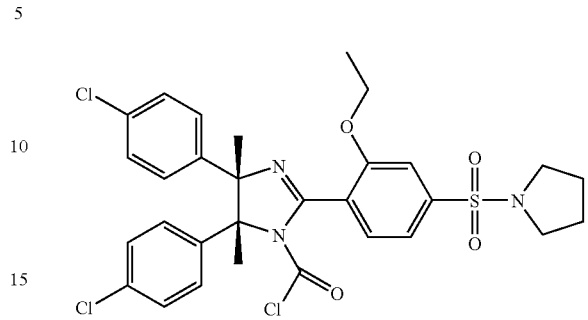

In a manner analogous to the method described in example 3, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-1H-imidazole (example 31) was reacted with phosgene in the presence of triethylamine to give the title compound.

EXAMPLE 33 rac-(4S*,5R*)-2-(4-tert-Butylsulfamoyl-2-ethoxy-phenyl)-4,5-bis-(4-chloro-phenyl)-4,5-dimethyl-4,5-dihydro-imidazole-1-carbonyl chloride

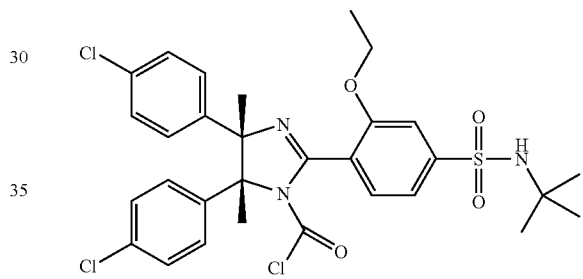

In a manner analogous to the method described in example 3, rac-(4S*,5R*)-4-[(4,5-Bis-(4-chloro-phenyl)-4,5-dimethyl-4,5-dihydro-1H-imidazol-2-yl]-N-tert-butyl-3-ethoxy-benzenesulfonamide (example 32) was reacted with phosgene in the presence of triethylamine to give the title compound.

EXAMPLE 34

{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(3-methanesulfonyl-propyl)-piperazin-1-yl]-methanone

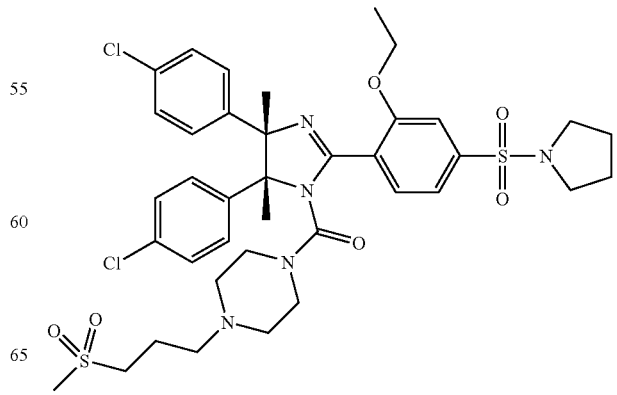

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{38}H_{47}N_6O_5S_2Cl_2$ [(M+H)$^+$] 804.2418, observed 804.2413.

EXAMPLE 35

2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-acetamide

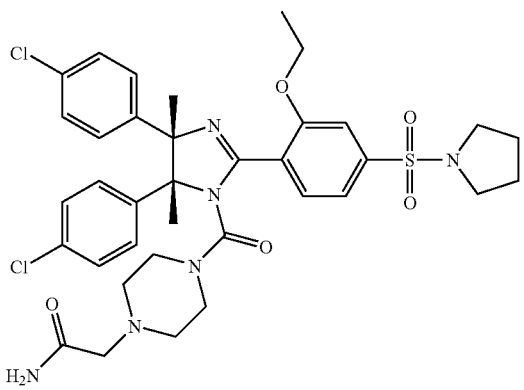

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% of 1:1 ethanol/acetonitrile in carbon dioxide).

HR-MS (ES, m/z) calculated for $C_{36}H_{42}N_6O_5SCl_2$ [(M+H)$^+$] 741.2387, observed 741.2379.

EXAMPLE 36

2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}piperazin-1-yl)-1-pyrrolidin-1-yl-ethanone

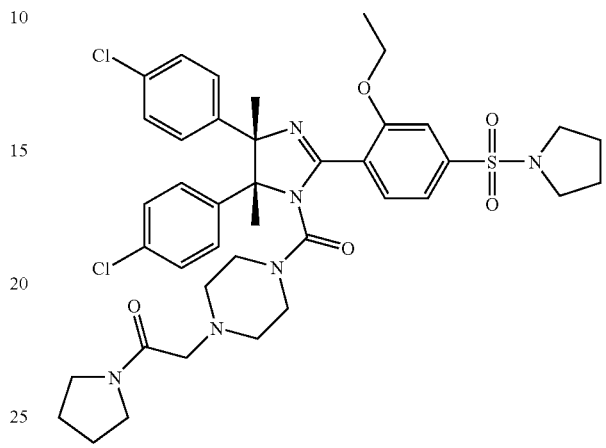

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with 2-piperazin-1-yl-1-pyrrolidin-1-yl-ethanone (Aldrich) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% of 1:1 ethanol/acetonitrile in carbon dioxide). HR-MS (ES, m/z) calculated for $C_{40}H_{48}N_6O_5SCl_2$ [(M+H)$^+$] 795.2857, observed 795.2851.

EXAMPLE 37

N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-methanesulfonamide

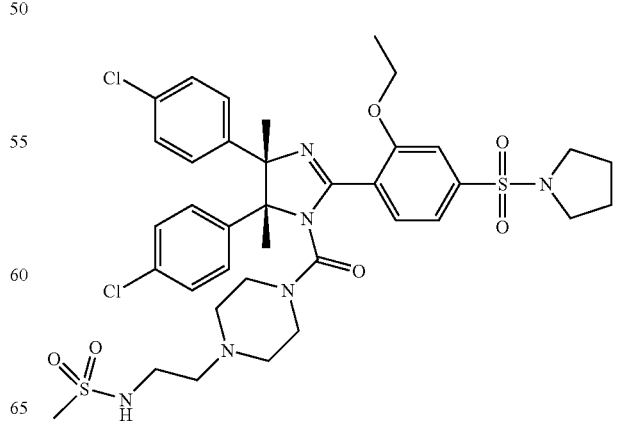

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with N-(2-piperazin-1-yl-ethyl)-methanesulfonamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{37}H_{46}N_6O_6S_2Cl_2$ $[(M+H)^+]$ 805.2370, observed 805.2372.

EXAMPLE 38

N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-acetamide

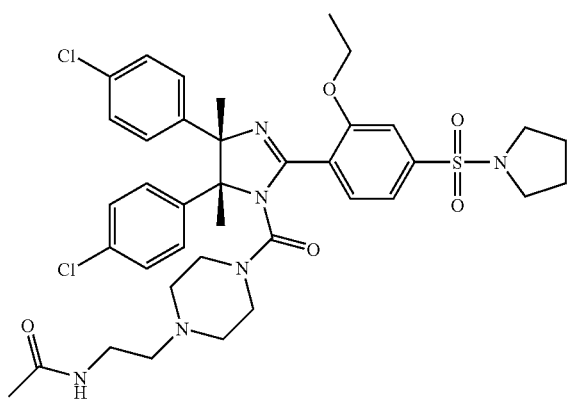

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with N-(2-piperazin-1-yl-ethyl)-acetamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{38}H_{46}N_6O_5SCl_2$ $[(M+H)^+]$ 769.2700, observed 769.2697.

EXAMPLE 39

{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(2-hydroxy-ethyl)-piperazin-1-yl]-methanone

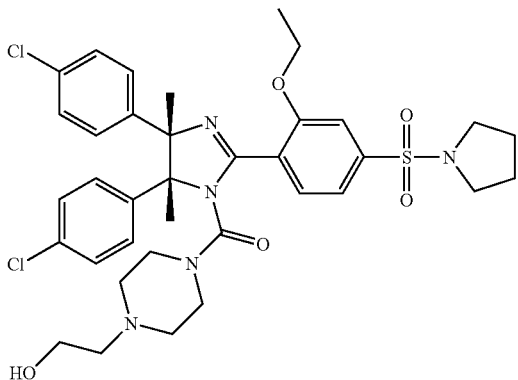

In a manner analogous to the method described in example 5, rac-(4S*,5R*)-4,5-bis-(4-chloro-phenyl)-2-[2-ethoxy-4-(pyrrolidine-1-sulfonyl)-phenyl]-4,5-dimethyl-4,5-dihydro-imidazole-1-carbonyl chloride was reacted with 2-piperazin-1-yl-ethanol (Chemical Dynamics) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{36}H_{43}N_5O_5SCl_2$ $[(M+H)^+]$ 728.2435, observed 728.2431.

EXAMPLE 40

4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-3-ethoxy-benzenesulfonamide

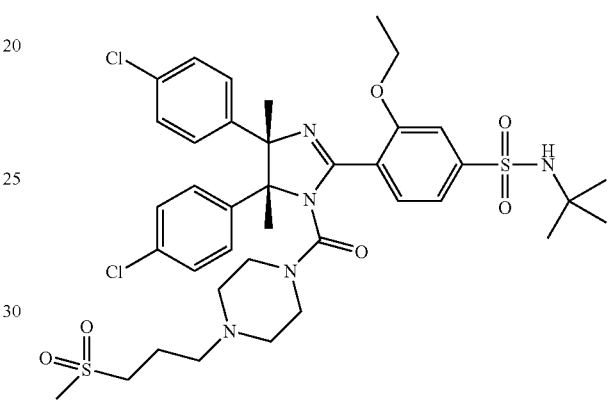

In a manner analogous to the method described in example 5, rac-(4S*,5R*)-2-(4-tert-butylsulfamoyl-2-ethoxy-phenyl)-4,5-bis-(4-chloro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{38}H_{49}N_5O_6S_2Cl_2$ $[(M+H)^+]$ 806.2574, observed 806.2579.

EXAMPLE 41

2-{4-[(4S,5R)-2-(4-tert-Butylsulfamoyl-2-ethoxy-phenyl)-4,5-bis-(4-chloro-phenyl)-4,5-dimethyl-4,5-dihydro-imidazole-1-carbonyl]-piperazin-1-yl}-acetamide

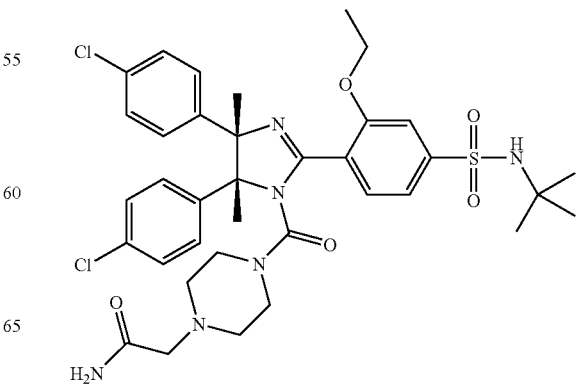

In a manner analogous to the method described in example 5, rac-(4S*,5R*)-2-(4-tert-butylsulfamoyl-2-ethoxy-phenyl)-4,5-bis-(4-chloro-phenyl)-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{36}H_{44}N_6O_5SCl_2$ [(M+H)$^+$] 743.2544, observed 743.2538.

EXAMPLE 42

5-tert-Butylsulfamoyl-4-chloro-2-ethoxybenzoic acid methyl ester

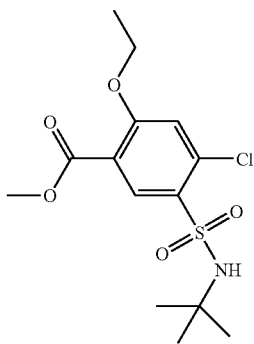

4-Chlorosalicylic acid (15 g, Aldrich, 87.5 mmol) and ethyl iodide (35.7 g, 230 mmol) were dissolved in dimethylformamide (400 mL) and the solution was cooled to 0° C. (acetone-ice bath) with good paddle stirring. Sodium hydride (10.5 g, Aldrich, 50% in oil, 220 mmol) was added in two portions. Cooling was removed after 10 min and the reaction warmed slowly to 30° C. at which point heating was increased to 50-60° C. for 2 h. The reaction was cooled and poured into ice water and extracted into dichloromethane (3×500 mL). The organic layer was washed with water (2×500 mL), washed with brine, dried over magnesium sulfate and evaporated to dryness to give 4-chloro-2-ethoxybenzoic acid ethyl ester.

4-Chloro-2-ethoxybenzoic acid ethyl ester (~18 g) was suspended in ethanol (500 mL). This was treated with potassium hydroxide (200 mL, 2 M solution) and refluxed for 1 h. The reaction was cooled and poured into cold aqueous hydrochloric acid (300 mL, 3 M solution) and extracted into dichloromethane (3×500 mL). The dichloromethane was washed with water (500 mL) and dried over magnesium sulfate and evaporated to dryness to give 4-chloro-2-ethoxy-benzoic acid as a solid.

4-Chloro-2-ethoxybenzoic acid (9.4 g, 47 mmol) was added in several portions to cold chlorosulfonic acid (55 mL, Aldrich) stirring at 0-10° C., and the resulting solution was heated at ~60° C. for 2 h. The resulting dark solution was poured into ice (800 g), and then 500 mL of dichloromethane was added. After stirring for 15 min, the layers were separated and the aqueous layer was extracted with 200 mL of dichloromethane. The organic layers were washed in turn with brine, combined, dried over magnesium sulfate, filtered, and concentrated at room temperature. Crystallization from ether/hexane gave 3.4 g of 4-chloro-5-chlorosulfonyl-2-ethoxy-benzoic acid.

A solution of 4-chloro-6-chlorosulfonyl-2-ethoxybenzoic acid (1.0 g, 3.34 mmol) and tert-butyl amine (2.0 mL) in 20 mL of tetrahydrofuran was refluxed for 4 h and concentrated. The residue in water was acidified and extracted with ether, the extract was washed with water, brine, dried over magnesium sulfate, filtered and evaporated. Precipitation from ether/hexane provided 0.8 g of crude 5-tert-butylsulfamoyl-4-chloro-2-ethoxybenzoic acid.

5-tert-Butylsulfamoyl-4-chloro-2-ethoxybenzoic acid (0.8 g, 24 mmol) in 10 mL of tetrahydrofuran was treated with diazomethane (15 mL, ~2-3 M in ether, prepared from N-methyl-N-nitroso-p-toluenesulfonamide, Aldrich) at room temperature and stirred for 0.5 h. The mixture was concentrated, and the residue was purified by flash chromatography (silica gel, eluting with 20% ethyl acetate in hexane) to give 0.45 g of 5-tert-butylsulfamoyl-4-chloro-2-ethoxybenzoic acid methyl ester as a solid.

EXAMPLE 43 rac-(4S*,5R*)-5-[4,5-Bis-(4-chlorophenyl)-4,5-dimethyl-4,5-dihydro-1H-imidazol-2-yl]-N-tert-butyl-2-chloro-4-ethoxybenzenesulfonamide

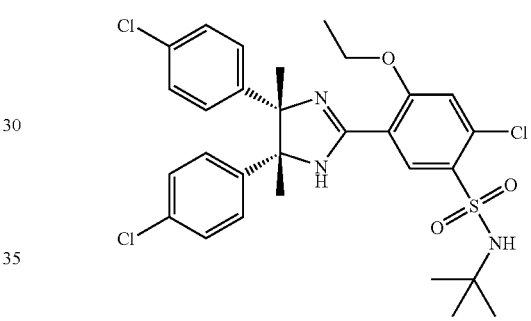

In a manner analogous to the method described in example 2, meso-2,3-bis-(4-chlorophenyl)-2,3-butanediamine (example 1) was reacted with 5-tert-butylsulfamoyl-4-chloro-2-ethoxybenzoic acid methyl ester (example 43) in the presence of trimethylaluminum to give the title compound. HR-MS (ES, m/z) calculated for $C_{29}H_{33}N_3O_3SCl_3$ [(M+H)$^+$] 608.1303, observed 608.1300.

EXAMPLE 44 rac-(4S*,5R*)-2-(5-tert-Butylsulfamoyl-4-chloro-2-ethoxyphenyl)-4,5-bis-(4-chlorophenyl)-4,5-dimethyl-4,5-dihydroimidazole-1-carbonyl chloride

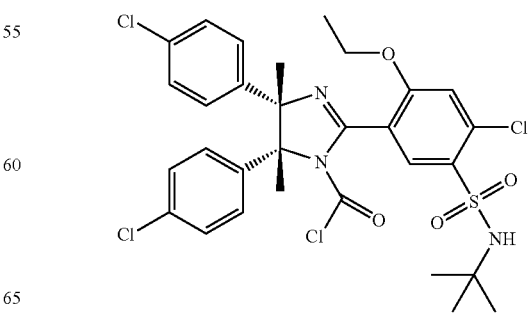

In a manner analogous to the method described in example 3, rac-(4S*,5R*)-5-[4,5-bis-(4-chlorophenyl)-4,5-dimethyl-4,5-dihydro-1H-imidazol-2-yl]-N-tert-butyl-2-chloro-4-ethoxybenzene-sulfonamide (example 44) was reacted with phosgene in the presence of triethylamine to give the title compound.

EXAMPLE 45
5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-2-chloro-4-ethoxy-benzenesulfonamide

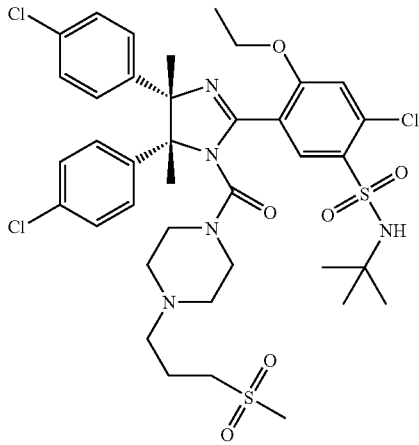

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (260 mg, 0.39 mmol, example 45) and triethylamine (350 mg, 3.34 mmol) in methylene chloride (10 mL) was treated with 1-(3-methanesulfonyl-propyl)-piperazine dihydrochloride (110 mg, 0.39 mmol, prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{38}H_{49}N_5O_6S_2Cl_3$ [(M+H)$^+$] 840.2185, observed 840.2179

EXAMPLE 46
5-{(4S,5R)-4,5-Bis-(4-chlorophenyl)-1-[4-(2-methanesulfonylaminoethyl)piperazine-1-carbonyl]-4,5-dimethyl-4,5-dihydro-1H-imidazol-2-yl}-N-tert-butyl-2-chloro-4-ethoxybenzenesulfonamide

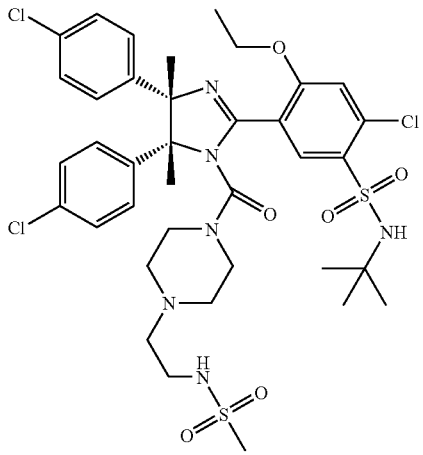

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with N-(2-piperazin-1-yl-ethyl)-methanesulfonamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{37}H_{48}N_6O_6S_2Cl_3$ [(M+H)$^+$] 841.2137, observed 841.2129.

EXAMPLE 47
N-{(4S,5R)-(2-{4-[2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}ethyl)acetamide

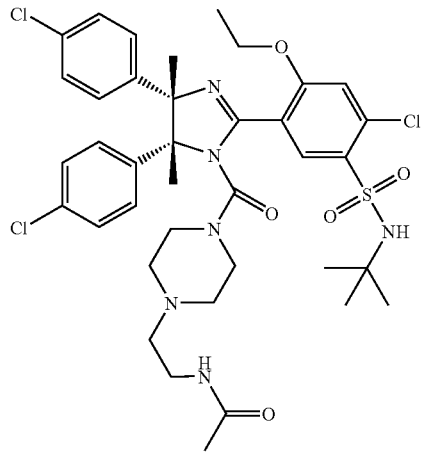

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with N-(2-piperazin-1-yl-ethyl)-acetamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{37}H_{48}N_6O_5SCl_3$ [(M+H)$^+$] 805.2460, observed 805.2467.

EXAMPLE 48

5-{(4S,5R)-4,5-Bis-(4-chlorophenyl)-1-[4-(2-hydroxyethyl)piperazine-1-carbonyl]-4,5-dimethyl-4,5-dihydro-1H-imidazol-2-yl}-N-tert-butyl-2-chloro-4-ethoxybenzenesulfonamide

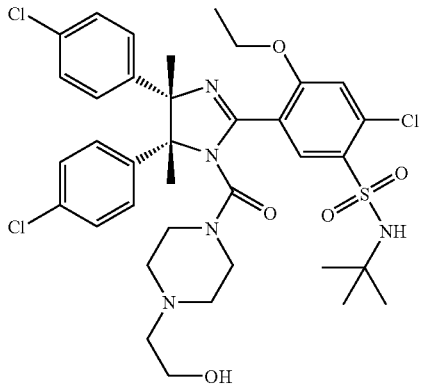

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with 2-piperazin-1-yl-ethanol (Chemical Dynamics) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{36}H_{45}N_5O_5SCl_3$ $[(M+H)^+]$ 764.2202, observed 764.2198.

EXAMPLE 49

5-{(4S,5R)-4,5-Bis-(4-chlorophenyl)-4,5-dimethyl-1-[4-(2-oxo-2-pyrrolidin-1-yl-ethyl)-piperazine-1-carbonyl]-4,5-dihydro-1H-imidazol-2-yl}-N-tert-butyl-2-chloro-4-ethoxybenzenesulfonamide

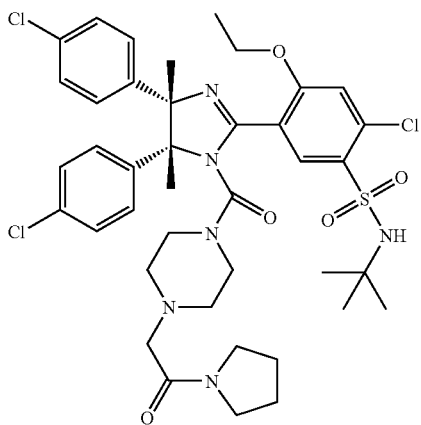

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with 2-piperazin-1-yl-1-pyrrolidin-1-yl-ethanone (Aldrich) to give the title compound as a racemic mixture. The enantiomers were then separated by supercritical fluid chromatography (Berger Instrument Multi-Gram II, Daicel ChiralPak OJ-H 3×25 cm, 35° C. at 100 bar, eluting with 15% methanol in carbon dioxide). HR-MS (ES, m/z) calculated for $C_{40}H_{50}N_6O_5SCl_3$ $[(M+H)^+]$ 831.2624, observed 831.2625.

EXAMPLE 50

2-{4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}-acetamide

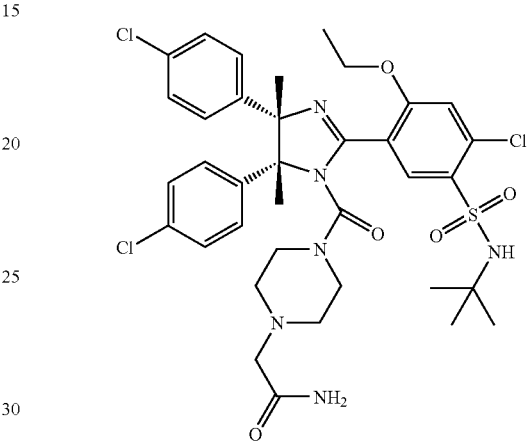

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% of 1:1 acetonitrile/ethanol in carbon dioxide). HR-MS (ES, m/z) calculated for $C_{36}H_{44}N_6O_5SCl_3$ $[(M+H)^+]$ 777.2154, observed 777.2146.

EXAMPLE 51

(S)-4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-1-methylpiperazine-2-carboxylic acid methyl ester

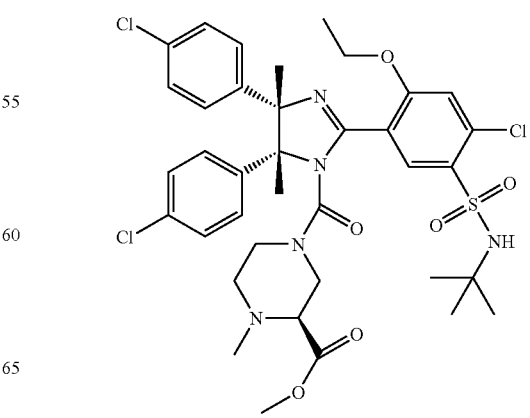

In a manner analogous to the method described in example 5, rac-(4S*,5R*)-2-(5-tert-butylsulfamoyl-4-chloro-2-ethoxy-phenyl)-4,5-bis-(4-chloro-phenyl)-4,5-dimethyl-4,5-dihydro-imidazole-1-carbonyl chloride (example 45) was reacted with (S)-1-methyl-piperazine-2-carboxylic acid methyl ester to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{37}H_{45}N_5O_6SCl_3$ [(M+H)$^+$] 792.2151, observed 792.2148.

EXAMPLE 52 rac-(4S*,5R*)-2-[4-Chloro-2-ethoxy-5-(pyrrolidine-1-sulfonyl)phenyl]-4,5-bis-(4-chlorophenyl)-4,5-dimethyl-4,5-dihydro-1H-imidazole

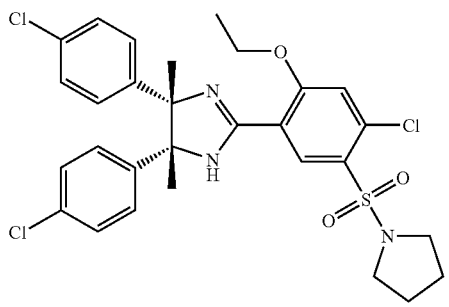

In a manner analogous to the method described in example 2, meso-2,3-bis-(4-chlorophenyl)-2,3-butanediamine (example 1) was reacted with 4-chloro-2-ethoxy-5-(pyrrolidine-1-sulfonyl)benzoic acid methyl ester (prepared in an analogous manner as described in example 43) in the presence of trimethylaluminum to give the title compound. HR-MS (ES, m/z) calculated for $C_{29}H_{33}N_3O_3SCl_3$ [(M+H)$^+$] 608.1303, observed 608.1300.

EXAMPLE 53 rac-(4S*,5R*)-[-2-[4-Chloro-2-ethoxy-5-(pyrrolidine-1-sulfonyl)phenyl]-4,5-bis-(4-chlorophenyl)-4,5-dimethyl-4,5-dihydroimidazole-1-carbonyl chloride

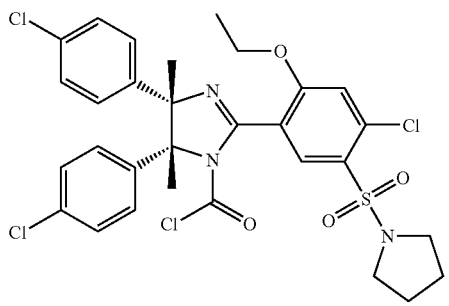

In a manner analogous to the method described in example 3, rac-(4S*,5R*)-2-[4-chloro-2-ethoxy-5-(pyrrolidine-1-sulfonyl)phenyl]-4,5-bis-(4-chlorophenyl)-4,5-dimethyl-4,5-dihydro-1H-imidazole (example 53) was reacted with phosgene in the presence of triethylamine to give the title compound.

EXAMPLE 54

5-{(4S,5R)-2-[4-Chloro-2-ethoxy-5-(pyrrolidine-1-sulfonyl)phenyl]-4,5-bis-(4-chloro-phenyl)-4,5-dimethyl-4,5-dihydroimidazol-1-yl]-[4-(3-methanesulfonylpropyl)-piperazin-1-yl]methanone

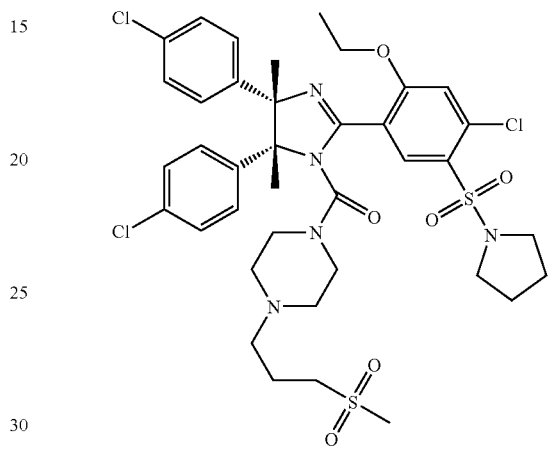

In a manner analogous to the method described in example 5, rac-(4S*,5R*)-2-[4-chloro-2-ethoxy-5-(pyrrolidine-1-sulfonyl)-phenyl]-4,5-bis-(4-chloro-phenyl)-4,5-dimethyl-4,5-dihydro-imidazole-1-carbonyl chloride (example 54) was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{38}H_{47}N_5O_6S_2Cl_3$ [(M+H)$^+$] 838.2028, observed 838.2025.

EXAMPLE 55

2-Ethoxy-4-methoxy-5-(pyrrolidine-1-sulfonyl)benzoic acid methyl ester

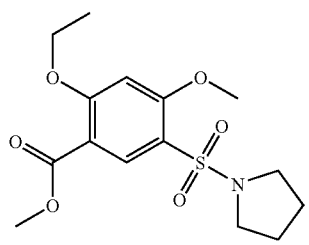

4-Methoxysalicylic acid (10 g, 59 mmol, Aldrich) and ethyl iodide (23.2 g, 150 mmol, Aldrich) were dissolved in dimethylformamide (300 mL) and the solution was cooled to 0° C. (ice bath) with good paddle stirring. Sodium hydride (6.2 g, 130 mmol, 50% in mineral oil, Aldrich) was added in two portions. The ice bath was removed after 10 min, and the reaction was warmed slowly to 30° C. at which point heating was applied to increase the temperature to 50-60° C. After 2 h, the reaction was cooled and poured into ice water and extracted into dichloromethane (2×500 mL). The organic layer was washed with water (2×500 mL), brine and dried over anhydrous magnesium sulfate. The solids were filtered off, and the filtrate was evaporated to dryness to give 2-ethoxy-4-methoxybenzoic acid ethyl ester.

2-Ethoxy-4-methoxybenzoic acid ethyl ester (13 g, 58 mmol) was suspended in ethanol (150 mL). This was treated with potassium hydroxide (40 mL, ~4 M) and refluxed for 1 h. The reaction was cooled and poured into cold aqueous hydrochloric acid (300 mL, 2 M) and extracted into dichloromethane (3×200 mL). The organic layers were washed with brine and dried over anhydrous magnesium sulfate. The solids were filtered off, and the filtrate was evaporated to dryness to give 2-ethoxy-4-methoxybenzoic acid (9.5 g, white solid).

2-Ethoxy-4-methoxybenzoic acid (9.5 g, 48.5 mmol) was added in portions to cold chlorosulfonic acid (60 mL, Aldrich) stirring at −3 to 0° C. (ice-acetone bath) over 15 min and warmed slowly to room temperature and heated to 60-65° C. for 40 min. The resulting dark solution was carefully poured with stirring into a large excess of ice and then 500 mL of dichloromethane was added. After stirring for 15 min, the layers were separated and the aqueous layer was extracted with dichloromethane (3×250 mL). The organic layers were washed with brine and dried over anhydrous magnesium sulfate. The solids were filtered off, and the filtrate was evaporated to a low volume. This was triturated with ether/hexane and filtered to give 5-chlorosulfonyl-2-ethoxy-4-methoxybenzoic acid as a colorless solid (13.4 g, 94%).

A solution of 5-chlorosulfonyl-2-ethoxy-4-methoxybenzoic acid (13 g, 44 mmol) in tetrahydrofuran was cooled to 5° C. and treated with excess diazomethane in ether solution (prepared from N-methyl-N-nitroso-p-toluenesulfonamide, Aldrich) and stirred for 10 min. Solvent and excess diazomethane was removed by rotary evaporation. The resulting residue was dissolved in dichloromethane and filtered through a plug of silica gel and evaporated. The solids were triturated with ether/hexane to give 13 g of 5-chlorosulfonyl-2-ethoxy-4-methoxy-benzoic acid methyl ester as a colorless solid.

In a manner analogous to the method described in example 33, 5-chlorosulfonyl-2-ethoxy-4-methoxy-benzoic acid methyl ester was reacted with pyrrolidine to give the title compound.

EXAMPLE 56 rac-(4S*,5R*)-4,5-Bis-(4-chlorophenyl)-2-[2-ethoxy-4-methoxy-5-(pyrrolidine-1-sulfonyl)phenyl]-4,5-dimethyl-4,5-dihydro-1H-imidazole

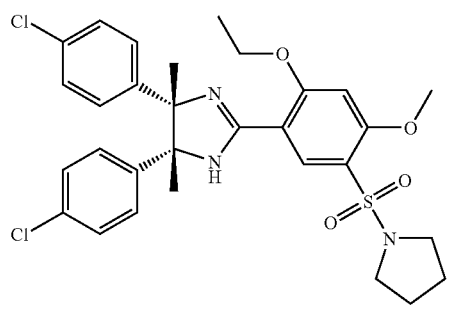

In a manner analogous to the method described in example 2, meso-2,3-bis-(4-chlorophenyl)-2,3-butanediamine was reacted with 2-ethoxy-4-methoxy-5-(pyrrolidine-1-sulfonyl) benzoic acid methyl ester in the presence of trimethylaluminum to give the title compound. LR-MS: 602 (M+H)+.

EXAMPLE 57 rac-(4S*,5R*)-4,5-Bis-(4-chlorophenyl)-2-[2-ethoxy-4-methoxy-5-(pyrrolidine-1-sulfonyl)-phenyl]-4,5-dimethyl-4,5-dihydroimidazole-1-carbonyl chloride

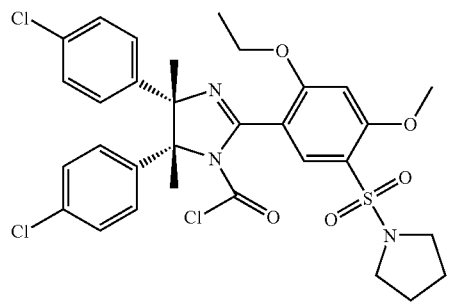

In a manner analogous to the method described in example 3, rac-(4S*,5R*)-4,5-bis-(4-chlorophenyl)-2-[2-ethoxy-4-methoxy-5-(pyrrolidine-1-sulfonyl)phenyl]-4,5-dimethyl-4,5-dihydro-1H-imidazole was reacted with phosgene in the presence of triethylamine to give the title compound.

EXAMPLE 58

{(4S,5R)-4,5-Bis-(4-chlorophenyl)-2-[2-ethoxy-4-methoxy-5-(pyrrolidine-1-sulfonyl)-phenyl]-4,5-dimethyl-4,5-dihydroimidazol-1-yl}-[4-(3-methanesulfonylpropyl)-piperazin-1-yl]methanone

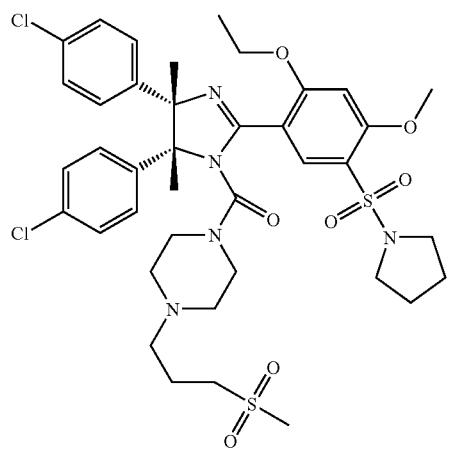

In a manner analogous to the method described in example 5, rac-(4S*,5R*)-4,5-bis-(4-chlorophenyl)-2-[2-ethoxy-4-methoxy-5-(pyrrolidine-1-sulfonyl)-phenyl]-4,5-dimethyl-4,5-dihydroimidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{39}H_{50}N_5O_7S_2Cl_2$ [(M+H)$^+$] 834.2523, observed 834.2524.

EXAMPLE 59

4-Chloro-2-ethoxy-5-methanesulfonyl-benzoic acid methyl ester

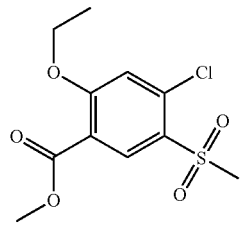

To a solution of sodium bicarbonate (5.0 g, 60 mmol) and sodium sulfite (2.4 g, 19 mmol) in water (25 mL) at 70-75° C. was treated with 4-chloro-5-chlorosulfonyl-2-ethoxy-benzoic acid (6.2 g, 21 mmol, example 43) in portions according to the procedure described by Imamura, S. et al. (*Bioorg. Med. Chem.* 2005, 13, 397-416). After 1 h at 75° C., chloroacetic acid (3.0 g, 32 mmol) was carefully added in three portions followed by a solution of aqueous sodium hydroxide (1.28 g, 32 mmol/4 mL water) and stirred at 100° C. for 16 h. This was cooled and poured into 2N hydrochloric acid (100 mL) and extracted with ethyl acetate (2×) The organic extracts were washed with brine, dried over magnesium sulfate, filtered, and concentrated at room temperature to a low volume. This was triturated with ether and filtered to give 4-chloro-2-ethoxy-5-methanesulfonyl-benzoic acid methyl ester as a colorless solid (5.2 g, 89%).

A solution of 4-chloro-2-ethoxy-5-methanesulfonylbenzoic acid (2.5 g, 9.0 mmol) in tetrahydrofuran was cooled to 5° C. and treated with excess diazomethane in ether solution (prepared from N-methyl-N-nitroso-p-toluenesulfonamide, Aldrich) and stirred for 10 min. Solvent and excess diazomethane was removed by rotary evaporation. The resulting residue was dissolved in dichloromethane and filtered through a plug of silica gel and evaporated. The solids were triturated with ether/hexane to give 4-chloro-2-ethoxy-5-methanesulfonyl-benzoic acid methyl ester (2.1 g, colorless solids).

EXAMPLE 60 rac-(4S*,5R*)-2-(4-Chloro-2-ethoxy-5-methanesulfonylphenyl)-4,5-bis-(4-chlorophenyl)-4,5-dimethyl-4,5-dihydro-1H-imidazole

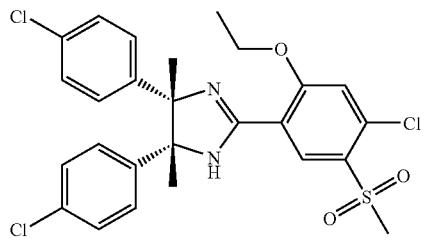

In a manner analogous to the method described in example 2, meso-2,3-bis-(4-chlorophenyl)-2,3-butanediamine was reacted with 4-chloro-2-ethoxy-5-methanesulfonyl-benzoic acid methyl ester in the presence of trimethylaluminum to give the title compound. HR-MS (ES, m/z) calculated for $C_{26}H_{26}N_2O_3SCl_3$ [(M+H)$^+$] 551.0724, observed 551.0721.

EXAMPLE 61 rac-(4S*,5R*)-2-(4-Chloro-2-ethoxy-5-methanesulfonyl-phenyl)-4,5-bis-(4-chloro-phenyl)-4,5-dimethyl-4,5-dihydro-imidazole-1-carbonyl chloride

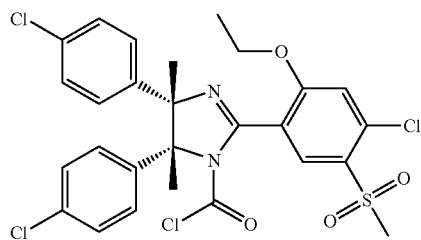

In a manner analogous to the method described in example 3, rac-(4S*,5R*)-2-(4-chloro-2-ethoxy-5-methanesulfonyl-phenyl)-4,5-bis-(4-chloro-phenyl)-4,5-dimethyl-4,5-dihydro-1H-imidazole was reacted with phosgene in the presence of triethylamine to give the title compound.

EXAMPLE 62

[(4S,5R)-2-(4-Chloro-2-ethoxy-5-methanesulfonyl-phenyl)-4,5-bis-(4-chlorophenyl)-4,5-dimethyl-4,5-dihydroimidazol-1-yl]-[4-(3-methanesulfonylpropyl)-piperazin-1-yl]methanone

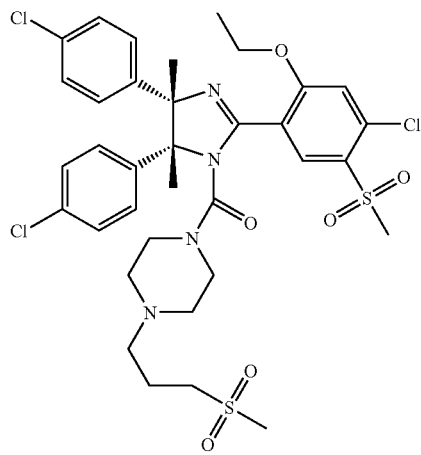

In a manner analogous to the method described in example 5, 2-(4-chloro-2-ethoxy-5-methanesulfonylphenyl)-4,5-bis-(4-chlorophenyl)-4,5-dimethyl-4,5-dihydroimidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% of 1:1 ethanol/acetonitrile in carbon dioxide). HR-MS (ES, m/z) calculated for $C_{35}H_{42}N_4O_6S_2Cl_3$ [(M+H)$^+$] 783.1606, observed 783.1596

EXAMPLE 63

2-Ethoxy-5-(pyrrolidine-1-sulfonyl)benzoic acid ethyl ester

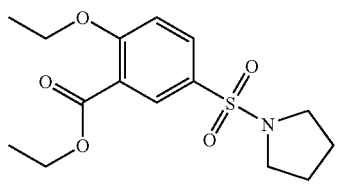

A solution of 5-chlorosulfonyl-2-hydroxybenzoic acid (0.52 g, 2.0 mmol, Matrix Scientific) in tetrahydrofuran (10 mL) was treated with pyrrolidine (1.5 g, 21 mmol) and refluxed for 2 h. This was cooled and poured into dilute aqueous hydrochloric acid and extracted into dichloromethane (2×50 mL). The combined extracts were washed with brine, dried over magnesium sulfate, filtered, and concentrated to give a solid. This was triturated with ether to give 2-hydroxy-5-(pyrrolidine-1-sulfonyl)benzoic acid as a solid. It was then converted to 2-ethoxy-5-(pyrrolidine-1-sulfonyl) benzoic acid ethyl ester In a manner analogous to the method described in example 33.

EXAMPLE 64 rac-(4S*,5R*)-4,5-Bis-(4-chlorophenyl)-2-[2-ethoxy-5-(pyrrolidine-1-sulfonyl)phenyl]-4,5-dimethyl-4,5-dihydro-1H-imidazole

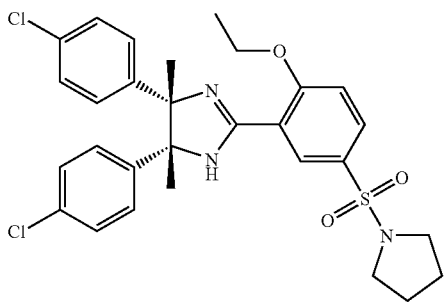

In a manner analogous to the method described in example 2, meso-2,3-bis-(4-chlorophenyl)-2,3-butanediamine was reacted with 2-ethoxy-5-(pyrrolidine-1-sulfonyl)benzoic acid ethyl ester in the presence of trimethylaluminum to give the title compound.

EXAMPLE 65 rac-(4S*,5R*)-4,5-Bis-(4-chlorophenyl)-2-[2-ethoxy-5-(pyrrolidine-1-sulfonyl)phenyl]-4,5-dimethyl-4,5-dihydroimidazole-1-carbonyl chloride

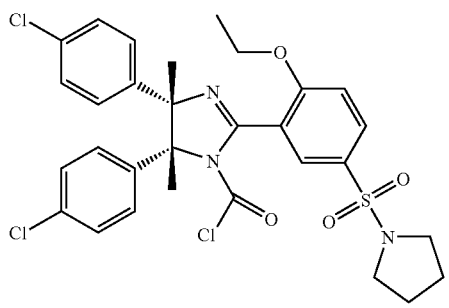

In a manner analogous to the method described in example 3, rac-(4S*,5R*)-4,5-bis-(4-chlorophenyl)-2-[2-ethoxy-5-(pyrrolidine-1-sulfonyl)phenyl]-4,5-dimethyl-4,5-dihydro-1H-imidazole was reacted with phosgene in the presence of triethylamine to give the title compound.

EXAMPLE 66

{(4S,5R)-4,5-Bis-(4-chlorophenyl)-2-[2-ethoxy-5-(pyrrolidine-1-sulfonyl)phenyl]-4,5-dimethyl-4,5-dihydroimidazol-1-yl}-[4-(3-methanesulfonylpropyl)-piperazin-1-yl]methanone

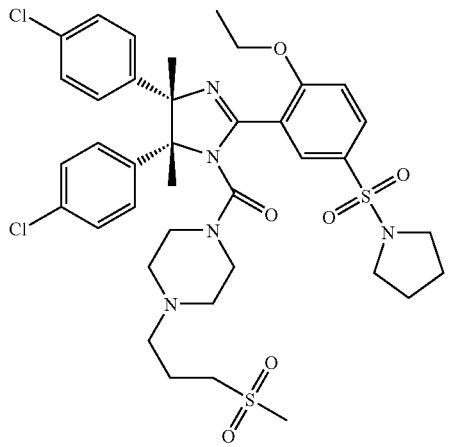

In a manner analogous to the method described in example 5, rac-(4S*,5R*)-4,5-bis-(4-chloro-phenyl)-2-[2-ethoxy-5-(pyrrolidine-1-sulfonyl)-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{38}H_{48}N_5O_6S_2Cl_2$ [(M+H)$^+$] 804.2418, observed 804.2413

EXAMPLE 67

4-Cyano-2-ethoxybenzoic acid methyl ester

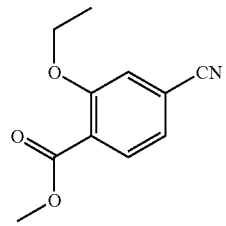

2-Ethoxy-4-nitrobenzoic acid (20 g, 94 mmol, Aldrich) was suspended in ethanol (170 mL) and combined with a saturated aqueous solution of ammonium chloride (100 mL). As this was rapidly stirred, iron dust (13.3 g, 239 mmol) was added in portions. The temperature was raised to 80° C. for 1 h. The cooled suspension was filtered through Celite, and the cake washed with dichloromethane (150 mL). The filtrate was diluted with dichloromethane and washed with brine, dried over magnesium sulfate, filtered and evaporated. A brown solid was triturated with dichloromethane and filtered to give 15 g of 4-amino-2-ethoxybenzoic acid (88%).

A suspension 4-amino-2-ethoxybenzoic acid (20 g, 110 mmol) in 2N hydrochloric acid (200 mL) was well stirred with ice bath cooling. To this was added sodium nitrite (7.68 g, 111 mmol) in 22 mL of water. After stirring for 5 min, solid sodium carbonate was added to adjust the pH to 9-10. Separately, copper chloride (14.2 g, 143 mmol) in 200 mL water was slowly added to a solution of sodium cyanide ((18.28 g, 371 mmol) in 200 mL water at 0-5° C. and stirred for 2 h. The cold nitrite solution was added slowly to the cyanide solution and stirred at 0-5° C. for 15 min, followed by 25° C. for 2 h. This was filtered and the aqueous solution was adjusted to pH 2 with concentrated hydrochloric acid. This was extracted with ethyl acetate (4 L). The organic extracts were washed with brine and dried over anhydrous magnesium sulfate. The solids were filtered off, and the filtrate was concentrated to give 19 g of crude 4-cyano-2-ethoxybenzoic acid.

Crude 4-cyano-2-ethoxybenzoic acid (19 g) was dissolved in a mixture of benzene (446 mL) and methanol (111 mL). At 0° C., (trimethylsilyl)diazomethane (76 mL, 2.0 M in ether, Aldrich) was added slowly and then at room temperature. Solvent was removed, and the residue was purified by flash chromatography (silica gel, eluting with 25% ethyl acetate in hexane) to give 4-cyano-2-ethoxybenzoic acid methyl ester as a solid (15.5 g, 74%).

EXAMPLE 68 rac-4-[(4S*,5R*)-4,5-Bis-(4-chloro-phenyl)-4,5-dimethyl-4,5-dihydro-1H-imidazol-2-yl]-3-ethoxybenzonitrile

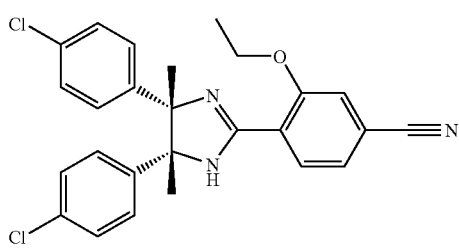

In dry toluene (6 mL) was added trimethylaluminum (0.7 mL, 0.14 mmol, 2.0 M in toluene, Aldrich). At 0° C., meso-2,3-bis-(4-chlorophenyl)-butane-2,3-diamine (0.28 g, 0.091 mmol) in toluene (7 mL) was added over 10 min. This was warmed to room temperature for 1 h. 4-Cyano-2-ethoxybenzoic acid methyl ester (0.34 g, 0.166 mmol) suspended in toluene (6 mL) was added and the mixture was raised to reflux for 16 h. The reaction was cooled and 3 mL of Rochelle salt was added and stirred for 2 h. The reaction was diluted with ethyl acetate (20 mL) and stirred for 10 min. The organic layer was separated, dried over magnesium sulfate, filtered and evaporated. Purification of the residue by flash chromatography (silica gel, eluting with 20-50% ethyl acetate/hexane) gave 250 mg of the title compound.

EXAMPLE 69

4-{(4S,5R)-4,5-Bis-(4-chlorophenyl)-1-[4-(3-methanesulfonylpropyl)-piperazine-1-carbonyl]-4,5-dimethyl-4,5-dihydro-1H-imidazol-2-yl}-3-ethoxybenzonitrile

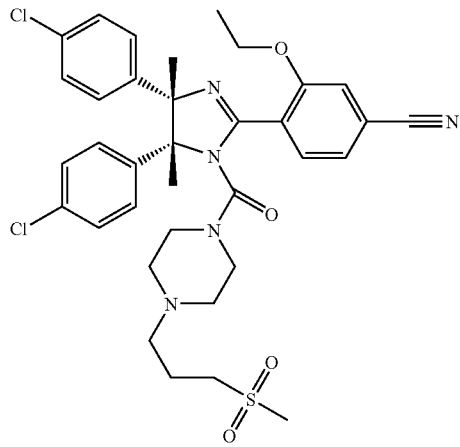

A solution of rac-4-[(4S*,5R*)-4,5-bis-(4-chloro-phenyl)-4,5-dimethyl-4,5-dihydro-1H-imidazol-2-yl]-3-ethoxy-benzonitrile (190 mg, 0.31 mmol) in dichloromethane was cooled to 0° C. and treated with phosgene (2.5 mL, 0.47 mmol, 1.9 M in toluene) and triethylamine (0.66 g, 0.65 mmol). After 1 h, the reaction was charged with the same quantities of phosgene and triethylamine. After an additional 1 h at 0° C., the reaction was worked up in ice water and dichloromethane. The organic layer was dried over anhydrous magnesium sulfate, filtered and evaporated to give an oil. It was purified by a short plug of silica gel (eluting with 20% ethyl acetate/hexane) to give rac-(4S*,5R*)-4,5-bis-(4- chloro-phenyl)-2-(4-cyano-2-ethoxy-phenyl)-4,5-dimethyl-4,5-dihydro-imidazole-1-carbonyl chloride.

A solution of rac-(4S*,5R*)-4,5-bis-(4-chloro-phenyl)-2-(4-cyano-2-ethoxy-phenyl)-4,5-dimethyl-4,5-dihydro-imidazole-1-carbonyl chloride (~175 mg, 0.26 mmol) in dichloromethane (10 mL) and triethylamine (0.35 g, 3.34 mmol) at 0° C. was treated with 1-(3-methanesulfonylpropyl)piperazine (0.11 g, 0.39 mmol, prepared as described in Fotouhi, N. et a. WO 2005110996) for 0.5 h. The reaction was washed with cold water, dried over anhydrous magnesium sulfate, filtered and evaporated to give a solid. Trituration with ether and filtration gave the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{35}H_{40}N_5O_4SCl_2$ [(M+H)$^+$] 696.2173, observed 696.2167.

EXAMPLE 70

[(4S,5R)-2-(4-tert-Butyl-2-ethoxy-phenyl)-4,5-bis-(4-chloro-phenyl)-4,5-dimethyl-4,5-dihydro-imidazol-1-yl]-piperazin-1-yl-methanone

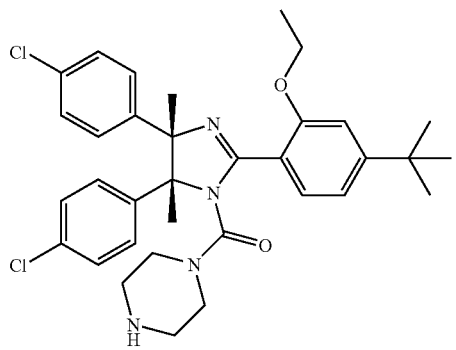

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with piperazine (Aldrich) to give the title compound. HR-MS (ES, m/z) calculated for $C_{34}H_{41}N_4O_2Cl_2$ [(M+H)$^+$] 607.2601, observed 607.2603.

EXAMPLE 71

1-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethanone

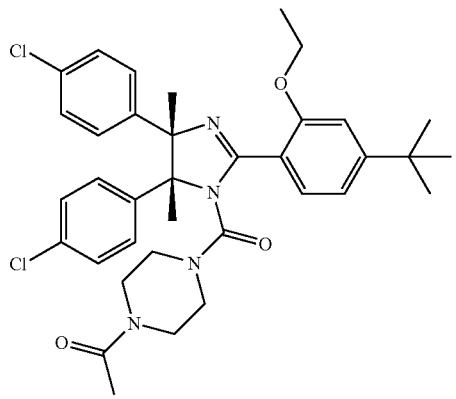

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with 1-acetyl-piperazine (Aldrich) to give the title compound. LR-MS: 649.2 [(M+H)$^+$]

EXAMPLE 72

N-tert-Butyl-2-{4-[(4S,5R)-2-(4-tert-butyl-2-ethoxy-phenyl)-4,5-bis-(4-chloro-phenyl)-4,5-dimethyl-4,5-dihydro-imidazole-1-carbonyl]-piperazin-1-yl}-acetamide

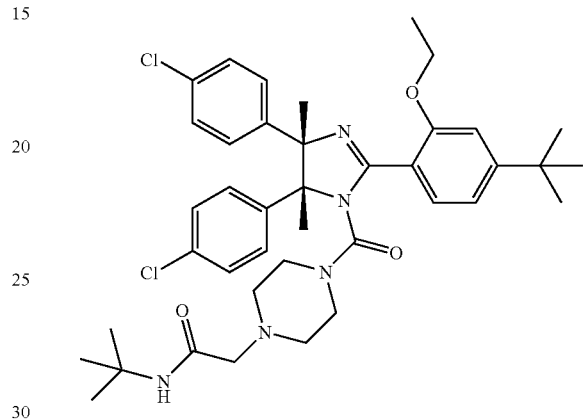

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-imidazole-1-carbonyl chloride (example 4) was reacted with N-tert-butyl-2-piperazin-1-yl-acetamide (Enamine-BB) to give the title compound.

EXAMPLE 73

4-Bromo-2-ethoxy-benzoic acid ethyl ester

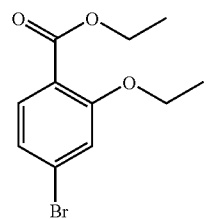

Sodium (1.815 g, 78.9 mmol, Aldrich) was cut into small pieces and added to ethanol (100 mL). After all the pieces were dissolved, the clear solution was added to a solution of ethyl 4-bromo-2-fluoro-benzoate (13 g, 52.6 mmol) in ethanol (20 mL) cooled to 0° C. The ice bath was then removed and the mixture was stirred at room temperature for 12 h. The reaction mixture was concentrated in vacuo, and the residue was taken in water and 20% ethyl acetate-hexane. The organic layer was washed with saturated solution of sodium bicarbonate, brine, and dried over anhydrous sodium sulfate. The solids were filtered off, and the filtrate was concentrated in vacuo. Purification of the crude residue by flash chromatography (120 g of silica gel, eluting with 10-15% ethyl acetate in hexane) gave 4-bromo-2-ethoxy-benzoic acid ethyl ester as white solids (11.020 g, 77%).

EXAMPLE 74 rac-(4S*,5R*)-2-(4-Bromo-2-ethoxy-phenyl)-4,5-bis-(4-chloro-phenyl)-4,5-dimethyl-4,5-dihydro-1H-imidazole

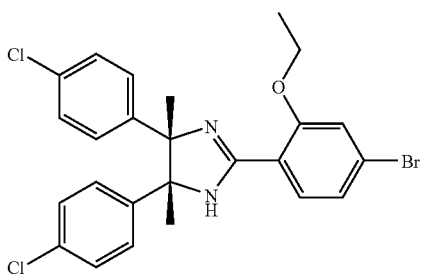

To a solution of meso-2,3-bis-(4-chlorophenyl)-2,3-butanediamine (3 g, example 1) in toluene cooled to 0° C. was added dropwise 2 M solution of trimethylaluminum in toluene (5.33 mL, 10.66 mmol). After the addition, the mixture was stirred at 0° C. for 15 min then the ice bath was removed. After 30 min, the mixture was warmed up to 80-100° C. for about 30 min before being slowly cooled down to room temperature. At room temperature, a solution of 4-bromo-2-ethoxy-benzoic acid ethyl ester (3.18 g, 11.64 mmol) in toluene (10 mL) was added, and the yellow reaction mixture was heated at reflux for 48 h. Upon cooling to room temperature, 1 M Rochelle solution (~20 mL) and ethyl acetate (~50 mL) were added. The biphasic mixture was stirred rigorously at room temperature for 3 h. The layers were separated and the aqueous layer was extracted with ethyl acetate (1×100 mL). The combined organic layers were washed with saturated solution of sodium bicarbonate (1×20 mL), brine (1×20 mL), dried over anhydrous sodium sulfate. The solids were filtered off and the filtrate was concentrated to dryness. Purification of the crude residue by flash chromatography (120 g of silica gel, eluting with 5-10%, 20%, 40% then 80% ethyl acetate in hexane) gave the title compound as light yellow foam (3.25 g, 65%). HR-MS (ES, m/z) calculated for $C_{25}H_{24}N_2OCl_2Br$ [(M+H)$^+$] 517.0444, observed 517.0443.

EXAMPLE 75 rac-(4S*,5R*)-2-(4-Bromo-2-ethoxy-phenyl)-4,5-bis-(4-chloro-phenyl)-4,5-dimethyl-4,5-dihydro-imidazole-1-carbonyl chloride

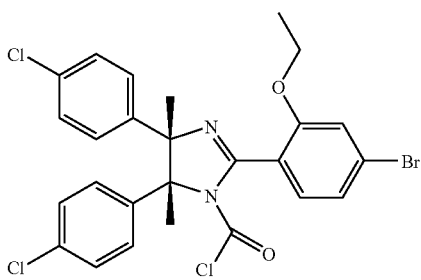

In a manner analogous to the method described in example 3, rac-(4S*,5R*)-2-(4-bromo-2-ethoxy-phenyl)-4,5-bis-(4-chloro-phenyl)-4,5-dimethyl-4,5-dihydro-1H-imidazole was reacted with phosgene in the presence of triethylamine to give the title compound.

EXAMPLE 76 rac-(4S*,5R*)-2-(4-Bromo-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone

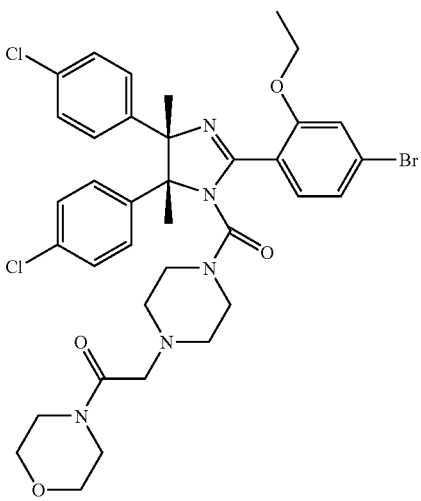

In a manner analogous to the method described in example 5, rac-(4S*,5R*)-2-(4-bromo-2-ethoxy-phenyl)-4,5-bis-(4-chloro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound. HR-MS (ES, m/z) calculated for $C_{36}H_{41}N_5O_4Cl_2Br$ [(M+H)$^+$] 756.1714, observed 756.1720.

EXAMPLE 77 rac-2-{4-[(4S*,5R*)-4,5-Bis-(4-chloro-phenyl)-4,5-dimethyl-4,5-dihydro-1H-imidazol-2-yl]-3-ethoxy-phenyl}-propan-2-ol

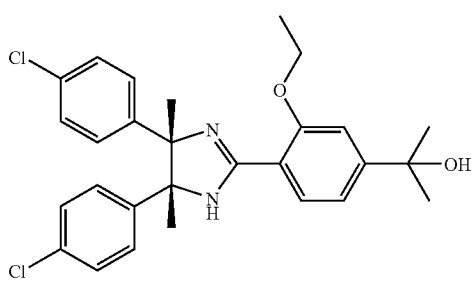

To a solution of n-butyllithium (11.6 mL, 28.95 mmol, 2.5 M solution in hexane, Aldrich) in tetrahydrofuran (50 mL) at −78° C. was added dropwise a solution of rac-(4S*,5R*)-2-(4-bromo-2-ethoxy-phenyl)-4,5-bis-(4-chloro-phenyl)-4,5-dimethyl-4,5-dihydro-1H-imidazole (1.5 g, 2.894 mmol, example 74) in tetrahydrofuran (50 mL). The brown reaction mixture was stirred at −78° C. for 15 min then acetone (2.12 mL, 28.94 mmol) was added dropwise. The color turned yellow at the end of addition. The reaction mixture was stirred at −78° C. for 30 min then quenched with water. The ice bath was removed to let the reaction warmed up to room temperature. The reaction was worked up with water and ethyl acetate. The organic layers were washed with brine and dried over anhydrous sodium sulfate. The solids were filtered off and the filtrate was concentrated to give a yellow residue. Purification of the crude residue by flash chromatography (120 g of silica gel, eluting with 100% ethyl acetate, 2-5% methanol in ethyl acetate) to give the title compound (702 mg, 49%). HR-MS (ES, m/z) calculated for $C_{28}H_{31}N_2O_2Cl_2$ [(M+H)$^+$] 497.1757, observed 497.1758.

A small amount of the side product, rac-(4S*,5R*)-4,5-bis-(4-chloro-phenyl)-2-(2-ethoxy-phenyl)-4,5-dimethyl-4,5-dihydro-1H-imidazole, was also obtained (187 mg, 15%). HR-MS (ES, m/z) calculated for $C_{25}H_{25}N_2OCl_2$ [(M+H)$^+$] 439.1339, observed 439.1339.

EXAMPLE 78 rac-(4S*,5R*)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride

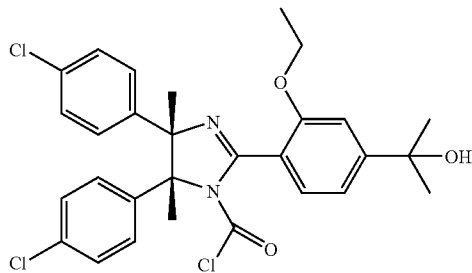

In a manner analogous to the method described in example 3, rac-2-{4-[(4S*,5R*)-4,5-bis-(4-chloro-phenyl)-4,5-dimethyl-4,5-dihydro-1H-imidazol-2-yl]-3-ethoxy-phenyl}-propan-2-ol was reacted with phosgene in the presence of triethylamine to give the title compound.

EXAMPLE 79 rac-(4S*,5R*)-4,5-Bis-(4-chloro-phenyl)-2-(2-ethoxy-phenyl)-4,5-dimethyl-4,5-dihydro-imidazole-1-carbonyl chloride

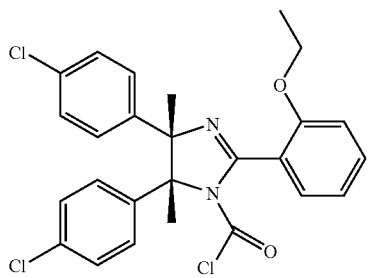

In a manner analogous to the method described in example 3, rac-(4S*,5R*)-4,5-bis-(4-chloro-phenyl)-2-(2-ethoxy-phenyl)-4,5-dimethyl-4,5-dihydro-1H-imidazole was reacted with phosgene in the presence of triethylamine to give the title compound.

EXAMPLE 80

[(4S,5R)-4,5-Bis-(4-chloro-phenyl)-2-(2-ethoxy-phenyl)-4,5-dimethyl-4,5-dihydro-imidazol-1-yl]-[4-(3-methanesulfonyl-propyl)-piperazin-1-yl]-methanone

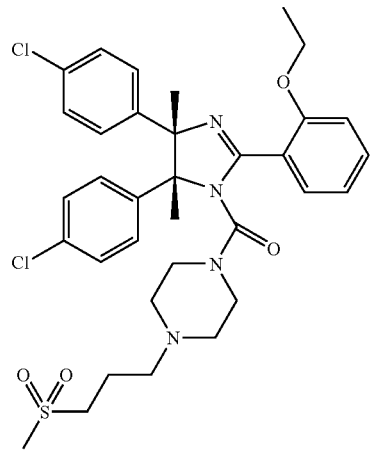

In a manner analogous to the method described in example 5, rac-(4S*,5R*)-4,5-bis-(4-chloro-phenyl)-2-(2-ethoxy-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% of 1:1 ethanol/acetonitrile in carbon dioxide). HR-MS (ES, m/z) calculated for $C_{34}H_{41}N_4O_4SCl_2$ [(M+H)$^+$] 671.2220, observed 671.2218.

EXAMPLE 81

2-{4-[(4S,5R)-4,5-Bis-(4-chloro-phenyl)-2-(2-ethoxy-phenyl)-4,5-dimethyl-4,5-dihydro-imidazole-1-carbonyl]-piperazin-1-yl}-acetamide

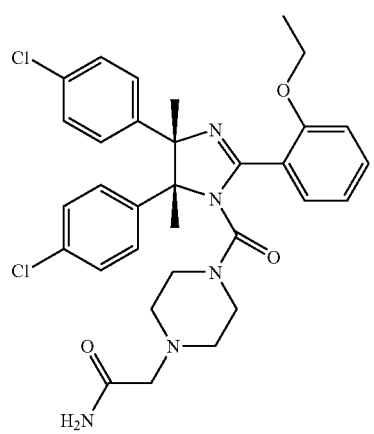

In a manner analogous to the method described in example 5, rac-(4S*,5R*)-4,5-bis-(4-chloro-phenyl)-2-(2-ethoxy-phenyl)-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% of 1:1 ethanol/acetonitrile in carbon dioxide). HR-MS (ES, m/z) calculated for $C_{32}H_{36}N_5O_3Cl_2$ [(M+H)$^+$] 608.2190, observed 608.2190.

EXAMPLE 82

{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(3-methanesulfonyl-propyl)-piperazin-1-yl]-methanone

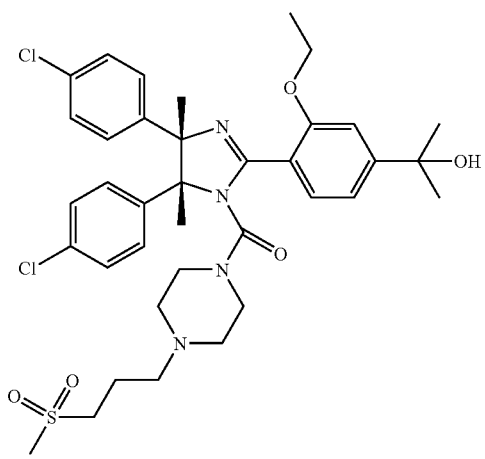

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% of 1:1 ethanol/acetonitrile in carbon dioxide). HR-MS (ES, m/z) calculated for $C_{37}H_{47}N_4O_5SCl_2$ [(M+H)$^+$] 729.2639, observed 729.2634.

EXAMPLE 83

2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-acetamide

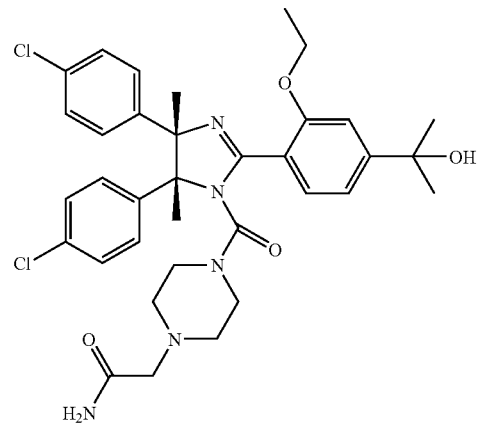

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 45% of 1:1 ethanol/acetonitrile in carbon dioxide). HR-MS (ES, m/z) calculated for $C_{35}H_{42}N_5O_4Cl_2$ [(M+H)$^+$] 666.2609, observed 666.2606.

EXAMPLE 84

{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(2-hydroxy-ethyl)-piperazin-1-yl]-methanone

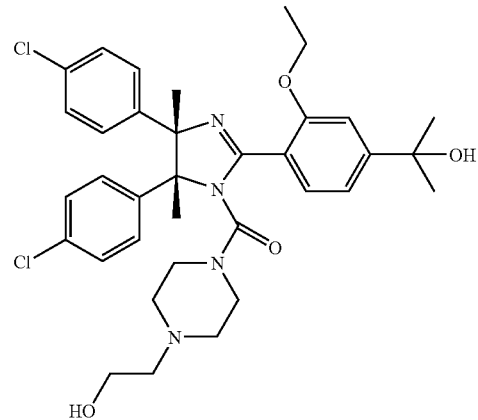

In a manner analogous to the method described in example 5, rac-(4S*,5R*)-4,5-bis-(4-chloro-phenyl)-2-[2-ethoxy-4-

(1-hydroxy-1-methyl-ethyl)-phenyl]-4,5-dimethyl-4,5-dihydro-imidazole-1-carbonyl chloride was reacted with 2-piperazin-1-yl-ethanol (Chemical Dynamics) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{35}H_{43}N_4O_4Cl_2$ [(M+H)$^+$] 653.2656, observed 653.2657.

EXAMPLE 85

2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-1-pyrrolidin-1-yl-ethanone

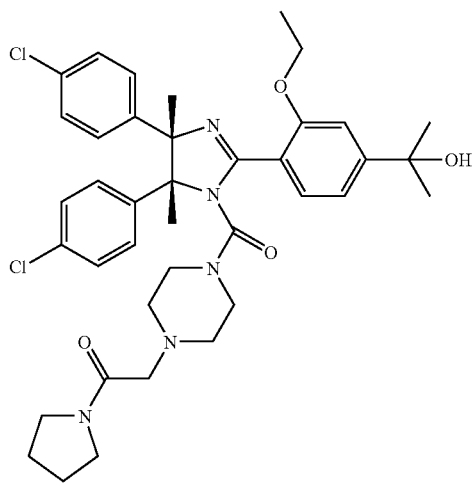

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with 2-piperazin-1-yl-1-pyrrolidin-1-yl-ethanone (Aldrich) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{39}H_{48}N_5O_4Cl_2$ [(M+H)$^+$] 720.3078, observed 720.3072.

EXAMPLE 86

N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-acetamide

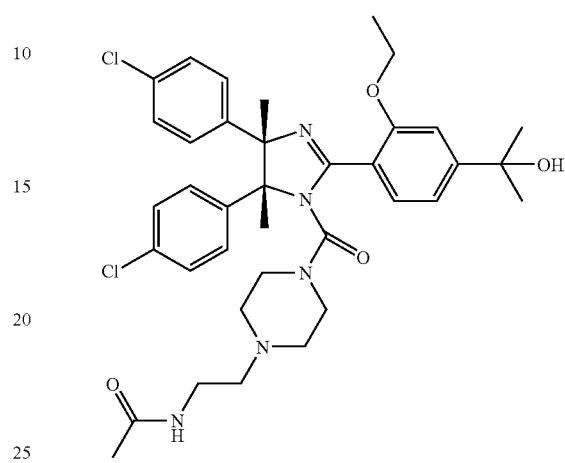

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with N-(2-piperazin-1-yl-ethyl)-acetamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{37}H_{46}N_5O_4Cl_2$ [(M+H)$^+$] 694.2922, observed 694.2918.

EXAMPLE 87

N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-methanesulfonamide

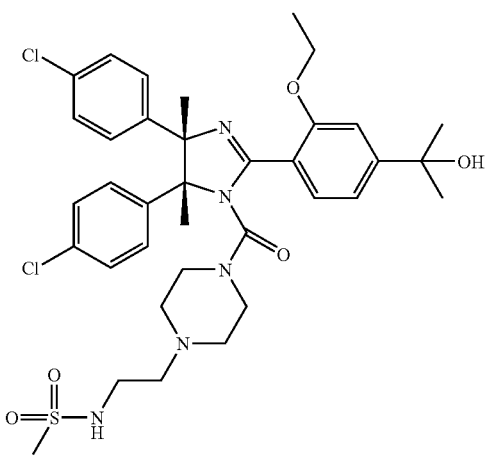

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with N-(2-piperazin-1-yl-ethyl)-methanesulfonamide dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{36}H_{45}N_5O_5SCl_2$ [(M+H)$^+$] 730.2591, observed 730.2585.

EXAMPLE 88

{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone

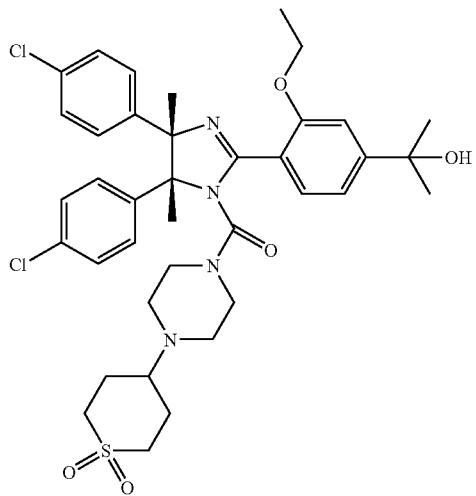

In a manner analogous to the method described in example 5, rac-(4S*,5R*)-4,5-bis-(4-chloro-phenyl)-2-[2-ethoxy-4-(1-hydroxy-1-methyl-ethyl)-phenyl]-4,5-dimethyl-4,5-dihydro-imidazole-1-carbonyl chloride was reacted with 1-(1,1-dioxo-tetrahydro-2H-thiopyran-4-yl)-piperazine dihydrochloride (example 22) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% of 1:1 ethanol/acetonitrile in carbon dioxide). HR-MS (ES, m/z) calculated for $C_{38}H_{47}N_4O_5SCl_2$ [(M+H)$^+$] 741.2639, observed 741.2637.

EXAMPLE 89 rac-(4S*,5R*)-4,5-Bis-(4-chloro-phenyl)-2-(2-isopropoxy-4-methoxy-phenyl)-4,5-dimethyl-4,5-dihydro-1H-imidazole

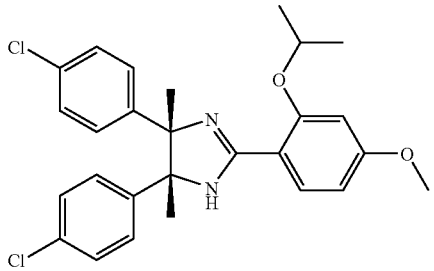

In a manner analogous to the method described in example 2, meso-2,3-bis-(4-chlorophenyl)-2,3-butanediamine was reacted with 2-isopropoxy-4-methoxybenzoic acid methyl ester (prepared in a manner analogous to the method described in example 56) in the presence of trimethylaluminum to give the title compound. HR-MS (ES, m/z) calculated for $C_{29}H_{34}N_3O_3SCl_2$ [(M+H)$^+$] 574.1693, observed 574.1589.

EXAMPLE 90 rac-(4S*,5R*)-4,5-Bis-(4-chloro-phenyl)-2-(2-isopropoxy-4-methoxy-phenyl)-4,5-dimethyl-4,5-dihydro-imidazole-1-carbonyl chloride

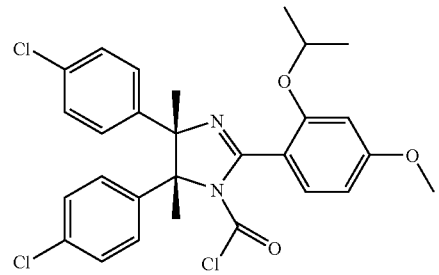

In a manner analogous to the method described in example 3, rac-(4S*,5R*)-4,5-Bis-(4-chloro-phenyl)-2-(2-isopropoxy-4-methoxy-phenyl)-4,5-dimethyl-4,5-dihydro-1H-imidazole was reacted with phosgene in the presence of triethylamine to give the title compound.

EXAMPLE 91 rac-(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(3-methanesulfonyl-propyl)-piperazin-1-yl]-methanone

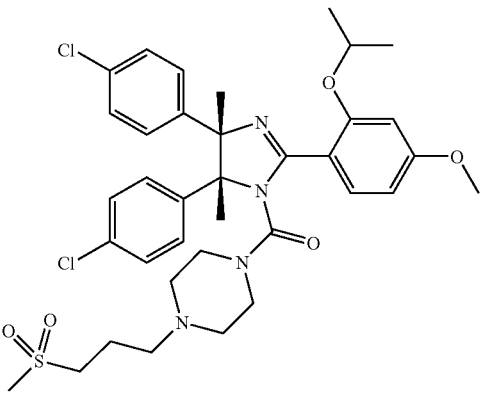

In a manner analogous to the method described in example 5, rac-(4S*,5R*)-4,5-bis-(4-chloro-phenyl)-2-(2-isopropoxy-4-methoxy-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound. HR-MS (ES, m/z) calculated for $C_{36}H_{45}N_4O_5SCl_2$ $[(M+H)^+]$ 715.2482, observed 715.2485.

EXAMPLE 92 rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-acetamide

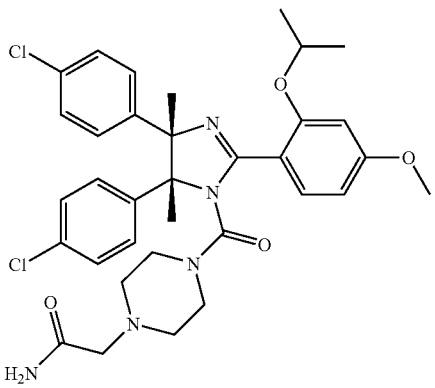

In a manner analogous to the method described in example 5, rac-(4S*,5R*)-4,5-bis-(4-chloro-phenyl)-2-(2-isopropoxy-4-methoxy-phenyl)-4,5-dimethyl-4,5-dihydro-imidazole-1-carbonyl chloride was reacted with 2-piperazin-1-yl-acetamide dihydrochloride (Matrix Scientific) to give the title compound. HR-MS (ES, m/z) calculated for $C_{34}H_{40}N_5O_4Cl_2$ $[(M+H)^+]$ 652.2452, observed 652.2451.

EXAMPLE 93 rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-1-morpholin-4-yl-ethanone

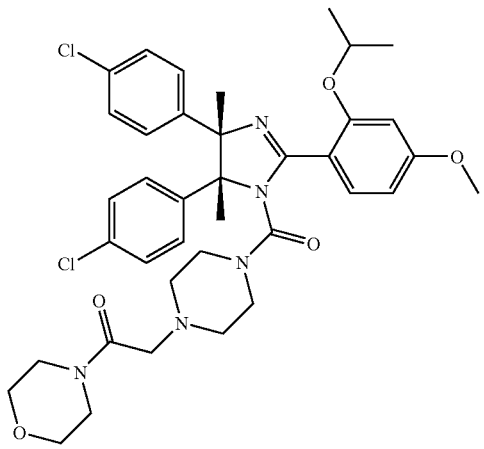

In a manner analogous to the method described in example 5, rac-(4S*,5R*)-4,5-bis-(4-chloro-phenyl)-2-(2-isopropoxy-4-methoxy-phenyl)-4,5-dimethyl-4,5-dihydro-imidazole-1-carbonyl chloride was reacted with 1-morpholin-4-yl-2-piperazin-1-yl-ethanone (Oakwood Products) to give the title compound. HR-MS (ES, m/z) calculated for $C_{38}H_{46}N_5O_5Cl_2$ $[(M+H)^+]$ 722.2871, observed 722.2874.

EXAMPLE 94 rac-4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-2-one

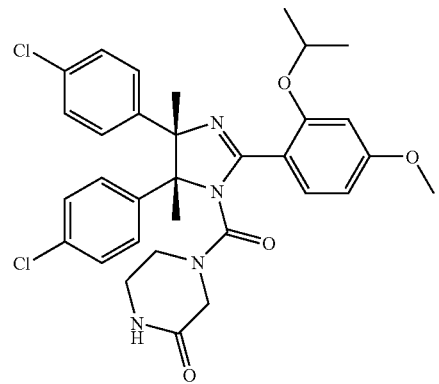

In a manner analogous to the method described in example 5, rac-(4S*,5R*)-4,5-bis-(4-chloro-phenyl)-2-(2-isopropoxy-4-methoxy-phenyl)-4,5-dimethyl-4,5-dihydro-imidazole-1-carbonyl chloride was reacted with 2-piperazinone (Avocado Organics) to give the title compound. HR-MS (ES, m/z) calculated for $C_{32}H_{35}N_4O_4Cl_2$ $[(M+H)^+]$ 609.2030, observed 609.2025.

EXAMPLE 95 rac-[(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(2-methanesulfonyl-ethyl)-piperazin-1-yl]-methanone

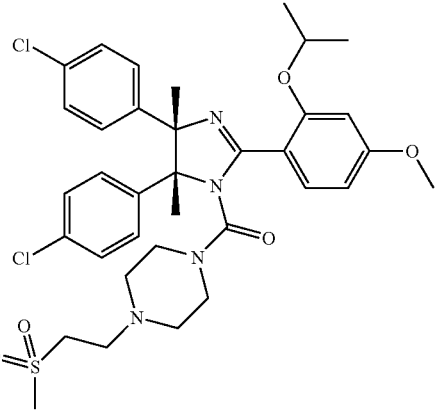

In a manner analogous to the method described in example 5, rac-(4S*,5R*)-4,5-bis-(4-chloro-phenyl)-2-(2-isopropoxy-4-methoxy-phenyl)-4,5-dimethyl-4,5-dihydro-imidazole-1-carbonyl chloride was reacted with 1-(2-methanesulfonyl-ethyl)-piperazine (prepared as described in Fotouhi, N. et al. WO 2005110996) to give the title compound. HR-MS (ES, m/z) calculated for $C_{35}H_{43}N_4O_5SCl_2$ [(M+H)$^+$] 701.2326, observed 701.2325.

EXAMPLE 96 rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-1H-imidazole

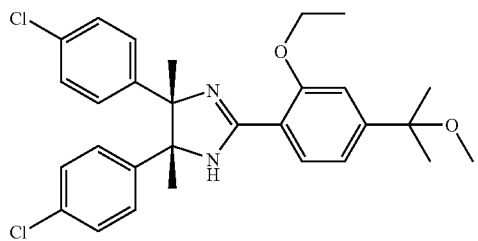

To a solution of 1-bromo-3-ethoxy-benzene (20 g, 99.473 mmol) in anhydrous tetrahydrofuran (300 mL) cooled to −78° C. was added 2.5 M n-butyllithium in hexane (39.8 mL, 99.473 mmol, Aldrich) The reaction mixture was stirred at −78° C. for 5 min then acetone (43.8 mL, 596.838 mmol) was added. After 30 min at −78° C., the ice bath was removed and saturated solution of ammonium chloride was added to quench the reaction. The product was extracted with ethyl acetate (2×150 mL). The combined organic layers were washed with brine (1×50 mL) and dried over anhydrous sodium sulfate. The solids were filtered off, and the filtrate was concentrated in vacuo. Purification of the crude residue by flash chromatography (silica gel, eluting with 15-25% ethyl acetate in hexane) gave the 2-(3-ethoxy-phenyl)-propan-2-ol as clear oil (10.930 g, 61%).

Sodium hydride (3.261 g, 81.54 mmol, 60% in mineral oil, Aldrich) was washed twice with hexane, and tetrahydrofuran (60 mL) was added. To this suspension was added 2-(3-ethoxy-phenyl)-propan-2-ol (4.9 g, 27.18 mmol). The mixture was stirred at 45° C. for 1.5 h until the bubbling subsided. It was cooled down to 0° C. and iodomethane (5.08 mL, 81.54 mmol, Aldrich) was added. After 4 h of stirring at room temperature, another portion of iodomethane (5.08 mL, 81.54 mmol) was added. The mixture was stirred at room temperature for 4 d then quenched at 0° C. with cold 20% solution of ammonium chloride. The product was extracted with ethyl acetate (2×1 L). The organic extracts were washed with brine and dried over anhydrous sodium sulfate. The solids were filtered off, and the filtrate was concentrated in vacuo to give 1-ethoxy-3-(1-methoxy-1-methyl-ethyl)-benzene (5.15 g, 97%).

To a solution of 1-ethoxy-3-(1-methoxy-1-methyl-ethyl)-benzene (5.15 g, 26.51 mmol) in acetonitrile (60 mL) were added N-iodosuccinimide (8.349 g, 37.11 mmol) and trifluoroacetic acid (1.02 mL, 13.26 mmol). The mixture was stirred at room temperature overnight. It was then concentrated in vacuo and the residue was taken in ethyl acetate. After washing with saturated solution of sodium bicarbonate, water and brine, the organic layer was dried over anhydrous sodium sulfate. The solids were filtered off, and the filtrate was concentrated in vacuo to give 9.39 g of 2-ethoxy-1-iodo-4-(1-methoxy-1-methyl-ethyl)-benzene as light brown oil.

Diisopropylethylamine (10.15 mL, 58.10 mmol) was added to a solution of 2-ethoxy-1-iodo-4-(1-methoxy-1-methyl-ethyl)-benzene (9.3 g, 29.05 mmol) in methanol (60 mL). Argon was bubbling through the mixture for 30 min and palladium (II) acetate (653 mg, 2.91 mmol) was added. The reaction flash was flushed with carbon monoxide several times then stirred at 60° C. for 18 h under a pressure of carbon monoxide (40 psi). The reaction mixture was concentrated and the residue was taken in ethyl acetate. It was washed with water, brine and dried over anhydrous sodium sulfate and concentrated. Purification of the crude residue by flash chromatography (silica gel, eluting with 10-30% ethyl acetate in hexane over 30 min) gave 2-ethoxy-4-(1-methoxy-1-methyl-ethyl)-benzoic acid methyl ester (2.81 g).

In a manner analogous to the method described in example 2, meso-2,3-bis-(4-chlorophenyl)-2,3-butanediamine was reacted with 2-ethoxy-4-(1-methoxy-1-methyl-ethyl)-benzoic acid methyl ester in the presence of trimethylaluminum to give the title compound.

EXAMPLE 97 rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl chloride

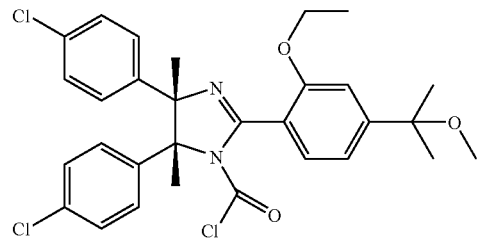

In a manner analogous to the method described in example 3, rac-(4S*,5R*)-4,5-bis-(4-chloro-phenyl)-2-[2-ethoxy-4-(1-methoxy-1-methyl-ethyl)-phenyl]-4,5-dimethyl-4,5-dihydro-1H-imidazole was reacted with phosgene in the presence of triethylamine to give the title compound.

EXAMPLE 98

2-(4-{(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl}-piperazin-1-yl)-acetamide

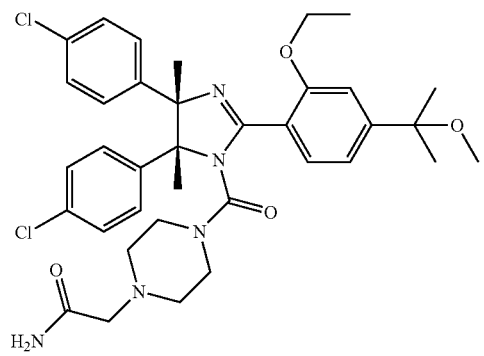

In a manner analogous to the method described in example 5, 4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl chloride was reacted with 2-piperazin-1-yl-acetamide dihydrochloride (Matrix Scientific) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{36}H_{44}N_5O_4Cl_2$ [(M+H)$^+$] 680.2765, observed 680.2767.

EXAMPLE 99

{rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(3-methane-sulfonyl-propyl)-piperazin-1-yl]-methanone

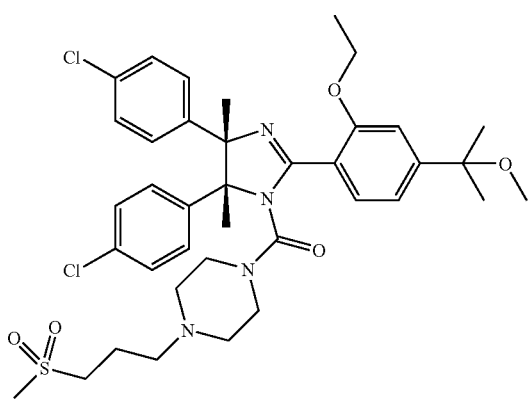

In a manner analogous to the method described in example 5, 4,5-bis-(4-chloro-phenyl)-2-[2-ethoxy-4-(1-methoxy-1-methyl-ethyl)-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{38}H_{49}N_4O_5SCl_2$ [(M+H)$^+$] 743.2795, observed 743.2795.

EXAMPLE 100

{(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone

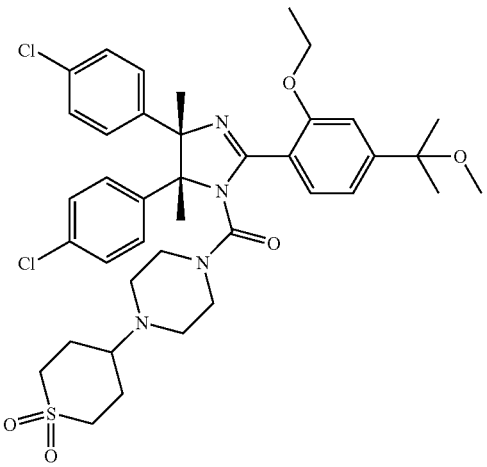

In a manner analogous to the method described in example 5, 4,5-bis-(4-chloro-phenyl)-2-[2-ethoxy-4-(1-methoxy-1-methyl-ethyl)-phenyl]-4,5-dimethyl-4,5-dihydro-imidazole-1-carbonyl chloride was reacted with 1-(1,1-dioxo-tetrahydro-2H-thiopyran-4-yl)-piperazine dihydrochloride (example 22) to give the title compound as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{39}H_{49}N_4O_5SCl_2$ [(M+H)$^+$] 755.2795, observed 755.2792.

EXAMPLE 101 rac-1-[(4S*,5R*)-2-(4-tert-Butyl-2-ethoxy-phenyl)-4,5-bis-(4-chloro-phenyl)-4,5-dimethyl-4,5-dihydro-imidazol-1-yl]-ethanone

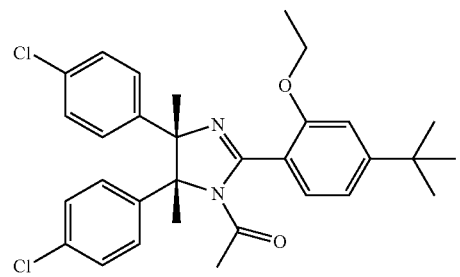

To a solution of rac-(4S*,5R*)-2-(4-tert-butyl-2-ethoxy-phenyl)-4,5-bis-(4-chloro-phenyl)-4,5-dimethyl-4,5-dihydro-1H-imidazole (70 mg, 0.13 mmol, example 2) and triethylamine (92 uL, 0.65 mmol) in methylene chloride (3 mL) was added acetyl chloride (59 uL, Aldrich). The reaction mixture was stirred at room temperature overnight then concentrated. Purification of the crude residue by flash chromatography (12 g of silica gel, eluting with 5-30% ethyl acetate in hexane) gave the title compound (56.1 mg, 80%). HR-MS (ES, m/z) calculated for $C_{31}H_{34}N_2O_2Cl_2$ $[(M+H)^+]$ 537.2070, observed 537.2068.

EXAMPLE 102

1-[(4S,5R)-2-(4-tert-Butyl-2-ethoxy-phenyl)-4,5-bis-(4-chloro-phenyl)-4,5-dimethyl-4,5-dihydro-imidazol-1-yl]-2-methyl-propan-1-one

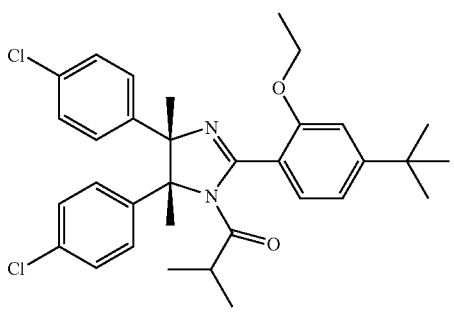

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with isobutyryl chloride (Aldrich) to give the title compound. HR-MS (ES, m/z) calculated for $C_{33}H_{37}N_2O_2Cl_2$ $[(M+H)^+]$ 565.2383, observed 565.2384.

EXAMPLE 103

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclopropyl-methanone

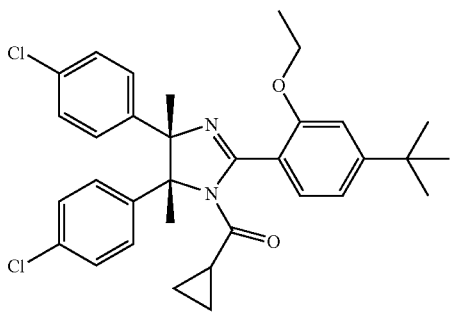

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with cyclopropanecarbonyl chloride (Aldrich) to give the title compound. HR-MS (ES, m/z) calculated for $C_{33}H_{37}N_2O_2Cl_2$ $[(M+H)^+]$ 563.2227, observed 563.2224.

EXAMPLE 104

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclobutyl-methanone

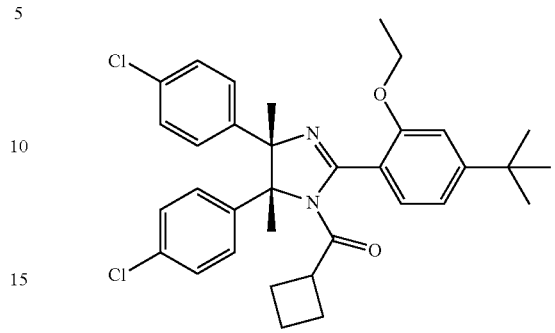

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with cyclobutanecarbonyl chloride (Aldrich) to give the title compound. HR-MS (ES, m/z) calculated for $C_{34}H_{39}N_2O_2Cl_2$ $[(M+H)^+]$ 577.2383, observed 577.2382.

EXAMPLE 105

1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-methyl-butan-1-one

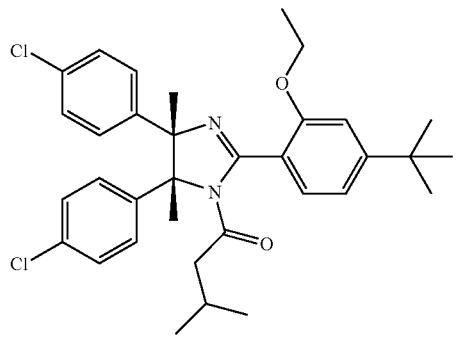

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 3-methyl-butyryl chloride (Aldrich) to give the title compound. HR-MS (ES, m/z) calculated for $C_{34}H_{41}N_2O_2Cl_2$ $[(M+H)^+]$ 579.2540, observed 579.2543.

EXAMPLE 106

1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-phenyl-propan-1-one

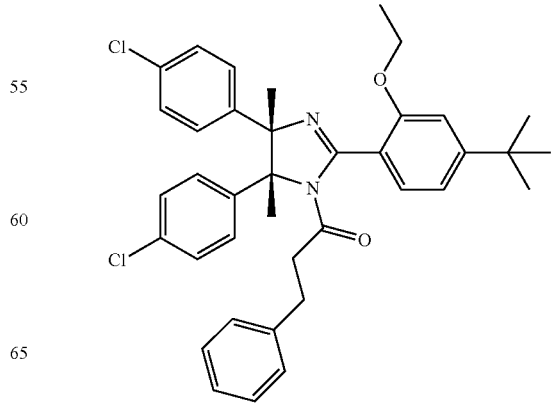

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 3-phenyl-propionyl chloride (Aldrich) to give the title compound. HR-MS (ES, m/z) calculated for $C_{38}H_{41}N_2O_2Cl_2$ [(M+H)$^+$] 627.2540, observed 627.2541.

EXAMPLE 107

4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-benzonitrile

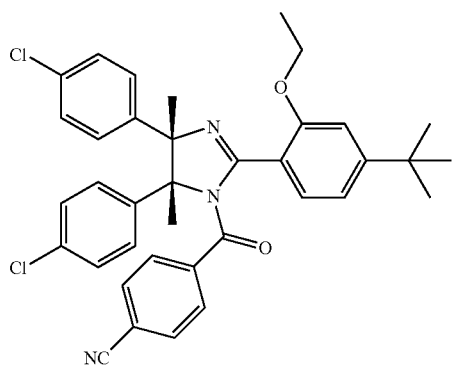

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 4-cyano-benzoyl chloride (Aldrich) to give the title compound. HR-MS (ES, m/z) calculated for $C_{37}H_{36}N_3O_2Cl_2$ [(M+H)$^+$] 624.2179, observed 624.2177.

EXAMPLE 108

[(4S,5R)-2-(4-tert-Butyl-2-ethoxy-phenyl)-4,5-bis-(4-chloro-phenyl)-4,5-dimethyl-4,5-dihydro-imidazol-1-yl]-furan-2-yl-methanone

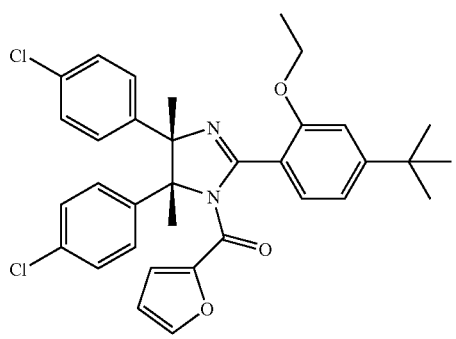

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with furan-2-carbonyl chloride (Aldrich) to give the title compound. HR-MS (ES, m/z) calculated for $C_{34}H_{35}N_2O_3Cl_2$ [(M+H)$^+$] 589.2019, observed 589.2017.

EXAMPLE 109

[(4S,5R)-2-(4-tert-Butyl-2-ethoxy-phenyl)-4,5-bis-(4-chloro-phenyl)-4,5-dimethyl-4,5-dihydro-imidazol-1-yl]-phenyl-methanone

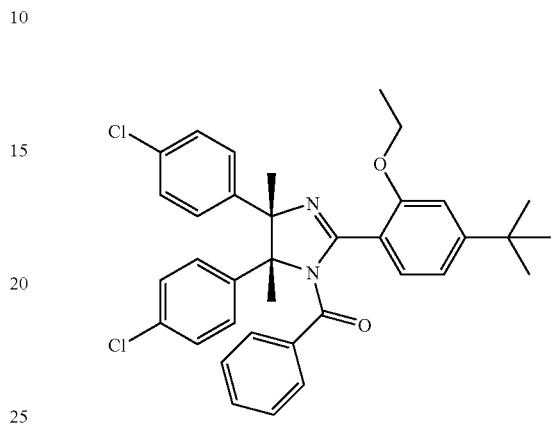

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with benzoyl chloride (Aldrich) to give the title compound. HR-MS (ES, m/z) calculated for $C_{36}H_{37}N_2O_2Cl_2$ [(M+H)$^+$] 599.2227, observed 599.2223.

EXAMPLE 108 rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-methoxy-phenyl)-methanone

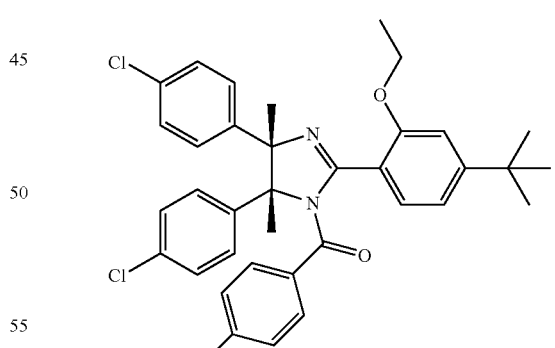

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 4-methoxybenzoyl chloride (Aldrich) to give the title compound. HR-MS (ES, m/z) calculated for $C_{37}H_{39}N_2O_3Cl_2$ [(M+H)$^+$] 629.2332, observed 629.2337.

EXAMPLE 111 rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-chloro-phenyl)-methanone

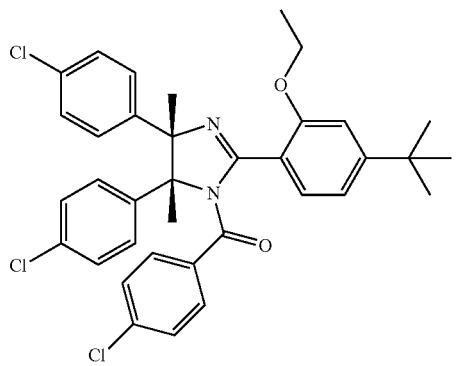

In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 4-chlorobenzoyl chloride (Aldrich) to give the title compound. HR-MS (ES, m/z) calculated for $C_{36}H_{36}N_2O_3Cl_3$ [(M+H)$^+$] 633.1837, observed 633.1838.

EXAMPLE 112 rac-(4S*,5R*)-2-(4-tert-Butyl-5-chloro-2-ethoxy-phenyl)-4,5-bis-(4-chloro-phenyl)-4,5-dimethyl-4,5-dihydro-1H-imidazole

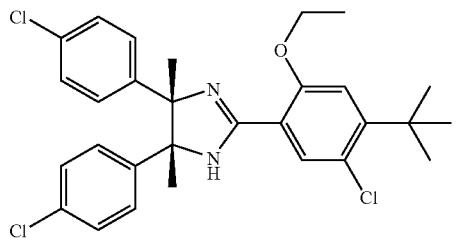

In a manner analogous to the method described in example 2, meso-2,3-bis-(4-chlorophenyl)-2,3-butanediamine was reacted with 4-tert-butyl-5-chloro-2-ethoxy-benzoic acid methyl ester (prepared as described in Fotouhi, N. et al. WO 2005110996) in the presence of trimethylaluminum to give the title compound.

EXAMPLE 113 rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl chloride

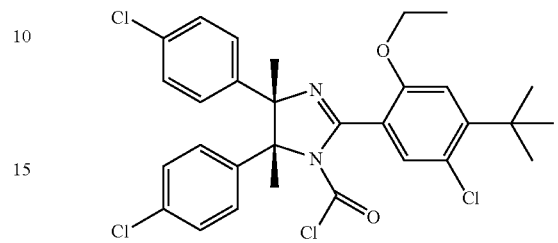

In a manner analogous to the method described in example 3, rac-(4S*,5R*)-4,5-bis-(4-chloro-phenyl)-2-[2-ethoxy-4-(1-methoxy-1-methyl-ethyl)-phenyl]-4,5-dimethyl-4,5-dihydro-1H-imidazole was reacted with phosgene in the presence of triethylamine to give the title compound.

EXAMPLE 114

[(4S,5R)-2-(4-tert-Butyl-5-chloro-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone

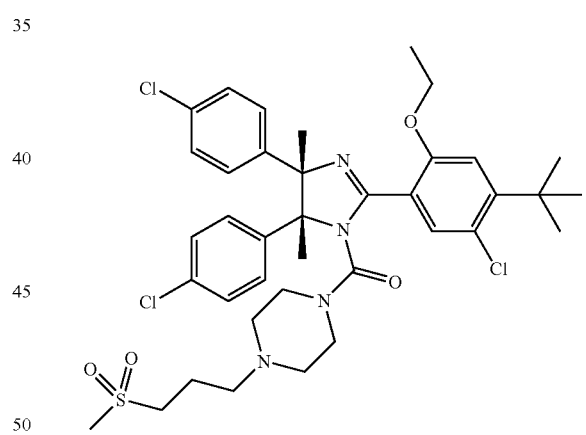

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with 1-(3-methanesulfonyl-propyl)-piperazine dihydrochloride (prepared as described in Fotouhi, N. et al. WO 2005110996) to give the racemic rac-(4S*,5R*)-2-(4-tert-butyl-5-chloro-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone. Chiral separation of the enantiomers by supercritical fluid chromatography (Berger Instrument Multi-Gram II, Daicel ChiralPak OD-H 3×25 cm, 35° C. at 100 bar, eluting with 25% methanol in carbon dioxide) gave the title compound. HR-MS (ES, m/z) calculated for $C_{38}H_{48}N_4O_4SCl_3$ [(M+H)$^+$] 761.2457, observed 761.2460.

EXAMPLE 115

2-{4-[(4S,5R)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-acetamide

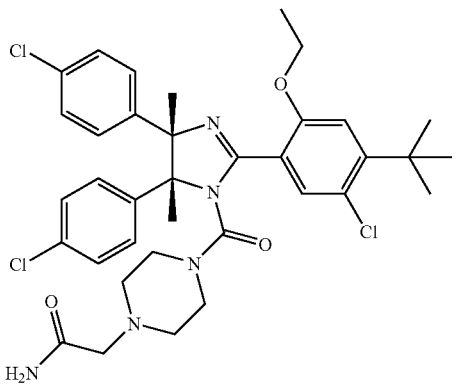

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with 2-piperazin-1-yl-acetamide dihydrochloride (Matrix Scientific) to give the racemic 2-rac-{4-[(4S*,5R*)-2-(4-tert-butyl-5-chloro-2-ethoxy-phenyl)-4,5-bis-(4-chloro-phenyl)-4,5-dimethyl-4,5-dihydro-imidazole-1-carbonyl]-piperazin-1-yl}-acetamide. Chiral separation of the enantiomers by supercritical fluid chromatography (Berger Instrument Multi-Gram II, Daicel ChiralPak OD-H 3×25 cm, 35° C. at 100 bar, eluting with 25% methanol in carbon dioxide) gave the title compound. HR-MS (ES, m/z) calculated for $C_{36}H_{43}N_5O_3Cl_3$ [(M+H)$^+$] 698.2426, observed 698.2431.

EXAMPLE 116 rac-(2-{4-[4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-1-morpholin-4-yl-ethanone

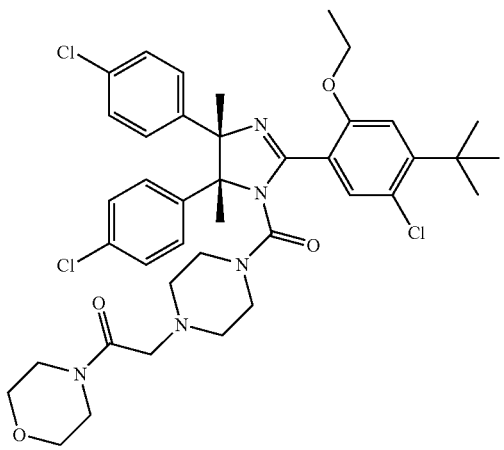

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with 1-morpholin-4-yl-2-piperazin-1-yl-ethanone (Oakwood Products) to give the title compound. HR-MS (ES, m/z) calculated for $C_{40}H_{49}N_5O_4Cl_3$ [(M+H)$^+$] 768.2845, observed 768.2845.

EXAMPLE 117 rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-dimethylamino-piperidin-1-yl)-methanone

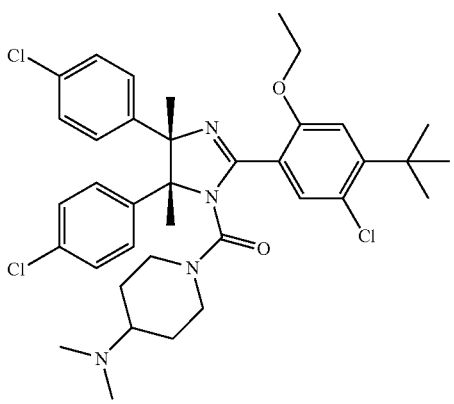

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with dimethyl-piperidin-4-yl-amine (Aldrich) to give the title compound. HR-MS (ES, m/z) calculated for $C_{37}H_{46}N_4O_2Cl_3$ [(M+H)$^+$] 683.2681, observed 683.2681.

EXAMPLE 118 rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-pyrrolidin-1-yl-piperidin-1-yl)-methanone

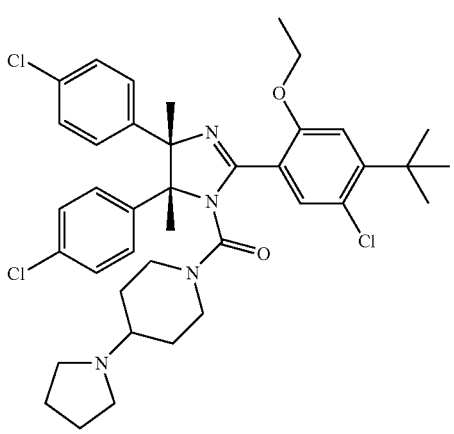

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with 4-pyrrolidin-1-yl-piperidine (Aldrich) to give the title compound. HR-MS (ES, m/z) calculated for $C_{39}H_{48}N_4O_2Cl_3$ [(M+H)$^+$] 709.2838, observed 709.2836.

EXAMPLE 119 rac-[1,4']Bipiperidinyl-1'-yl-[(4S*,5R*)-2-(4-tert-butyl-5-chloro-2-ethoxy-phenyl)-4,5-bis-(4-chloro-phenyl)-4,5-dimethyl-4,5-dihydro-imidazol-1-yl]-methanone

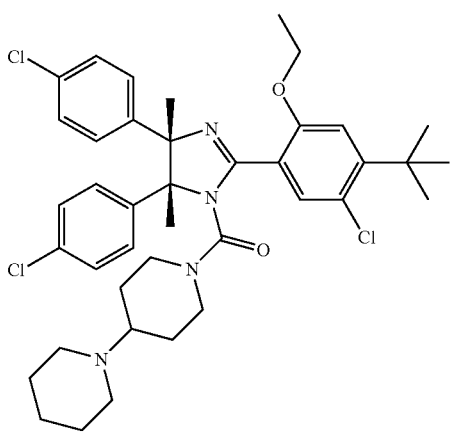

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with [1,4']bipiperidinyl (Aldrich) to give the title compound. HR-MS (ES, m/z) calculated for $C_{40}H_{50}N_4O_2Cl_3$ [(M+H)$^+$] 723.2994, observed 723.2997.

EXAMPLE 120 rac-{1-[(4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperidin-4-yl}-carbamic acid tert-butyl ester

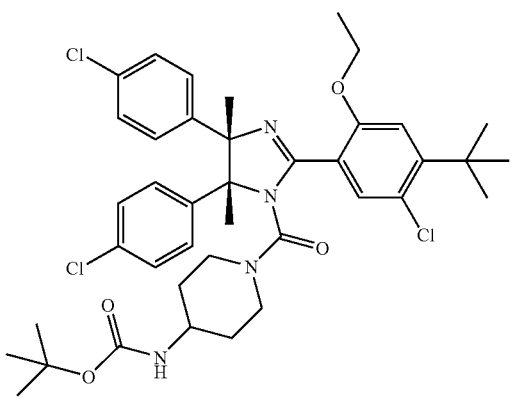

In a manner analogous to the method described in example 5, rac-(4S*,5R*)-2-(4-tert-butyl-5-chloro-2-ethoxy-phenyl)-4,5-bis-(4-chloro-phenyl)-4,5-dimethyl-4,5-dihydro-1H-imidazole was reacted with piperidin-4-yl-carbamic acid tert-butyl ester (Aldrich) to give the title compound. HR-MS (ES, m/z) calculated for $C_{40}H_{50}N_4O_4Cl_3$ [(M+H)$^+$] 755.2892, observed 755.2895.

EXAMPLE 121 rac-(4S*,5R*)-4,5-Bis-(4-chloro-phenyl)-2-(2-ethoxy-4-trifluoromethyl-phenyl)-4,5-dimethyl-4,5-dihydro-1H-imidazole

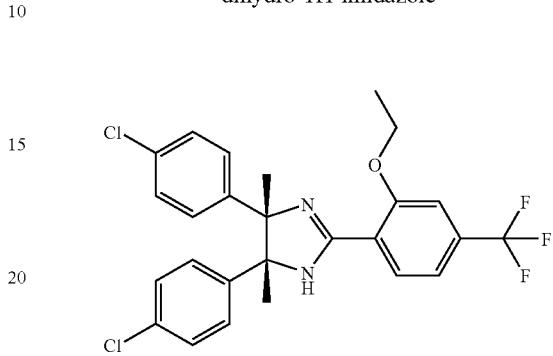

To a solution of 2-hydroxy-4-trifluoromethyl-benzoic acid (5 g, 24.258 mmol, Matrix Scientific) in ethanol (50 mL) were added potassium carbonate (8.38 g, 60.645 mmol) and ethyl iodide (7.68 mL, 97.032 mmol). The reaction mixture was heated at gentle reflux for 4 h then concentrated in vacuo. The residue was taken in petroleum ether and water, and the layers were separated. The product was extracted with petroleum ether (1×). The organic layers were washed with brine (1×), dried over anhydrous sodium sulfate, filtered and concentrated. Purification of the crude residue by flash chromatography (40 g of silica gel, eluting with 10% ethyl acetate in hexane) gave 2-ethoxy-4-trifluoromethyl-benzoic acid ethyl ester as colorless oil (4.68 g, 74%).

In a manner analogous to the method described in example 2, meso-2,3-bis-(4-chlorophenyl)-2,3-butanediamine was reacted with 2-ethoxy-4-trifluoromethyl-benzoic acid ethyl ester in the presence of trimethylaluminum to give the title compound. HR-MS (ES, m/z) calculated for $C_{26}H_{24}N_2OF_3Cl_2$ [(M+H)$^+$] 507.1213, observed 507.1207.

EXAMPLE 122 rac-(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl chloride

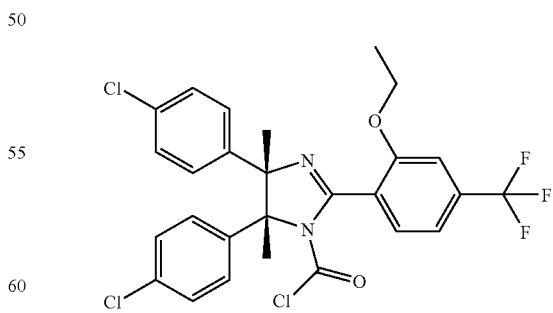

In a manner analogous to the method described in example 3, rac-(4S*,5R*)-4,5-bis-(4-chloro-phenyl)-2-(2-ethoxy-4-trifluoromethyl-phenyl)-4,5-dimethyl-4,5-dihydro-1H-imidazole was reacted with phosgene in the presence of triethylamine to give the title compound.

EXAMPLE 123 rac-4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-2-one

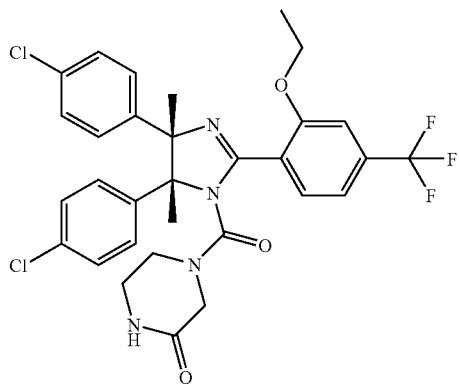

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 2-piperazinone (Avocado Organics) to give the title compound. HR-MS (ES, m/z) calculated for $C_{31}H_{30}N_4O_3F_3Cl_2$ [(M+H)$^+$] 633.1642, observed 633.1638.

EXAMPLE 124 rac-1-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-ethanone

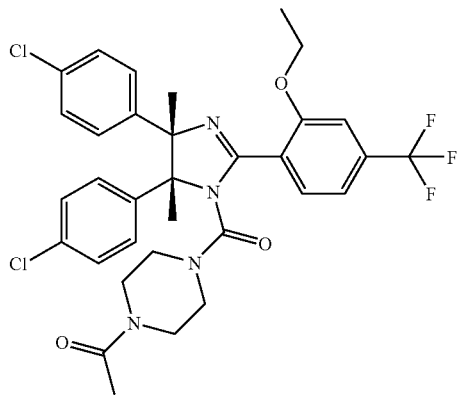

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-acetyl-piperazine (Aldrich) to give the title compound. HR-MS (ES, m/z) calculated for $C_{33}H_{34}N_4O_3F_3Cl_2$ [(M+H)$^+$] 661.1955, observed 661.1947.

EXAMPLE 125

[(4S,5R)-4,5-Bis-(4-chloro-phenyl)-2-(2-ethoxy-4-trifluoromethyl-phenyl)-4,5-dimethyl-4,5-dihydro-imidazol-1-yl]-[4-(3-methanesulfonyl-propyl)-piperazin-1-yl]-methanone

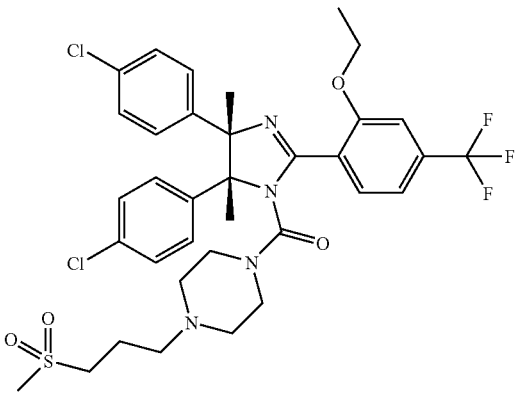

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the racemic rac-(4S*,5R*)-4,5-bis-(4-chloro-phenyl)-2-(2-ethoxy-4-trifluoromethyl-phenyl)-4,5-dimethyl-4,5-dihydro-imidazol-1-yl]-[4-(3-methanesulfonyl-propyl)-piperazin-1-yl]-methanone. Chiral separation of the enantiomers by supercritical fluid chromatography (Berger Instrument Multi-Gram II, Daicel ChiralPak OD-H 3×25 cm, 35° C. at 100 bar, eluting with 25% methanol in carbon dioxide) gave the title compound. HR-MS (ES, m/z) calculated for $C_{35}H_{40}N_4O_4SF_3Cl_2$ [(M+H)$^+$] 739.2094, observed 739.2094.

EXAMPLE 126 rac-2-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-1-morpholin-4-yl-ethanone

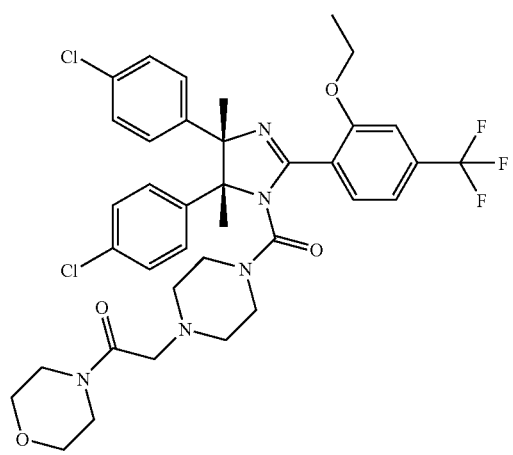

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-morpholin-4-yl-2-piperazin-1-yl-ethanone (Oakwood Products) to give the title compound. HR-MS (ES, m/z) calculated for $C_{37}H_{41}N_5O_4F_3Cl_2$ [(M+H)$^+$] 746.2482, observed 746.2483.

EXAMPLE 127 rac-(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-ethanesulfonyl-piperazin-1-yl)-methanone

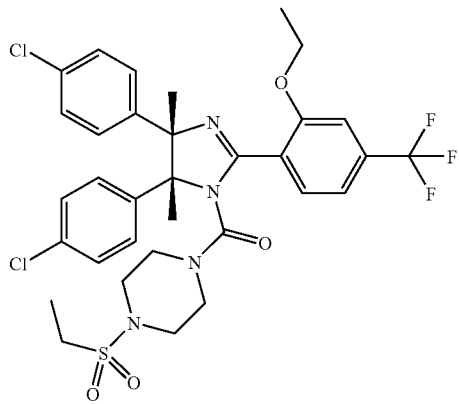

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-ethanesulfonyl-piperazine (Aldrich) to give the title compound. HR-MS (ES, m/z) calculated for $C_{33}H_{36}N_4O_4SF_3Cl_2$ [(M+H)$^+$] 711.1781, observed 711.1786.

EXAMPLE 128 rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (1-methanesulfonyl-piperidin-4-yl)-amide

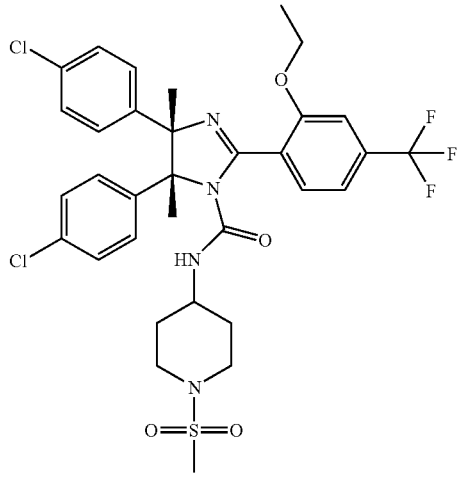

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-methanesulfonyl-piperidin-4-ylamine (prepared as described by Bartkovitz, D. J. et al. WO2004069139) to give the title compound. HR-MS (ES, m/z) calculated for $C_{33}H_{36}N_4O_4SF_3Cl_2$ [(M+H)$^+$] 711.1781, observed 711.1778.

EXAMPLE 129 rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(4-methyl-piperazin-1-yl)-piperidin-1-yl]-methanone

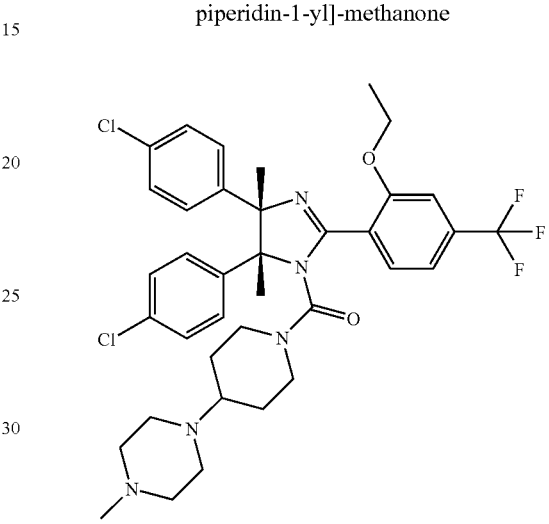

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 1-methyl-4-piperidin-4-yl-piperazine (Oakwood Products) to give the title compound. HR-MS (ES, m/z) calculated for $C_{37}H_{43}N_5O_2F_3Cl_2$ [(M+H)$^+$] 716.2741, observed 716.2746.

EXAMPLE 130 rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-morpholin-4-yl-piperidin-1-yl)-methanone

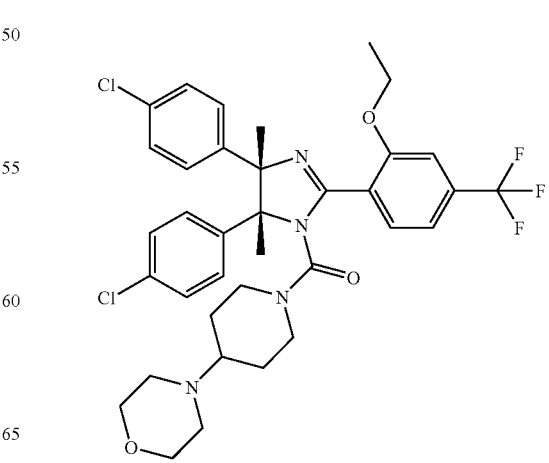

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 4-piperidin-4-yl-morpholine (Aldrich) to give the title compound. HR-MS (ES, m/z) calculated for $C_{36}H_{40}N_4O_3F_3Cl_2$ [(M+H)$^+$] 703.2424, observed 703.2419.

EXAMPLE 131 rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxy-piperidin-1-yl)-methanone

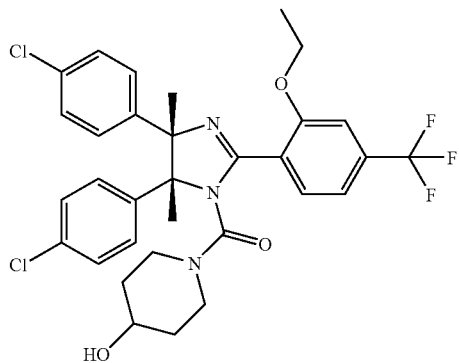

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 4-hydroxy-piperidine (Aldrich) to give the title compound. HR-MS (ES, m/z) calculated for $C_{32}H_{33}N_3O_3F_3Cl_2$ [(M+H)$^+$] 634.1846, observed 634.1846.

EXAMPLE 132 rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxymethyl-piperidin-1-yl)-methanone

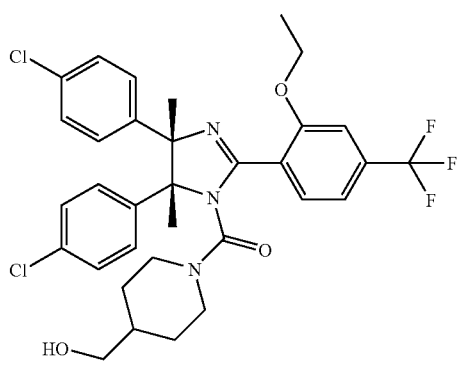

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with piperidin-4-yl-methanol (Lancaster) to give the title compound. HR-MS (ES, m/z) calculated for $C_{33}H_{35}N_3O_3F_3Cl_2$ [(M+H)$^+$] 648.2002, observed 648.2006.

EXAMPLE 133 rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(2-hydroxy-ethyl)-piperidin-1-yl]-methanone

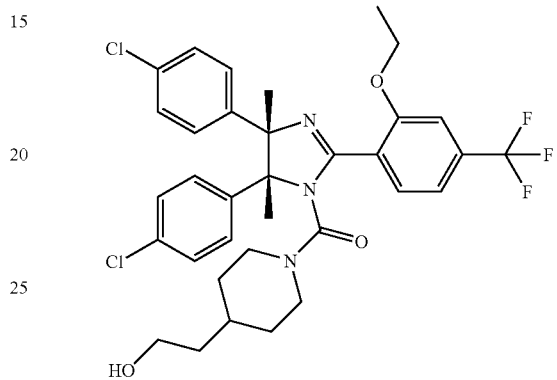

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with piperidin-4-yl-ethanol (Aldrich) to give the title compound. HR-MS (ES, m/z) calculated for $C_{34}H_{37}N_3O_3F_3Cl_2$ [(M+H)$^+$] 662.2159, observed 662.2158.

EXAMPLE 134 rac-1-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperidine-4-carboxylic acid amide

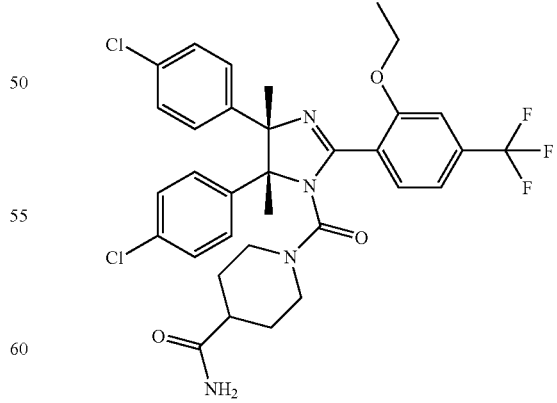

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with piperidine-4-car-

EXAMPLE 135 rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid bis-(2-hydroxy-ethyl)-amide

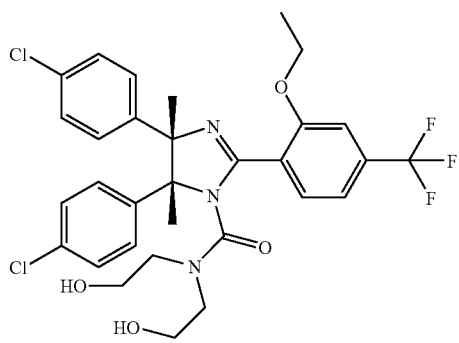

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with bis-(2-hydroxyethyl)-amine (Sigma) to give the title compound. HR-MS (ES, m/z) calculated for $C_{31}H_{33}N_3O_4F_3Cl_2$ $[(M+H)^+]$ 638.1795, observed 638.1797.

EXAMPLE 136 rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (2,3-dihydroxy-propyl)-amide

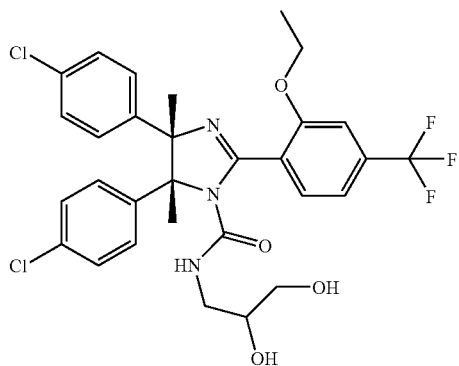

In a manner analogous to the method described in example 5, rac-(4S*,5R*)-4,5-bis-(4-chloro-phenyl)-2-(2-ethoxy-4-trifluoromethyl-phenyl)-4,5-dimethyl-4,5-dihydro-imidazole-1-carbonyl chloride was reacted with 3-amino-propane-1,2-diol (Aldrich) to give the title compound as a mixture of diastereomers. HR-MS (ES, m/z) calculated for $C_{30}H_{31}N_3O_4F_3Cl_2$ $[(M+H)^+]$ 624.1638, observed 624.1641.

EXAMPLE 137

3-{4-[4,5-Bis-(4-chloro-phenyl)-4,5-dimethyl-4,5-dihydro-1H-imidazol-2-yl]-3-ethoxy-phenyl}-3-methyl-butan-2-one

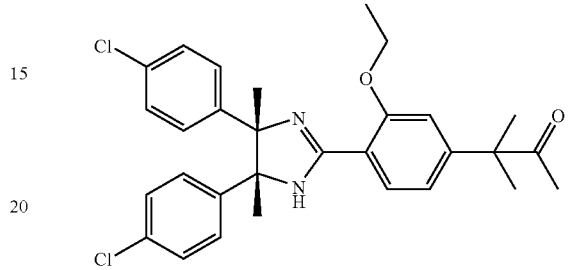

Sodium hydride (3.65 g, 91.347 mmol, 60% in mineral oil, Aldrich) was added to a round bottom flask and washed with hexane. Tetrahydrofuran (80 mL) was then added. To a suspension of sodium hydride in tetrahydrofuran cooled to 0° C. was added a solution of 1-(3-methoxy-phenyl)-propan-2-one (6 g, 36.539 mmol, Lancaster) in 1 mL of tetrahydrofuran. The ice bath was removed, and the mixture was stirred at room temperature for 30 min. Methyl iodide (6.82 mL, 109.6 mmol, Aldrich) was added at 0° C., and the mixture was stirred at room temperature for 48 h. The reaction was quenched with saturated solution of ammonium chloride and taken in water and ethyl acetate. The product was extracted with ethyl acetate (1×). The organic layers were washed with brine (1×), dried over anhydrous sodium sulfate and concentrated. The residue was purified by flash column chromatography (40 g of silica gel, eluting with 3-5% ethyl acetate in hexane) to give 3-(3-methoxy-phenyl)-3-methyl-butan-2-one as clear oil (6.603 g, 94%).

To a solution of 3-(3-methoxy-phenyl)-3-methyl-butan-2-one (6.570 g, 34.172 mmol) in methylene chloride (100 mL) cooled to −78° C. was added boron tribromide (102 mL, 1 M solution in methylene chloride, Aldrich). The mixture was stirred at −78° C. for 1 h, warmed up to 0° C. for 1 h then put in the freezer (−20° C.) for 72 h. At 0° C., water was added to quench the excess boron tribromide (CAUTION: Violent reaction). The product was extracted with petroleum ether. The organic layers were washed with brine, dried over anhydrous sodium sulfate and concentrated. The crude residue was purified by flash chromatography (40 g of silica gel, eluting with 5-20% ethyl acetate in hexane) to give 3-(3-hydroxy-phenyl)-3-methyl-butan-2-one as a yellow oil (5 g, 82%).

The mixture of 3-(3-hydroxy-phenyl)-3-methyl-butan-2-one (3.4 g, 19.08 mmol), diisopropylamine (16.7 mL, 95.4 mmoL) and ethyl iodide (6.2 mL, 76.32 mmol) in 60 mL of ethanol was heated at refluxed overnight. Thin layer chromatography still showed starting material. Potassium carbonate (9 g) was added, and the mixture was heated at reflux for 12 h.

It was concentrated in vacuo, and the residue was taken in ethyl acetate. After being washed with water and brine, the organic layer was dried over anhydrous sodium sulfate. The solids were filtered off, and the filtrate was concentrated to give 3.727 g of 3-(3-ethoxy-phenyl)-3-methyl-butan-2-one as light brown oil. It was used without further purification.

To a solution of 3-(3-ethoxy-phenyl)-3-methyl-butan-2-one (3.720 g, 18.03 mmol) in acetonitrile (40 mL) was added N-iodosuccinimide (5.679 g, 25.24 mmol) and trifluoroacetic acid (0.7 mL, 9.02 mmol) with stirring under argon. The reaction mixture was stirred at room temperature for 10 min then at 50° C. for 1 h. Upon cooling to room temperature, it was diluted with 10% ethyl acetate in hexane and filtered through a bed of Celite and silica gel. The filtrate was washed with water (1×), saturated solution of sodium bicarbonate (1×), 5% solution of sodium thiosulfate (1×), brine (1×), dried over anhydrous sodium sulfate and concentrated in vacuo. Purification of the crude residue by flash chromatography (330 g of silica gel, eluting with 30% ethyl acetate in hexane over 30 min) gave 4.83 g of 3-(3-ethoxy-4-iodo-phenyl)-3-methyl-butan-2-one as off-white solid.

To a dry pressure tube were added with stirring anhydrous acetonitrile (10 mL), 3-(3-ethoxy-4-iodo-phenyl)-3-methyl-butan-2-one (450 mg, 1.35 mmol), diphenylpropylphosphine (77 mg, 0.34 mmol) and triethylamine (470 uL, 3.37 mmol), respectively. Argon was bubbled through the solution for 10 min then palladium acetate (76 mg, 0.34 mmol) was added. The system was evacuated under high vacuum and refilled with carbon monoxide (40 psi). After 10 min, trihexylsilane (960 uL, 2.7 mmol) was added. The system was recharged with carbon monoxide (60 psi) and stirred at 60° C. overnight. The reaction mixture was concentrated in vacuo, and the residue was taken in ethyl acetate. It was filtered through a short silica gel plug. The filtrate was washed with water (2×), brine (1×), dried over anhydrous sodium sulfate. The solids were filtered off, and the filtrate was concentrated in vacuo. The crude residue was purified by flash chromatography (80 g of silica gel, eluting with 10-30% ethyl acetate in hexane over a period of 35 min) to give 150 mg of 4-(1,1-dimethyl-2-oxo-propyl)-2-ethoxy-benzaldehyde.

To a solution of 4-(1,1-dimethyl-2-oxo-propyl)-2-ethoxy-benzaldehyde (145 mg, 0.62 mmol) in anhydrous 1,2-dichloroethane (2 mL) cooled to 0° C. was added meso-2,3-bis-(4-chlorophenyl)-2,3-butanediamine (191 mg, 0.62 mmol). The mixture was stirred at room temperature for 4 d. N-bromosuccinimide (x mg, x mmol) was added at 0° C. and the mixture was stirred at room temperature for 1.5 h. Saturate solution of sodium carbonate was added to make it basic, and the product was extracted with ethyl acetate. The organic layers were dried over anhydrous sodium sulfate and concentrated in vacuo. The crude residue was purified by flash chromatography (45 g of silica gel, eluting with 0-30% ethyl acetate in hexane over a period of 25 min) to give 217 mg of the title product as light yellow solid.

EXAMPLE 138 rac-(4S*,5R*)-4,5-Bis-(4-chloro-phenyl)-2-[4-(1,1-dimethyl-2-oxo-propyl)-2-ethoxy-phenyl]-4,5-dimethyl-4,5-dihydro-imidazole-1-carbonyl chloride

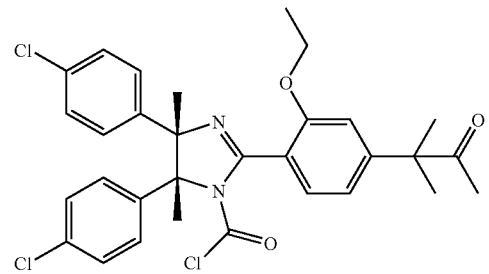

In a manner analogous to the method described in example 3, 3-{4-[4,5-bis-(4-chloro-phenyl)-4,5-dimethyl-4,5-dihydro-1H-imidazol-2-yl]-3-ethoxy-phenyl}-3-methyl-butan-2-one was reacted with phosgene in the presence of triethylamine to give the title compound.

EXAMPLE 139

3-(4-{4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-3-methyl-butan-2-one

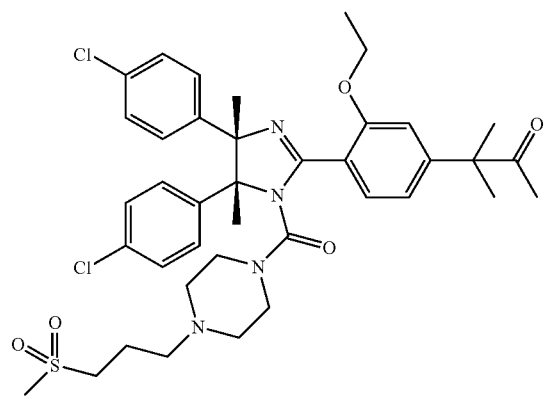

In a manner analogous to the method described in example 5, rac-(4S*,5R*)-4,5-bis-(4-chloro-phenyl)-2-[4-(1,1-dimethyl-2-oxo-propyl)-2-ethoxy-phenyl]-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title product as a racemic mixture. The enantiomers were then separated by supercritical fluid chromatography (Berger Instrument Multi-Gram II, Daicel ChiralPak OD-H 3×25 cm, 35° C. at 100 bar, eluting with 25% methanol in carbon dioxide). HR-MS (ES, m/z) calculated for $C_{39}H_{49}N_4O_5SCl_2$ [(M+H)$^+$] 775.2795, observed 775.2795.

EXAMPLE 140

3-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-3-methyl-butan-2-one

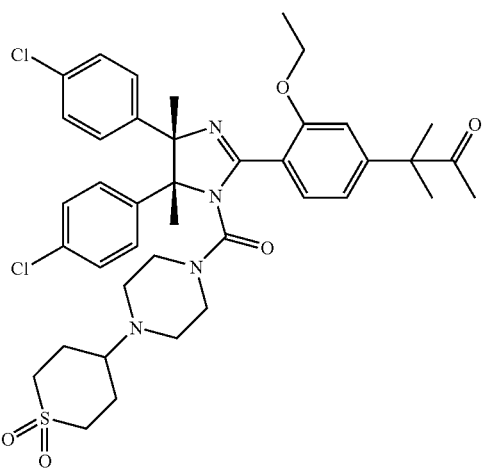

In a manner analogous to the method described in example 5, rac-(4S*,5R*)-4,5-bis-(4-chloro-phenyl)-2-[4-(1,1-dimethyl-2-oxo-propyl)-2-ethoxy-phenyl]-4,5-dimethyl-4,5-dihydro-imidazole-1-carbonyl chloride was reacted with 1-(1,1-dioxo-tetrahydro-2H-thiopyran-4-yl)-piperazine dihydrochloride (example 22) to give the title product as a racemic mixture. The enantiomers were then separated by supercritical fluid chromatography (Berger Instrument Multi-Gram II, Daicel ChiralPak OD-H 3×25 cm, 35° C. at 100 bar, eluting with 35% methanol in carbon dioxide). HR-MS (ES, m/z) calculated for $C_{40}H_{49}N_4O_5SCl_2$ [(M+H)$^+$] 767.2795, observed 767.2790.

EXAMPLE 141

2-(4-{(4S,5R)-4,5-Bis-(4-chloro-phenyl)-2-[4-(11,1-dimethyl-2-oxo-propyl)-2-ethoxy-phenyl]-4,5-dimethyl-4,5-dihydro-imidazole-1-carbonyl}-piperazin-1-yl)-acetamide

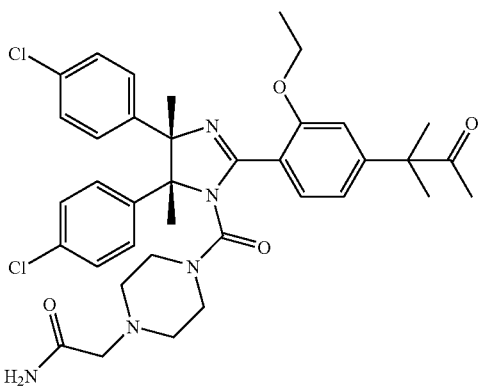

In a manner analogous to the method described in example 5, rac-(4S*,5R*)-4,5-bis-(4-chloro-phenyl)-2-[4-(1,1-dimethyl-2-oxo-propyl)-2-ethoxy-phenyl]-4,5-dimethyl-4,5-dihydro-imidazole-1-carbonyl chloride was reacted with 2-piperazin-1-yl-acetamide dihydrochloride (Matrix Scientific) to give the title product as a racemic mixture. The enantiomers were then separated by supercritical fluid chromatography (Berger Instrument Multi-Gram II, Daicel ChiralPak OD-H 3×25 cm, 35° C. at 100 bar, eluting with 30% methanol in carbon dioxide). HR-MS (ES, m/z) calculated for $C_{37}H_{44}N_5O_4Cl_2$ [(M+H)$^+$] 692.2765, observed 692.2762.

EXAMPLE 142 rac-(4S*,5R*)-2-(4-tert-Butyl-2-isopropoxy-phenyl)-4,5-bis-(4-chloro-phenyl)-4,5-dimethyl-4,5-dihydro-1H-imidazole

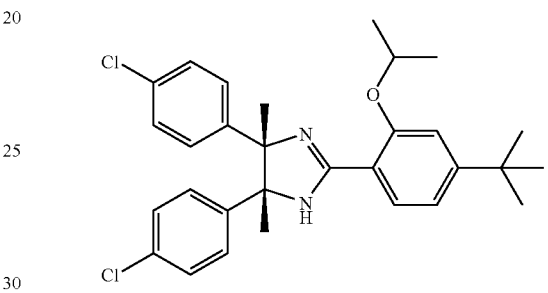

In a manner analogous to the method described in example 2, meso-2,3-bis-(4-chlorophenyl)-2,3-butanediamine was reacted with 4-tert-butyl-2-isopropoxy-benzoic acid methyl ester (prepared from 3-tert-butyl-phenol and isopropyl iodide as described in Fotouhi, N. et al. WO 2005110996) in the presence of trimethylaluminum to give the title compound. HR-MS (ES, m/z) calculated for $C_{30}H_{35}N_2OCl_2$ [(M+H)$^+$] 509.2121, observed 509.2121.

EXAMPLE 143 rac-(4S*,5R*)-2-(4-tert-Butyl-2-isopropoxy-phenyl)-4,5-bis-(4-chloro-phenyl)-4,5-dimethyl-4,5-dihydro-imidazole-1-carbonyl chloride

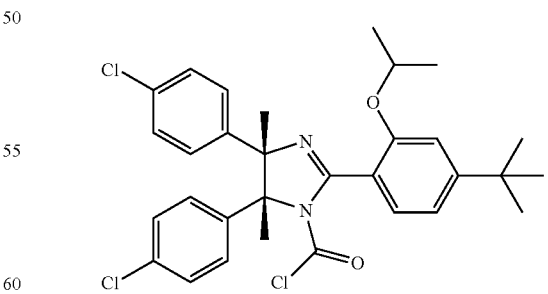

In a manner analogous to the method described in example 3, rac-(4S*,5R*)-2-(4-tert-butyl-2-isopropoxy-phenyl)-4,5-bis-(4-chloro-phenyl)-4,5-dimethyl-4,5-dihydro-1H-imidazole was reacted with phosgene in the presence of triethylamine to give the title compound.

EXAMPLE 144 rac-1-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-ethanone

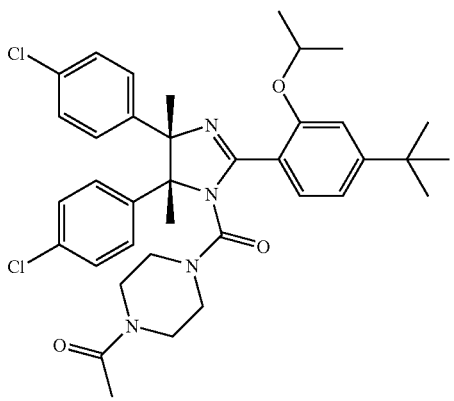

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-acetyl-piperazine (Aldrich) to give the title compound. HR-MS (ES, m/z) calculated for $C_{37}H_{55}N_4O_3Cl_2$ [(M+H)$^+$] 663.2863, observed 663.2857.

EXAMPLE 145 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(4-isopropyl-piperazin-1-yl)-methanone

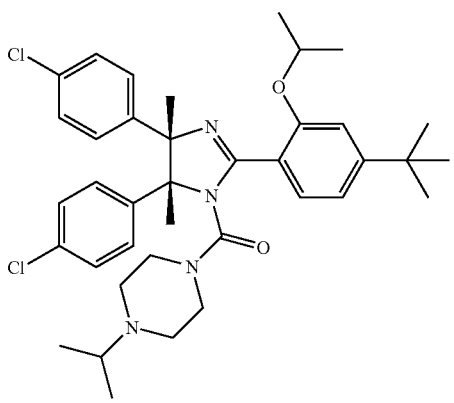

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-isopropyl-piperazine (Aldrich) to give the title compound. HR-MS (ES, m/z) calculated for $C_{38}H_{49}N_4O_2Cl_2$ [(M+H)$^+$] 663.3227, observed 663.3228.

EXAMPLE 146 rac-4-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-butyronitrile

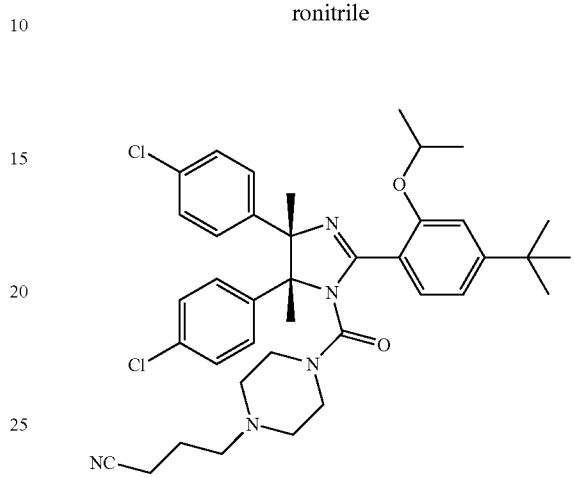

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 4-piperazin-1-yl-butyronitrile (Aldrich) to give the title compound. HR-MS (ES, m/z) calculated for $C_{39}H_{48}N_5O_2Cl_2$ [(M+H)$^+$] 688.3180, observed 688.3186.

EXAMPLE 147 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(3-methoxy-propyl)-piperazin-1-yl]-methanone

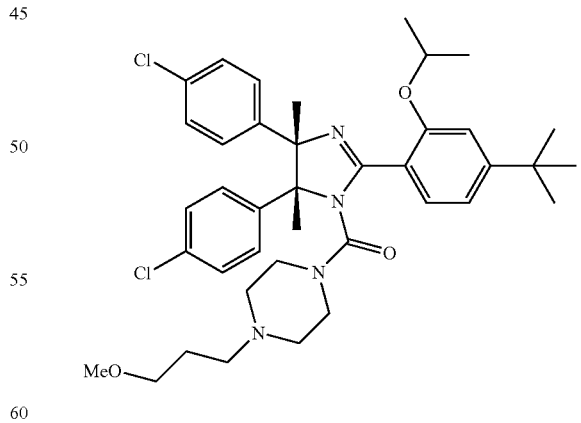

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-(3-methoxy-propyl)-piperazine (Aldrich) to give the title compound. HR-MS (ES, m/z) calculated for $C_{39}H_{51}N_4O_3Cl_2$ [(M+H)$^+$] 693.3333, observed 693.3334.

EXAMPLE 148 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-morpholin-4-yl-ethyl)-piperazin-1-yl]-methanone

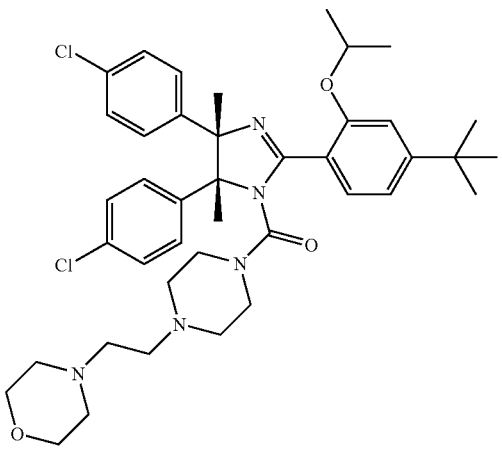

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 4-(2-piperazin-1-yl-ethyl)-morpholine (Aldrich) to give the title compound. HR-MS (ES, m/z) calculated for $C_{41}H_{54}N_5O_3Cl_2$ [(M+H)$^+$] 734.3598, observed 734.3600.

EXAMPLE 149 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(tetrahydro-furan-2-ylmethyl)-piperazin-1-yl]-methanone

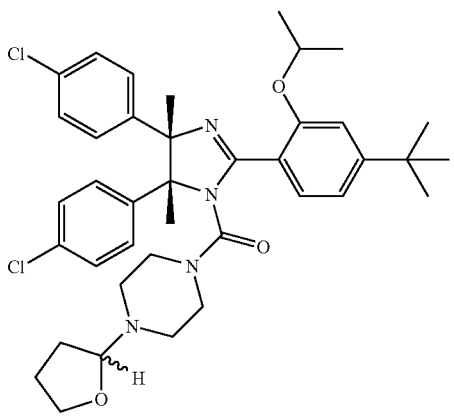

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-(tetrahydro-furan-2-ylmethyl)-piperazine (Aldrich) to give the title compound as a mixture of diastereomers. HR-MS (ES, m/z) calculated for $C_{40}H_{51}N_4O_3Cl_2$ [(M+H)$^+$] 705.3333, observed 705.3332.

EXAMPLE 150 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(hexahydro-pyrrolo[1,2-a]pyrazin-2-yl)-methanone

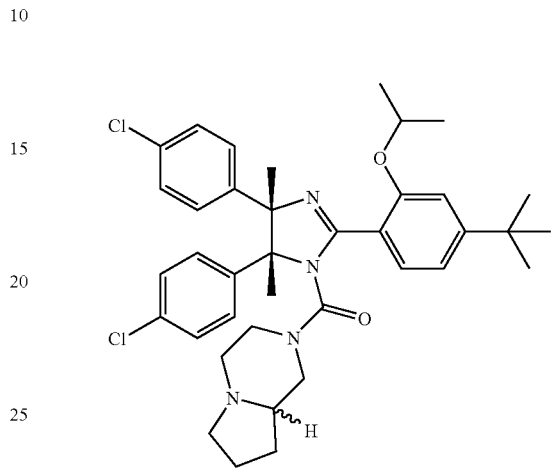

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with octahydro-pyrrolo[1,2-a]pyrazine (Aldrich) to give the title compound. HR-MS (ES, m/z) calculated for $C_{38}H_{47}N_4O_3Cl_2$ [(M+H)$^+$] 661.3071, observed 661.3073.

EXAMPLE 151 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(octahydro-pyrido[1,2-a]pyrazin-2-yl)-methanone

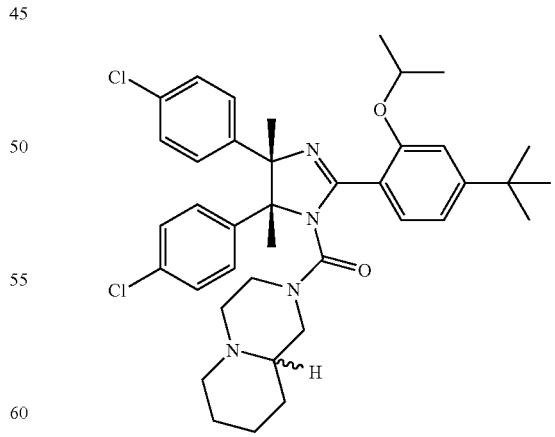

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with octahydro-pyrido[1,2-a]pyrazine (Aldrich) to give the title compound as a mixture

EXAMPLE 152 rac-(4S*,5R*)-2-(4-tert-Butyl-2-isopropoxy-phenyl)-4,5-bis-(4-chloro-phenyl)-4,5-dimethyl-4,5-dihydro-imidazole-1-carboxylic acid bis-(2-methoxy-ethyl)-amide

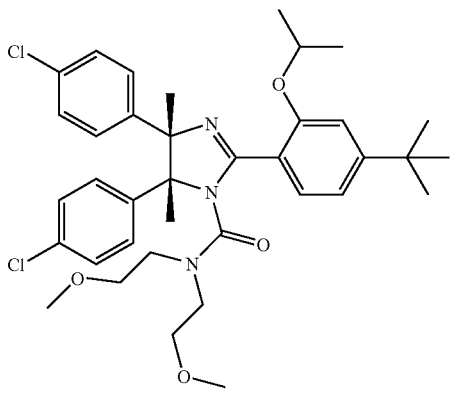

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with bis-(2-methoxyethyl)-amine (Aldrich) to give the title compound. HR-MS (ES, m/z) calculated for $C_{37}H_{49}N_4O_5SCl_2$ [(M+H)$^+$] 668.3017, observed 668.3010.

EXAMPLE 153 rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-methoxy-ethyl)-piperazin-1-yl]-methanone

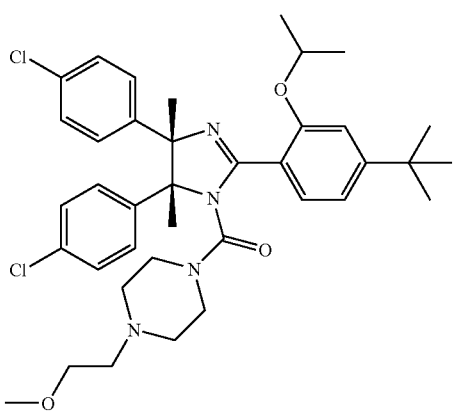

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-(2-methoxy-ethyl)-piperazine (Aldrich) to give the title compound. HR-MS (ES, m/z) calculated for $C_{38}H_{49}N_4O_3Cl_2$ [(M+H)$^+$] 679.3176, observed 679.3180.

of diastereomers. HR-MS (ES, m/z) calculated for $C_{39}H_{49}N_4O_2Cl_2$ [(M+H)$^+$] 675.3227, observed 675.3224.

EXAMPLE 154

[(4S,5R)-2-(4-tert-Butyl-2-isopropoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone

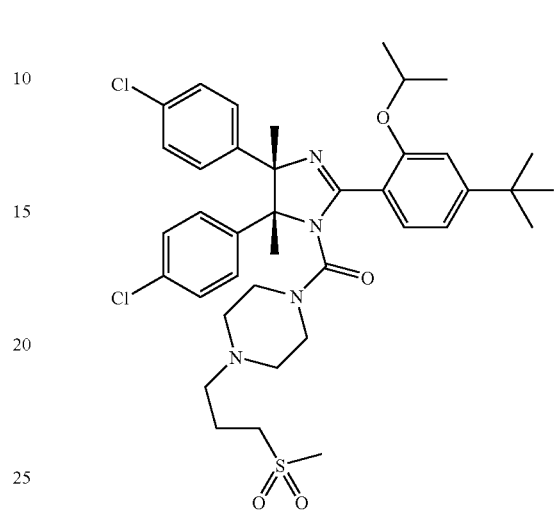

In a manner analogous to the method described in example 5, rac-(4S*,5R*)-2-(4-tert-butyl-2-isopropoxy-phenyl)-4,5-bis-(4-chloro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 25% isopropanol in carbon dioxide) gave the title compound. HR-MS (ES, m/z) calculated for $C_{39}H_{51}N_4O_4SCl_2$ [(M+H)$^+$] 741.3003, observed 741.2998.

EXAMPLE 155

[(4S,5R)-4,5-Bis-(4-chloro-phenyl)-2-(2-ethoxy-4-isopropyl-phenyl)-4,5-dimethyl-4,5-dihydro-imidazol-1-yl]-[4-(3-methanesulfonyl-propyl)-piperazin-1-yl]-methanone

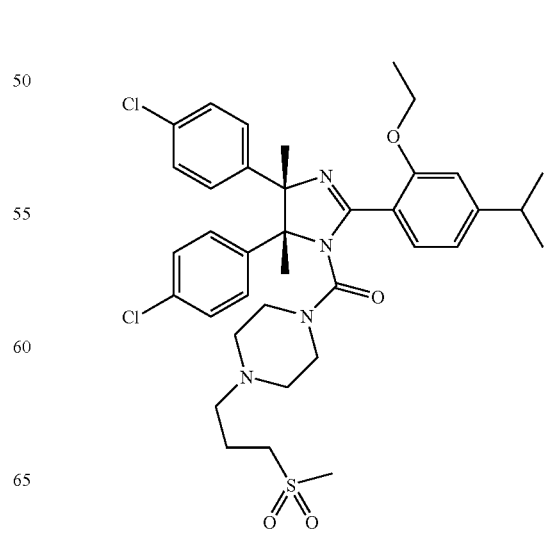

rac-(4S*,5R*)-4,5-Bis-(4-chloro-phenyl)-2-(2-ethoxy-4-isopropyl-phenyl)-4,5-dimethyl-4,5-dihydro-1H-imidazole was prepared from 2-ethoxy-4-isopropyl-benzoyl chloride (prepared from 2-hydroxy-4-isopropyl-benzoic acid in 3 steps) and meso-2,3-bis-(4-chlorophenyl)-2,3-butanediamine (example 1) in an analogous manner as described in example 2 (method 1).

rac-(4S*,5R*)-4,5-Bis-(4-chloro-phenyl)-2-(2-ethoxy-4-isopropyl-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(2-ethoxy-4-isopropyl-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OJ-H 3×25 cm, 35° C. at 100 bar, eluting with 15% of 1:1 ethanol/acetonitrile in carbon dioxide) gave the title compound. HR-MS (ES, m/z) calculated for $C_{37}H_{47}N_4O_4SCl_2$ [(M+H)$^+$] 713.2690, observed 713.2692.

EXAMPLE 156

[(4S,5R)-2-(5-tert-Butyl-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone

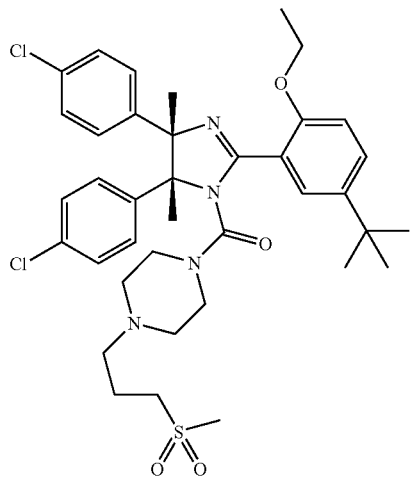

rac-(4S,5R*)-2-(5-tert-butyl-2-ethoxy-phenyl)-4,5-bis-(4-chloro-phenyl)-4,5-dimethyl-4,5-dihydro-1H-imidazole was prepared from 5-tert-butyl-2-ethoxy-benzoyl chloride (prepared from 5-tert-butyl-2-hydroxy-benzoic acid) and meso-2,3-bis-(4-chlorophenyl)-2,3-butanediamine (example 1) in an analogous manner as described in example 2 (method 1).

rac-(4S*,5R*)-2-(5-tert-butyl-2-ethoxy-phenyl)-4,5-bis-(4-chloro-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-2-(5-tert-butyl-2-ethoxy-phenyl)-4,5-bis-(4-chloro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 20% of 1:1 ethanol/acetonitrile in carbon dioxide) gave the title compound. HR-MS (ES, m/z) calculated for $C_{38}H_{49}N_4O_4SCl_2$ [(M+H)$^+$] 727.2846, observed 727.2847.

EXAMPLE 157

[(4S,5R)-4,5-Bis-(4-chloro-phenyl)-2-(2-ethoxy-5-methanesulfonyl-phenyl)-4,5-dimethyl-4,5-dihydro-imidazol-1-yl]-[4-(3-methanesulfonyl-propyl)-piperazin-1-yl]-methanone

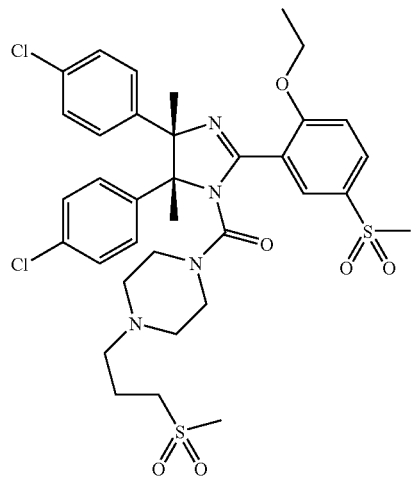

rac-(4S*,5R*)-4,5-bis-(4-chloro-phenyl)-2-(2-ethoxy-5-methanesulfonyl-phenyl)-4,5-dimethyl-4,5-dihydro-1H-imidazole was prepared from 2-ethoxy-5-methanesulfonyl-benzoyl chloride (prepared from 2-ethoxy-benzoic acid in an analogous as described in example 59) and meso-2,3-bis-(4-chlorophenyl)-2,3-butanediamine (example 1) in an analogous manner as described in example 2 (method 1).

rac-(4S*,5R*)-4,5-bis-(4-chloro-phenyl)-2-(2-ethoxy-5-methanesulfonyl-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(2-ethoxy-5-methanesulfonyl-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 25% of 1:1 ethanol/acetonitrile in carbon dioxide) gave the title compound. HR-MS (ES, m/z) calculated for $C_{35}H_{43}N_4O_6S_2Cl_2$ [(M+H)$^+$] 749.1996, observed 749.1991.

EXAMPLE 158

[(4S,5R)-4,5-Bis-(4-chloro-phenyl)-2-(2-ethoxy-4-methanesulfonyl-phenyl)-4,5-dimethyl-4,5-dihydro-imidazol-1-yl]-[4-(3-methanesulfonyl-propyl)-piperazin-1-yl]-methanone

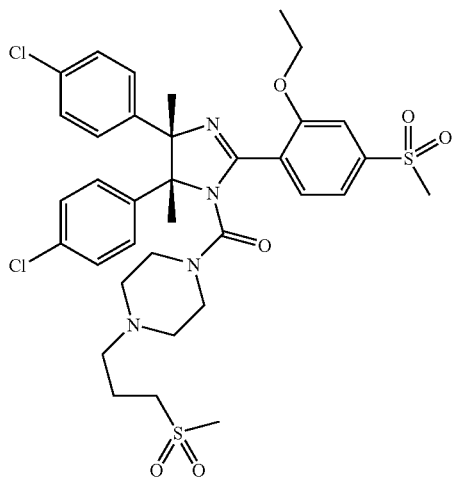

rac-(4S*,5R*)-4,5-Bis-(4-chloro-phenyl)-2-(2-ethoxy-4-methanesulfonyl-phenyl)-4,5-dimethyl-4,5-dihydro-1H-imidazole was prepared from 2-ethoxy-4-methanesulfonyl-benzoyl chloride (prepared from ethyl 2-ethoxy-4-fluoro-benzoate and sodium thiomethoxide in 4 steps) and meso-2,3-bis-(4-chlorophenyl)-2,3-butanediamine (example 1) in an analogous manner as described in example 2 (method 1).

rac-(4S*,5R*)-4,5-Bis-(4-chloro-phenyl)-2-(2-ethoxy-4-methanesulfonyl-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(2-ethoxy-4-methanesulfonyl-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 30% methanol in carbon dioxide) gave the title compound. HR-MS (ES, m/z) calculated for $C_{35}H_{43}N_4O_6S_2Cl_2$ [(M+H)$^+$] 749.1996, observed 749.1995.

EXAMPLE 159

[(4S,5R)-4,5-Bis-(4-chloro-phenyl)-2-(4-cyclopropyl-2-ethoxy-phenyl)-4,5-dimethyl-4,5-dihydro-imidazol-1-yl]-[4-(3-methanesulfonyl-propyl)-piperazin-1-yl]-methanone

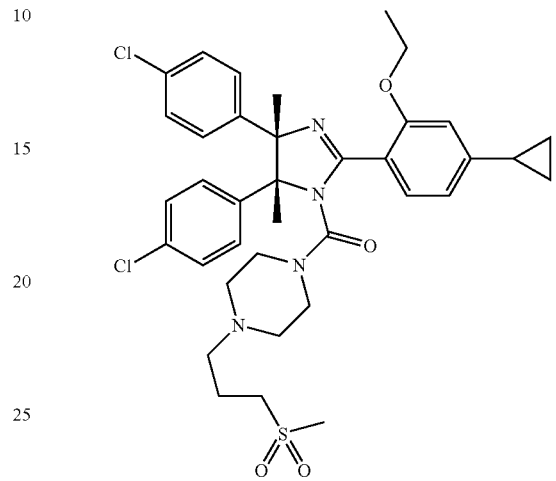

rac-(4S*,5R*)-4,5-Bis-(4-chloro-phenyl)-2-(4-cyclopropyl-2-ethoxy-phenyl)-4,5-dimethyl-4,5-dihydro-1H-imidazole was prepared from 4-cyclopropyl-2-ethoxy-benzoyl chloride (prepared from 4-bromo-2-hydroxy-benzoic acid by alkylation with iodoethane, Suzuki coupling with cyclopropyl boronic acid, then saponification and conversion to the chloride) and meso-2,3-bis-(4-chlorophenyl)-2,3-butanediamine (example 1) in an analogous manner as described in example 2 (method 1).

rac-(4S*,5R*)-4,5-Bis-(4-chloro-phenyl)-2-(4-cyclopropyl-2-ethoxy-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(4-cyclopropyl-2-ethoxy-phenyl)-4,5-dimethyl-4,5-dihydro-imidazole-1-carbamoyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 30% methanol in carbon dioxide) gave the title compound. HR-MS (ES, m/z) calculated for $C_{37}H_{44}N_4O_4SCl_2$ [(M+H)$^+$] 711.2533, observed 711.2533.

EXAMPLE 160

[(4S,5R)-4,5-Bis-(4-chloro-phenyl)-2-(5-cyclopropyl-2-ethoxy-phenyl)-4,5-dimethyl-4,5-dihydro-imidazol-1-yl]-[4-(3-methanesulfonyl-propyl)-piperazin-1-yl]-methanone

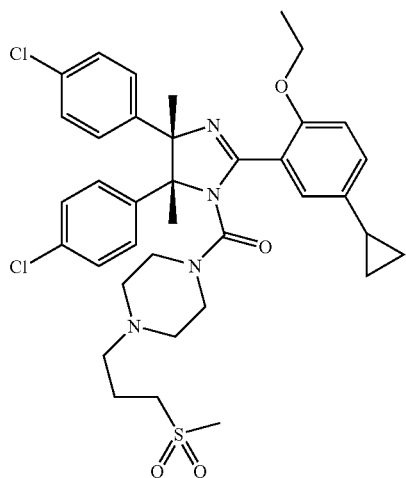

rac-(4S*,5R*)-4,5-Bis-(4-chloro-phenyl)-2-(5-cyclopropyl-2-ethoxy-phenyl)-4,5-dimethyl-4,5-dihydro-1H-imidazole was prepared from 5-cyclopropyl-2-ethoxy-benzoyl chloride (prepared from 5-bromo-2-hydroxy-benzoic acid by alkylation with iodoethane, Suzuki coupling with cyclopropyl boronic acid, then saponification and conversion to the chloride) and meso-2,3-bis-(4-chlorophenyl)-2,3-butanediamine (example 1) in an analogous manner as described in example 2 (method 1).

rac-(4S*,5R*)-4,5-Bis-(4-chloro-phenyl)-2-(5-cyclopropyl-2-ethoxy-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(5-cyclopropyl-2-ethoxy-phenyl)-4,5-dimethyl-4,5-dihydro-imidazole1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 30% isopropanol in carbon dioxide) gave the title compound. HR-MS (ES, m/z) calculated for $C_{37}H_{44}N_4O_4SCl_2$ [(M+H)$^+$] 711.2533, observed 711.2536.

EXAMPLE 161

[(4S,5R)-4,5-Bis-(4-chloro-phenyl)-2-(4-ethanesulfonyl-2-ethoxy-phenyl)-4,5-dimethyl-4,5-dihydro-imidazol-1-yl]-[4-(3-methanesulfonyl-propyl)-piperazin-1-yl]-methanone

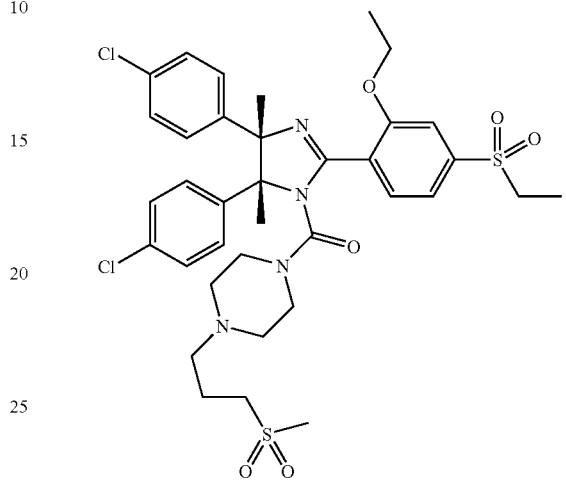

rac-(4S*,5R*)-4,5-bis-(4-chloro-phenyl)-2-(4-ethanesulfonyl-2-ethoxy-phenyl)-4,5-dimethyl-4,5-dihydro-1H-imidazole was prepared from 4-ethanesulfonyl-2-ethoxy-benzoyl chloride (prepared from ethyl 2-ethoxy-4-fluoro-benzoate and sodium ethanethiolate) and meso-2,3-bis-(4-chlorophenyl)-2,3-butanediamine (example 1) in an analogous manner as described in example 2 (method 1).

rac-(4S*,5R*)-4,5-bis-(4-chloro-phenyl)-2-(4-ethanesulfonyl-2-ethoxy-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(4-ethanesulfonyl-2-ethoxy-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 30% methanol in carbon dioxide) gave the title compound. HR-MS (ES, m/z) calculated for $C_{36}H_{53}N_4O_4SCl_2$ [(M+H)$^+$] 763.2152, observed 763.2150.

EXAMPLE 162

[(4S,5R)-2-(4-tert-Butyl-2-ethoxy-phenyl)-4,5-bis-(4-chloro-phenyl)-4,5-diethyl-4,5-dihydro-imidazol-1-yl]-[4-(3-methanesulfonyl-propyl)-piperazin-1-yl]-methanone

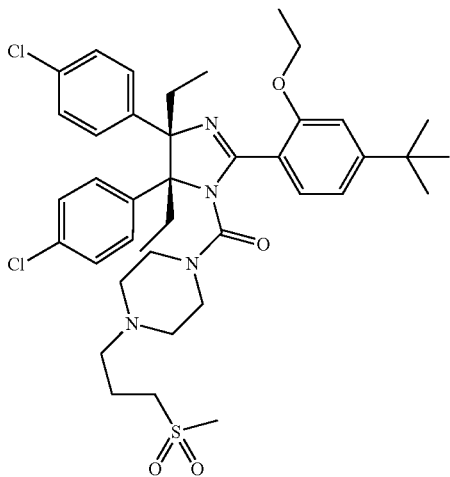

1-(4-Chlorophenyl)propan-1-one (8.4 g, 50 mmol) was combined with hydroxylamine hydrochloride (4.0 g, 58 mmol), pyridine (4.6 g, 58 mmol), and ethanol (75 mL). The mixture was refluxed for 3 h. Solvent was evaporated and the residue diluted with water and extracted into diethyl ether/hexane (1:1). The organic extracts were washed with water, brine, and dried over anhydrous magnesium sulfate. Crystallization from cold hexane gave 5.0 g of 1-(4-chlorophenyl)propan-1-one oxime.

1-(4-Chlorophenyl)propan-1-one oxime (5.0 g, 27.3 mmol) was dissolved in acetonitrile (200 mL) and zinc dust (8.8 g. 136 mmol) was added. With mechanical stirring at −15° C. methanesulfonic acid (13 g, 136 mmol) was added over 0.5 hr. Stirring was continued at room temperature for 16 h. Water (100 mL) was added with stirring and the mixture was filtered through Celite. Volatiles were evaporated and the aqueous portion was diluted with 3 N sodium hydroxide (100 mL). The mixture was extracted with diethyl ether (2×). The organic extracts were washed with water, brine, dried over anhydrous magnesium sulfate and concentrated. The crude residue was partially purified by flash chromatography to give ~2 g of a mixture of the threo and erythro isomers (8:1 ratio). Crystallization from diethyl ether/hexane gave pure threo isomer (1.4 g) and crystallization of the mother liquors gave erythro-3,4-bis-(4-chlorophenyl)hexane-3,4-diamine (310 mg, 90% purity).

rac-(4S*,5R*)-2-(4-tert-Butyl-2-ethoxy-phenyl)-4,5-bis-(4-chloro-phenyl)-4,5-diethyl-4,5-dihydro-1H-imidazole was prepared from 4-tert-butyl-2-ethoxy-benzoyl chloride and meso-3,4-bis-(4-chloro-phenyl)-hexane-3,4-diamine in an analogous manner as described in example 2 (method 1).

rac-(4S*,5R*)-2-(4-tert-Butyl-2-ethoxy-phenyl)-4,5-bis-(4-chloro-phenyl)-4,5-diethyl-4,5-dihydro-1H-imidazole was reacted with phosgene in the presence of triethylamine to give the corresponding carbamoyl chloride.

In a manner analogous to the method described in example 5, the carbamoyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 25% isopropanol in carbon dioxide) gave the title compound. HR-MS (ES, m/z) calculated for $C_{40}H_{53}N_4O_4SCl_2$ [(M+H)$^+$] 755.3159, observed 755.3157.

EXAMPLE 163

[(4S,5R)-4,5-Bis-(4-chloro-phenyl)-2-(2-ethoxy-4-ethylsulfanyl-phenyl)-4,5-dimethyl-4,5-dihydro-imidazol-1-yl]-[4-(3-methanesulfonyl-propyl)-piperazin-1-yl]-methanone

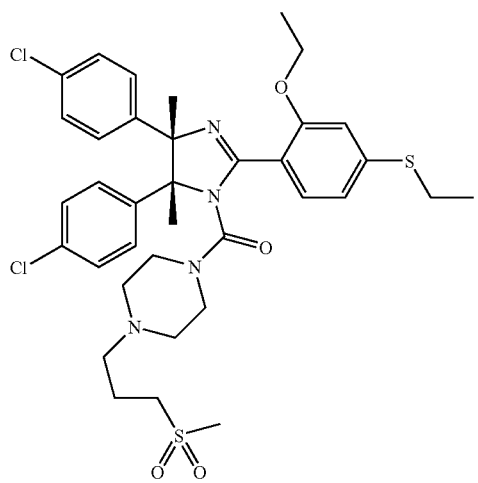

rac-(4S*,5R*)-4,5-bis-(4-chloro-phenyl)-2-(2-ethoxy-4-ethylsulfanyl-phenyl)-4,5-dimethyl-4,5-dihydro-1H-imidazole was prepared from 2-ethoxy-4-ethylsulfanyl-benzoyl chloride (prepared from ethyl 2-ethoxy-4-fluoro-benzoate and sodium ethanethiolate) and meso-2,3-bis-(4-chlorophenyl)-2,3-butanediamine (example 1) in an analogous manner as described in example 2 (method 1).

rac-(4S*,5R*)-4,5-bis-(4-chloro-phenyl)-2-(2-ethoxy-4-ethylsulfanyl-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-4,5-bis-(4-chloro-phenyl)-2-(2-ethoxy-4-ethylsulfanyl-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 35% methanol in carbon dioxide) gave the title compound. HR-MS (ES, m/z) calculated for $C_{36}H_{45}N_4O_4S_2Cl_2$ [(M+H)$^+$] 731.2254, observed 731.2259.

EXAMPLE 164

[(4S,5R)-2-(4-tert-Butyl-2-methoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone

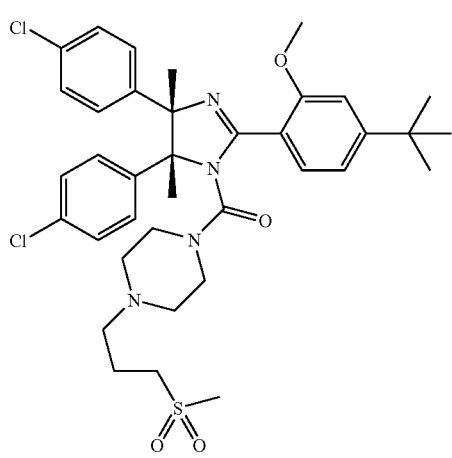

rac-(4S*,5R*)-2-(4-tert-butyl-2-methoxy-phenyl)-4,5-bis-(4-chloro-phenyl)-4,5-dimethyl-4,5-dihydro-1H-imidazole was prepared from 4-tert-butyl-2-methoxy-benzoyl chloride (prepared from 4-tert-butyl-2-hydroxy-benzoic acid) and meso-2,3-bis-(4-chlorophenyl)-2,3-butanediamine (example 1) in an analogous manner as described in example 2 (method 1).

rac-(4S*,5R*)-2-(4-tert-butyl-2-methoxy-phenyl)-4,5-bis-(4-chloro-phenyl)-4,5-dimethyl-4,5-dihydro-1H-imidazole was reacted with phosgene in the presence of triethylamine to give the corresponding carbamoyl chloride.

In a manner analogous to the method described in example 5, rac-(4S*,5R*)-2-(4-tert-butyl-2-methoxy-phenyl)-4,5-bis-(4-chloro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 35% methanol in carbon dioxide) gave the title compound. HR-MS (ES, m/z) calculated for $C_{37}H_{47}N_4O_4SCl_2$ [(M+H)$^+$] 713.2690, observed 713.2690.

EXAMPLE 165

[(4S,5R)-2-(4-Chloro-2-ethoxy-5-methanesulfonyl-phenyl)-4,5-bis-(4-chloro-phenyl)-4,5-dimethyl-4,5-dihydro-imidazol-1-yl]-[4-(1,1-dioxo-tetrahydro-2H-thiopyran-4-yl)-piperazin-1-yl]-methanone

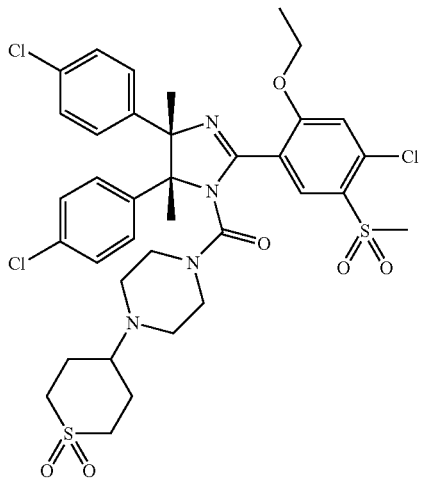

In a manner analogous to the method described in example 5, rac-(4S*,5R*)-2-(4-chloro-2-ethoxy-5-methanesulfonyl-phenyl)-4,5-bis-(4-chloro-phenyl)-4,5-dimethyl-4,5-dihydro-imidazole-1-carbonyl chloride (example 61) was reacted with 1-(1,1-dioxo-tetrahydro-2H-thiopyran-4-yl)-piperazine dihydrochloride (example 22) to give the title compound as a racemic mixture. The enantiomers were separated by supercritical fluid chromatography (Berger Instrument Multi-Gram II, Regis Technologies Whelk-01 3×25 cm, 35° C. at 100 bar, eluting with 40% methanol in carbon dioxide) gave the title compound. HR-MS (ES, m/z) calculated for $C_{36}H_{42}N_4O_6S_2Cl_3$ [(M+H)$^+$] 795.1606, observed 795.1605.

EXAMPLE 166

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(1,1-dioxo-tetrahydro-thiophen-3-yl)-piperazin-1-yl]-methanone In a manner analogous to the method described in example 5, rac-(4S*,5R*)-2-(4-tert-butyl-2-ethoxy-phenyl)-4,5-bis-(4-chloro-phenyl)-4,5-dimethyl-4,5-dihydro-1H-imidazole was reacted with 1-(1,1-dioxo-tetrahydro-thiophen-3-yl)-piperazine (Enamine-BB) to give the title compound as a racemic mixture. The enantiomers were separated by supercritical fluid chromatography (Berger Instrument Multi-Gram II, Daicel ChiralPak OJ-H 3×25 cm, 35° C. at 100 bar, eluting with 20% isopropanol in carbon dioxide) gave the title compound as a mixture of diastereomers. HR-MS (ES, m/z) calculated for $C_{38}H_{46}N_4O_4SCl_2$ [(M+H)$^+$] 725.2690, observed 725.2692.

EXAMPLE 167

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(3-ethanesulfonyl-propyl)-piperazin-1-yl]-methanone

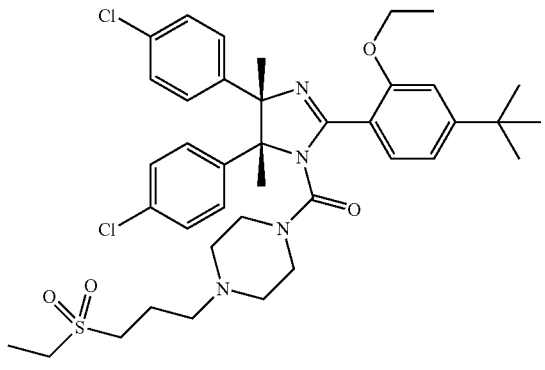

In a manner analogous to the method described in example 5, (4S,5R)-2-(4-tert-butyl-2-ethoxy-phenyl)-4,5-bis-(4-chloro-phenyl)-4,5-dimethyl-4,5-dihydro-1H-imidazole (example 4) was reacted with 1-(3-ethanesulfonyl-propyl)-piperazine dihydrochloride (prepared from 3-ethylsulfanyl-propan-1-ol in an analogous manner as the method described for 1-(3-methanesulfonyl-propyl)-piperazine dihydrochloride) to give the title compound. HR-MS (ES, m/z) calculated for $C_{39}H_{51}N_4O_4SCl_2$ [(M+H)$^+$] 741.3003, observed 741.2998.

EXAMPLE 168

2-(4-{(4S,5R)-4,5-Bis-(4-chloro-phenyl)-1-[4-(3-ethanesulfonyl-propyl)-piperazine-1-carbonyl]-4,5-dimethyl-4,5-dihydro-1H-imidazol-2-yl}-3-ethoxy-phenyl)-2-methyl-propionitrile

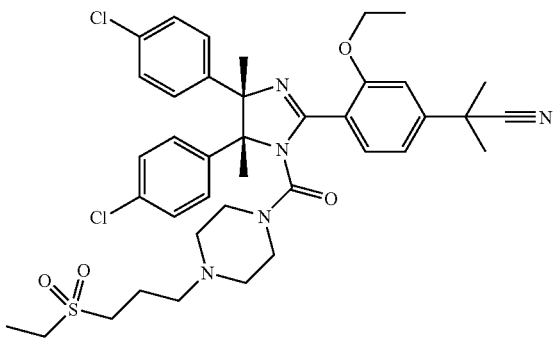

The enantiomers of rac-(4S*,5R*)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride (example 17) were separated by supercritical fluid chromatography (Berger Instrument Multi-Gram II, Daicel ChiralPak OD-H 3×25 cm, 35° C. at 100 bar, eluting with 18% acetonitrile in carbon dioxide).

In a manner analogous to the method described in example 5, (4S,5R)-4,5-bis-(4-chloro-phenyl)-2-[4-(cyano-dimethyl-methyl)-2-ethoxy-phenyl]-4,5-dimethyl-4,5-dihydro-imidazole-1-carbonyl chloride was reacted with 1-(3-ethanesulfonyl-propyl)-piperazine dihydrochloride (example 167) to give the title compound. HR-MS (ES, m/z) calculated for $C_{38}H_{48}N_5O_4SCl_2$ [(M+H)$^+$] 752.2799, observed 752.2799.

EXAMPLE 169

3,4-bis(4-chlorophenyl)-1,2,5-thiadiazole-1,1-dioxide

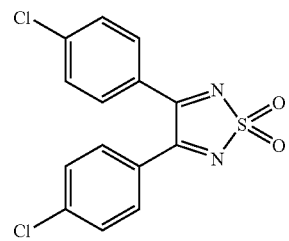

To a solution of 4-chlorobenzaldehyde (240 g, 1.707 mol) in 144 mL of methanol was added 2.40 g of potassium cyanide in 4.8 mL water over 6 min. The mixture was refluxed for another 50 min (mixture became deep red), cooled, then concentrated under reduced pressure. The red residue was taken up in 1500 mL of hexane-ethyl acetate (1:1), and washed successively with water (1×150 mL), 20% sodium bisulfite (6×150 mL), brine (1×150 mL) and dried over anhydrous sodium sulfate. After filtration and concentration under reduced pressure, the product was boiled in 400 mL of hexane to remove small amounts of 4-chlorobenzaldehyde. The mixture was cooled and the white solid was collected by suction filtration to give 183.94 g of 4,4'-dichlorobenzoin (76%). This procedure was adapted from Lutz et al. *J. Am. Chem. Soc.* 1949, 71, 478.

To a solution of 4,4'-dichlorobenzoin (183.94 g, 0.645 mol) in 1400 mL of ethyl acetate was added 109.785 g (0.687 mole) of bromine over 2 min. The mixture was stirred for 1.5 h during which time the dark bromine color lightened, and crystals came out of solution (use of mechanical stirrer is recommended). The mixture was cooled in ice bath for 10 min, and the solids were collected by suction filtration and washed with 800 mL of diethyl ether to give 149.01 g of 4,4'-dichlorobenzyl as yellow crystals (81%).

A mixture of 4,4'-dichlorobenzyl (55.824 g, 0.20 mol), sulfamide (24.028 g, 0.25 mol), triethylamine (8.36 mL, 0.06 mol) and absolute ethanol (1200 mL) was refluxed under argon for 18 h, then ~600 mL was distilled out and the remainder of the volatiles removed under reduced pressure. LC-MS indicated incomplete reaction, therefore additional amounts of sulfamide (4.806 g, 0.05 mol), triethylamine (8.36 mL, 0.06 mol) and absolute ethanol (1200 mL) were added. The mixture was refluxed under argon for 22 h. About ~600 mL of the volatiles was distilled out and the remainder was removed under reduced pressure. Additional acetonitrile was added and the mixture was again concentrated under reduced pressure. The residue was taken up in 1000 mL of ethyl acetate, washed successively with saturated sodium bicarbonate (1×250 mL), water (3×250 mL), brine (1×250 mL). The organic layer was dried over anhydrous sodium sulfate, filtered and concentrated under reduced pressure. The residue was evaporated again with acetonitrile, and then taken in 450 mL of diethyl ether and stirred for 30 min. The solids were collected by suction filtration to give 56.14 g of 3,4-bis-(4-chlorophenyl)-1,2,5-thiadiazole-1,1-dioxide as a tan solid (82%).

EXAMPLE 170 rac-(1R*,2S*)-1,2-Bis-(4-chloro-phenyl)-propane-1,2-diamine

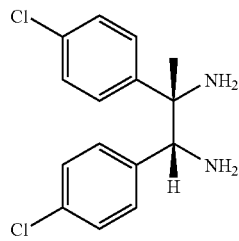

A solution of 5.0 g (14.7 mmol) of 3,4-bis-(4-chlorophenyl)-1,2,5-thiadiazole-1,1-dioxide in 55 mL of anhydrous tetrahydrofuran, under argon was cooled to 0° C. and then 12.9 mL of a 1.4 M solution (1:3 tetrahydrofuran-toluene) of methyl magnesium bromide was added dropwise over 5 min. The mixture was stirred for 35 min and then poured onto 100 g of ice plus 55 mL of 1 M hydrochloric acid. The mixture was taken up in 1000 mL of ethyl acetate, and the organic layer was washed with brine and then dried over anhydrous sodium sulfate. After filtration and concentration under reduced pressure, 5.38 g of 2,3-dihydro-3-methyl-3,4-bis(4-chlorophenyl)-1,2,5-thiadiazole-1,1-dioxide was obtained. This material was used directly in the next step without further purification.

To a solution of 3,4-bis-(4-chloro-phenyl)-3-methyl-2,3-dihydro-[1,2,5]thiadiazole 1,1-dioxide (5.38 g, 15.1 mmol) in 91 mL of in ethanol cooled to 0° C. was added sodium borohydride (0.30 g, 61 mmol) portionwise over 7 min. After stirring at 0° C. for another 45 min, the mixture was allowed to warm to room temperature and stirred for 3.5 h. The reaction was then cooled to 0° C. and quenched by dropwise addition of 1 M hydrochloric acid (38 mL). The reaction mixture was taken up in 500 mL of ethyl acetate then washed with water (300 mL) and brine (300 mL), dried over anhydrous sodium sulfate and concentrated. The crude residue was purified by flash column chromatography (silica gel, eluting with 3:1 heptane-ethyl acetate) to give rac-(3R*,4S*)-3,4-bis(4-chlorophenyl)-3-methyl-1,2,5-thiadiazolidine-1,1-dioxide (4.3 g).

A suspension of rac-(3R*,4S*)-3,4-bis(4-chlorophenyl)-3-methyl-1,2,5-thiadiazolidine-1,1-dioxide (3.71 g, 10.4 mmol) and phenol (4.86 g, 52 mmol) in 48% hydrobromic acid (13.56 mL) and acetic acid (46.44 mL) was stirred at 130° C. for 40 min (reaction progress monitored by TLC), then allowed to cool to room temperature. The crude reaction mixture was partitioned between ethyl acetate and water, and the aqueous phase washed twice with ethyl acetate. The aqueous phase was then made basic by the slow addition of solid sodium hydroxide (60 g; CARE! Exothermic) and extracted with diethyl ether (3×500 mL). The combined ethereal extracts were washed with 2M sodium hydroxide (100 mL), then dried over anhydrous sodium sulfate (with a few pellets of solid sodium hydroxide) and evaporated to give the title compound (1.56 g). This material was carried forward to the next step without any further purification.

EXAMPLE 171

(4S,5R)-2-(4-tert-Butyl-2-ethoxy-phenyl)-4,5-bis-(4-chloro-phenyl)-4-methyl-4,5-dihydro-1H-imidazole

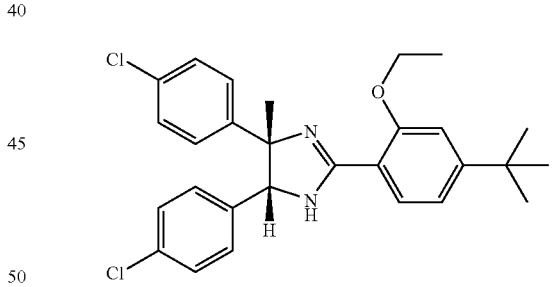

In a manner analogous to the method described in example 2, rac-(1R*,2S*)-1,2-bis-(4-chloro-phenyl)-propane-1,2-diamine was reacted with 4-tert-butyl-2-ethoxy-benzoic acid methyl ester (prepared as described in Fotouhi, N. et al. WO 2005110996) in the presence of trimethylaluminum to give the title compound as a racemic mixture.

The enantiomers were separated by supercritical fluid chromatography (Berger Instrument Multi-Gram II, Daicel ChiralPak OD-H 3×25 cm, 35° C. at 100 bar, eluting with 25% methanol and 0.2% isopropylamine in carbon dioxide) to give (4S,5R)-2-(4-tert-butyl-2-ethoxy-phenyl)-4,5-bis-(4-chloro-phenyl)-4-methyl-4,5-dihydro-1H-imidazole.

HR-MS (ES, m/z) calculated for $C_{28}H_{31}N_2OCl_2$ [(M+H)$^+$] 481.1808, observed 481.1801.

EXAMPLE 172 rac-(4S*,5R*)-2-(4-tert-Butyl-2-ethoxy-phenyl)-4,5-bis-(4-chloro-phenyl)-4-methyl-4,5-dihydro-imidazole-1-carbonyl chloride

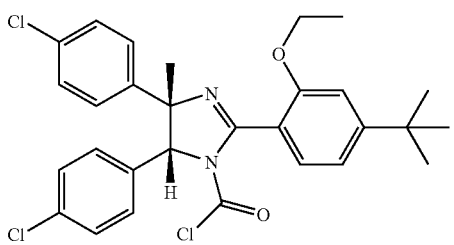

In a manner analogous to the method described in example 3, rac-(4S*,5R*)-2-(4-tert-butyl-2-ethoxy-phenyl)-4,5-bis-(4-chloro-phenyl)-4-methyl-4,5-dihydro-1H-imidazole was reacted with phosgene in the presence of triethylamine to give the title compound.

EXAMPLE 173

(4S,5R)-2-(4-tert-Butyl-2-ethoxy-phenyl)-4,5-bis-(4-chloro-phenyl)-4-methyl-4,5-dihydro-imidazole-1-carbonyl chloride

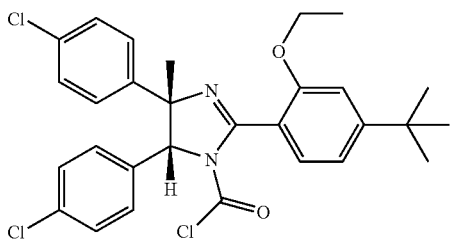

In a manner analogous to the method described in example 3, (4S,5R)-2-(4-tert-butyl-2-ethoxy-phenyl)-4,5-bis-(4-chloro-phenyl)-4-methyl-4,5-dihydro-1H-imidazole was reacted with phosgene in the presence of triethylamine to give the title compound.

EXAMPLE 174

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone

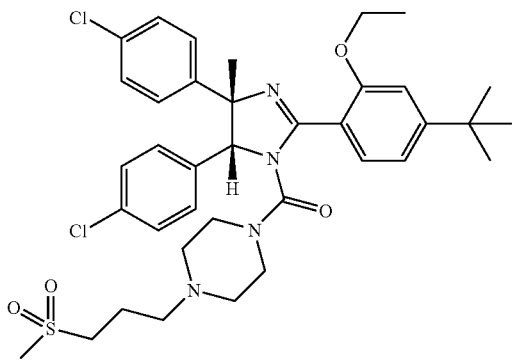

In a manner analogous to the method described in example 5, (4S,5R)-2-(4-tert-butyl-2-ethoxy-phenyl)-4,5-bis-(4-chloro-phenyl)-4-methyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound. HR-MS (ES, m/z) calculated for $C_{37}H_{47}N_4O_4SCl_2$ $[(M+H)^+]$ 713.2690, observed 713.2687.

EXAMPLE 175

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone

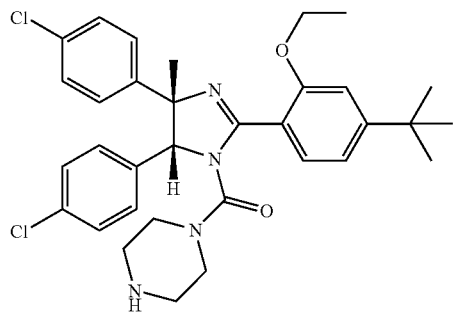

In a manner analogous to the method described in example 5, (4S,5R)-2-(4-tert-butyl-2-ethoxy-phenyl)-4,5-bis-(4-chloro-phenyl)-4-methyl-4,5-dihydro-imidazole-1-carbonyl chloride was reacted with piperazine (Aldrich) to give the title compound. LC-MS: 593.2 $[(M+H)^+]$

EXAMPLE 176

1-[(4S,5R)-2-(4-tert-Butyl-2-ethoxy-phenyl)-4,5-bis-(4-chloro-phenyl)-4-methyl-4,5-dihydro-imidazole-1-carbonyl]-piperidine-4-carboxylic acid amide

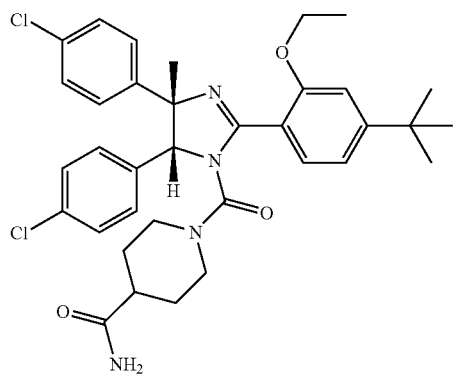

In a manner analogous to the method described in example 5, (4S,5R)-2-(4-tert-butyl-2-ethoxy-phenyl)-4,5-bis-(4-chloro-phenyl)-4-methyl-4,5-dihydro-imidazole-1-carbonyl chloride was reacted with 1-piperidin-4-yl-ethanone (Aldrich) to give the title compound. LC-MS: 635.2 $[(M+H)^+]$

EXAMPLE 177

1-{4-[(4S,5R)-2-(4-tert-Butyl-2-ethoxy-phenyl)-4,5-bis-(4-chloro-phenyl)-4-methyl-4,5-dihydro-imidazole-1-carbonyl]-piperazin-1-yl}-ethanone

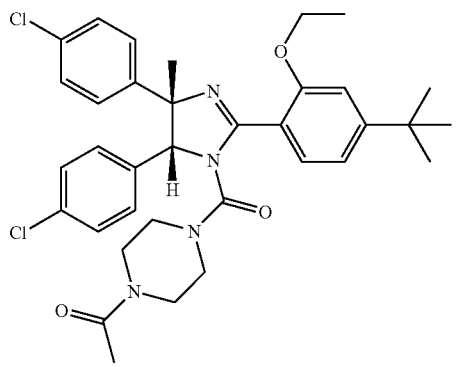

In a manner analogous to the method described in example 5, (4S,5R)-2-(4-tert-butyl-2-ethoxy-phenyl)-4,5-bis-(4-chloro-phenyl)-4-methyl-4,5-dihydro-imidazole-1-carbonyl chloride was reacted with 1-acetyl-piperazine (Aldrich) to give the title compound. LC-MS: 635.2 [(M+H)$^+$]

EXAMPLE 178 rac-(4S*,5R*)-2-(4-tert-Butyl-2-ethoxy-phenyl)-4,5-bis-(4-chloro-phenyl)-4-methyl-4,5-dihydro-imidazole-1-carboxylic acid (2-dimethylamino-ethyl)-amide

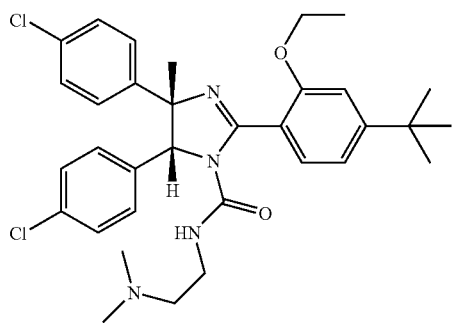

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with N,N-dimethyl-1,2-ethanediamine (Aldrich) to give the title compound. LC-MS: 595.2 [(M+H)$^+$]

EXAMPLE 179 rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-2-one

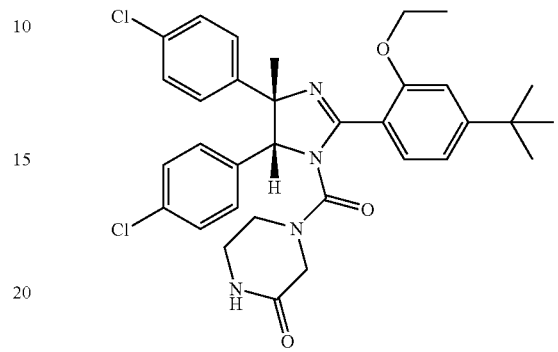

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with 2-piperazinone (Avocado Organics) to give the title compound. LC-MS: 607.2 [(M+H)$^+$]

EXAMPLE 180 rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-morpholin-4-yl-ethanone

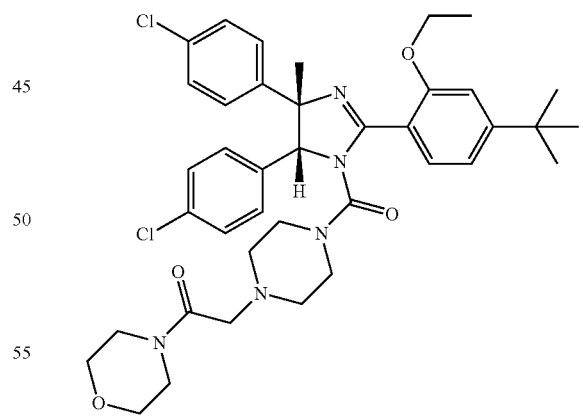

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with 1-morpholin-4-yl-2-piperazin-1-yl-ethanone (Oakwood Products) to give the title compound. LC-MS: 720.3 [(M+H)$^+$]

EXAMPLE 181 rac-[(4S*,5R*)-2-(4-tert-Butyl-2-ethoxy-phenyl)-4,5-bis-(4-chloro-phenyl)-4-methyl-4,5-dihydro-imidazol-1-yl]-(4-methanesulfonyl-piperazin-1-yl)-methanone

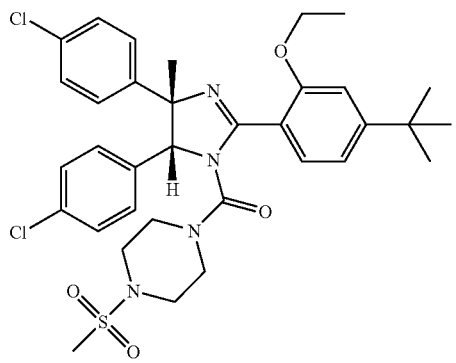

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with 1-methylsulfonyl-piperazine (Aldrich) to give the title compound. LC-MS: 671.2 [(M+H)$^+$]

EXAMPLE 182 rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-pyrrolidin-1-yl-ethanone

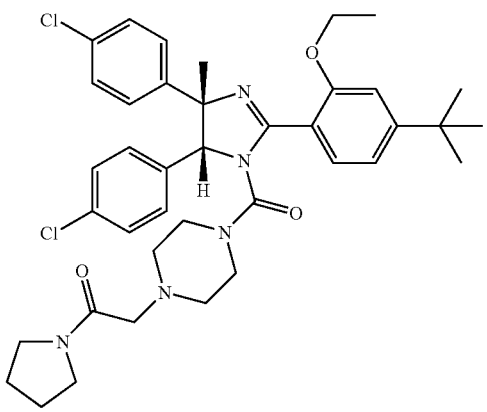

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with 2-piperazin-1-yl-1-pyrrolidin-1-yl-ethanone (Aldrich) to give the title compound. LC-MS: 704.3 [(M+H)$^+$]

EXAMPLE 183 rac-[(4S*,5R*)-2-(4-tert-Butyl-2-ethoxy-phenyl)-4,5-bis-(4-chloro-phenyl)-4-methyl-4,5-dihydro-imidazol-1-yl]-[4-(tetrahydro-furan-2-carbonyl)-piperazin-1-yl]-methanone

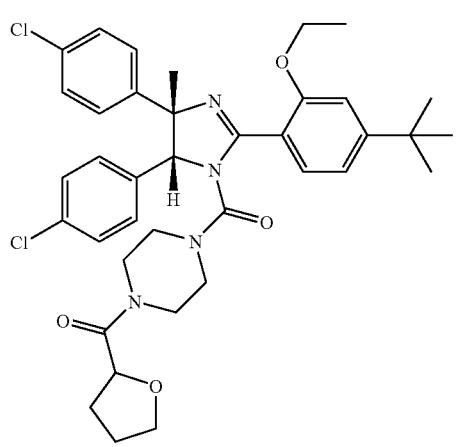

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with piperazin-1-yl-(tetrahydro-furan-2-yl)-methanone (Aldrich) to give the title compound. LC-MS: 691.3 [(M+H)$^+$]

EXAMPLE 184 rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazine-1-carboxylic acid dimethylamide

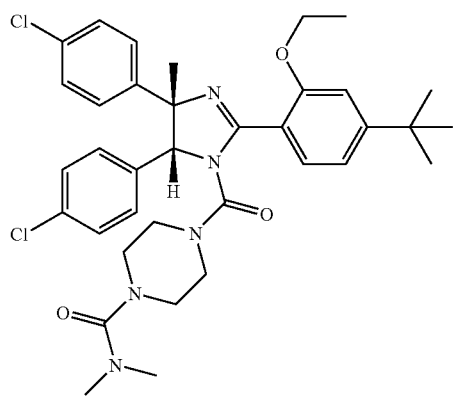

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with piperazine-1-carboxylic acid dimethylamide (Aldrich) to give the title compound. LC-MS: 664.3 [(M+H)+]

EXAMPLE 185 rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-acetamide

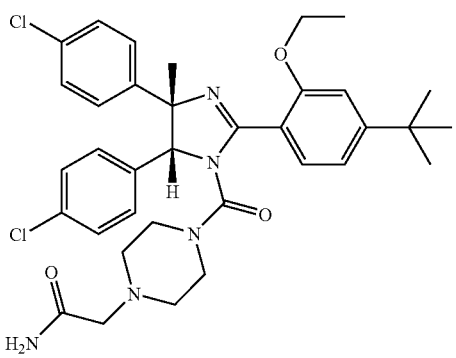

In a manner analogous to the method described in example 5, rac-(4S*,5R*)-2-(4-tert-butyl-2-ethoxy-phenyl)-4,5-bis-(4-chloro-phenyl)-4-methyl-4,5-dihydro-imidazole-1-carbonyl chloride was reacted with 2-piperazin-1-yl-acetamide dihydrochloride (Matrix Scientific) to give the title compound. LC-MS: 650.3 [(M+H)+]

EXAMPLE 186 rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-pyrrolidin-1-yl-ethanone

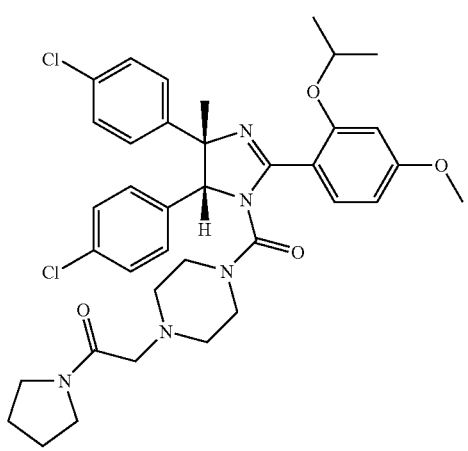

rac-2-{4-[(4S*,5R*)-4,5-Bis-(4-chloro-phenyl)-2-(2-isopropoxy-4-methoxy-phenyl)-4-methyl-4,5-dihydro-1H-imidazole was prepared from rac-(1R*,2S*)-1,2-bis-(4-chloro-phenyl)-propane-1,2-diamine and methyl 2-isopropoxy-4-methoxy-benzoate in the presence of trimethylaluminum using the procedure as described in example 2. It was then reacted with phosgene in the presence of triethylamine to give rac-(4S*,5R*)-4,5-bis-(4-chloro-phenyl)-2-(2-isopropoxy-4-methoxy-phenyl)-4-methyl-4,5-dihydro-imidazole-1-carbonyl chloride (example 3).

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 2-piperazin-1-yl-1-pyrrolidin-1-yl-ethanone (Aldrich) to give the title compound. LC-MS: 692.3 [(M+H)+]

EXAMPLE 187 rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-2-one

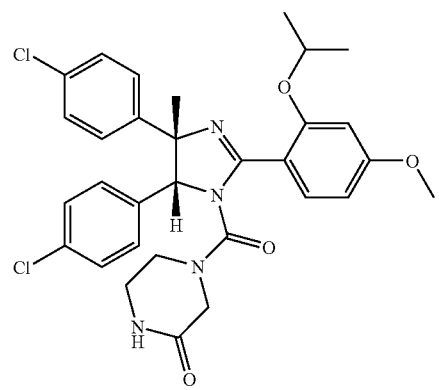

rac-(4S*,5R*)-4,5-Bis-(4-chloro-phenyl)-2-(2-isopropoxy-4-methoxy-phenyl)-4-methyl-4,5-dihydro-1H-imidazole was prepared from rac-(1R*,2S*)-1,2-bis-(4-chloro-phenyl)-propane-1,2-diamine and methyl 2-isopropoxy-4-methoxy-benzoate in the presence of trimethylaluminum using the procedure as described in example 2. It was then reacted with phosgene in the presence of triethylamine to give rac-(4S*,5R*)-4,5-bis-(4-chloro-phenyl)-2-(2-isopropoxy-4-methoxy-phenyl)-4-methyl-4,5-dihydro-imidazole-1-carbonyl chloride (example 3).

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 2-piperazinone (Avocado Organics) to give the title compound. LC-MS: 595.2 [(M+H)+]

EXAMPLE 188 rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-morpholin-4-yl-ethanone

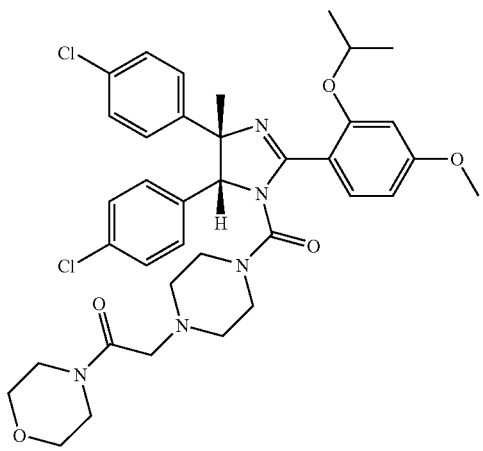

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 1-morpholin-4-yl-2-piperazin-1-yl-ethanone (Oakwood Products) to give the title compound. LC-MS: 708.3 [(M+H)$^+$]

EXAMPLE 189 rac-[(4S*,5R*)-4,5-Bis-(4-chloro-phenyl)-2-(2-isopropoxy-4-methoxy-phenyl)-4-methyl-4,5-dihydro-imidazol-1-yl]-(4-methanesulfonyl-piperazin-1-yl)-methanone

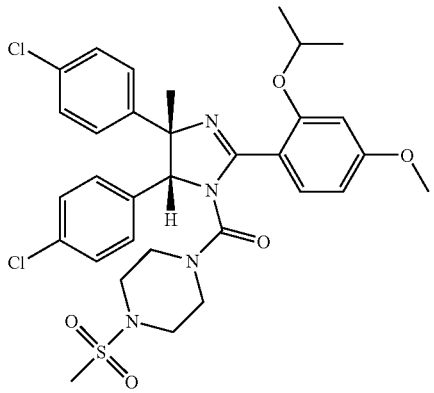

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 1-methylsulfonyl-piperazine (Aldrich) to give the title compound. LC-MS: 659.2 [(M+H)$^+$]

EXAMPLE 190 rac-1-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-ethanone

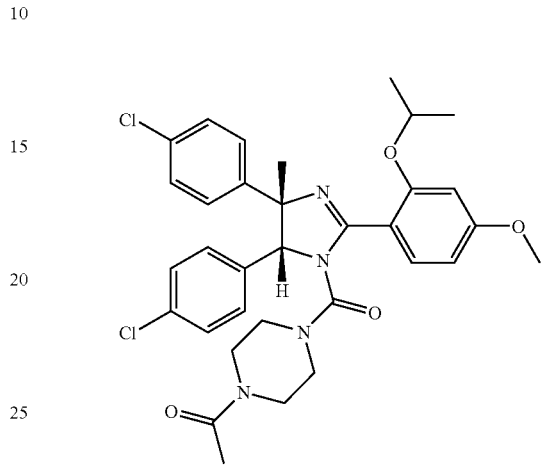

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 1-acetyl-piperazine (Aldrich) to give the title compound. LC-MS: 623.2 [(M+H)$^+$]

EXAMPLE 191 rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(tetrahydro-furan-2-carbonyl)-piperazin-1-yl]-methanone

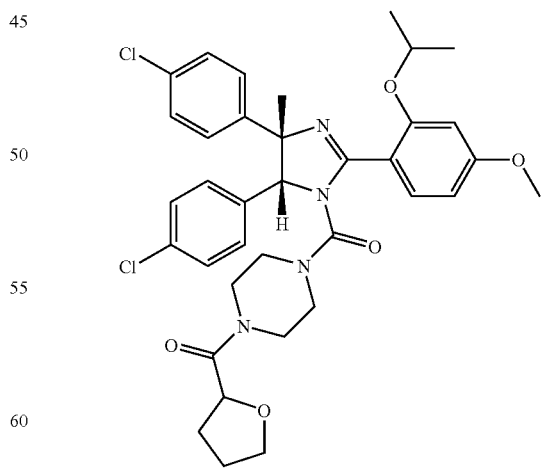

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with piperazin-1-yl-(tetrahydro-furan-2-yl)-methanone (Aldrich) to give the title compound. LC-MS: 679.2 [(M+H)+]

EXAMPLE 192 rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-acetamide

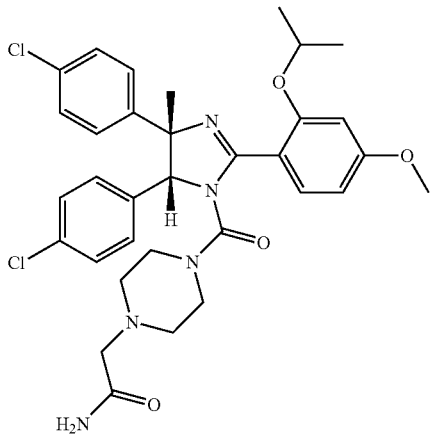

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 2-piperazin-1-yl-acetamide dihydrochloride (Matrix Scientific) to give the title compound. LC-MS: 638.2 [(M+H)+]

EXAMPLE 193 rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazine-1-carboxylic acid dimethylamide

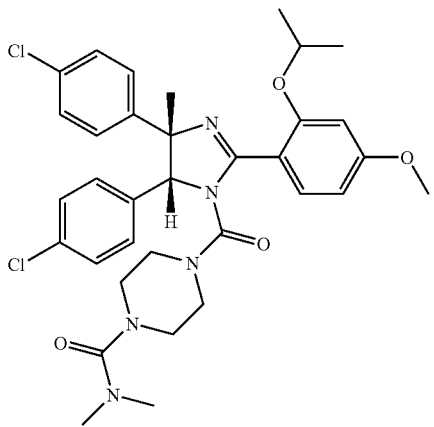

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with piperazine-1-carboxylic acid dimethylamide (Aldrich) to give the title compound. LC-MS: 652.2 [(M+H)+]

EXAMPLE 194 rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(3-methanesulfonyl-propyl)-piperazin-1-yl]-methanone

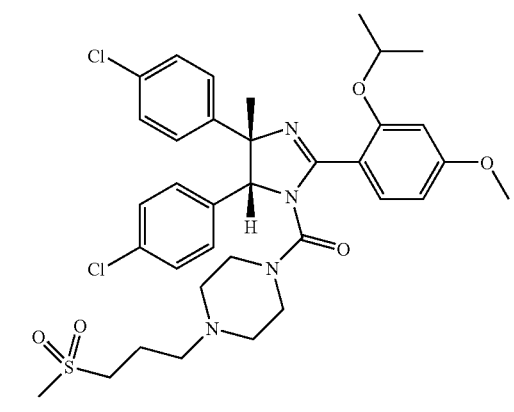

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound. LC-MS: 701.2 [(M+H)+]

EXAMPLE 195 rac-[(4S*,5R*)-4,5-Bis-(4-chloro-phenyl)-2-(2-isopropoxy-4-methoxy-phenyl)-4-methyl-4,5-dihydro-imidazol-1-yl]-piperazin-1-yl-methanone

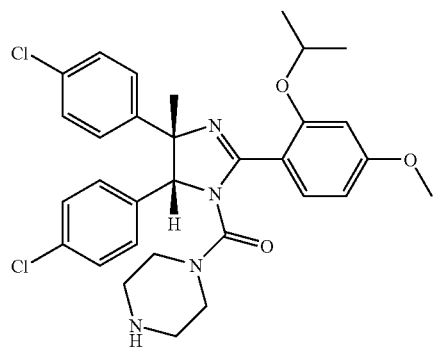

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole- 1-carbonyl chloride was reacted with piperazine (Aldrich) to give the title compound. LC-MS: 581.2 [(M+H)⁺]

EXAMPLE 196 rac-(4S*,5R*)-4,5-Bis-(4-chloro-phenyl)-2-(2-isopropoxy-4-methoxy-phenyl)-4-methyl-4,5-dihydro-imidazole-1-carboxylic acid (2-dimethylamino-ethyl)-amide

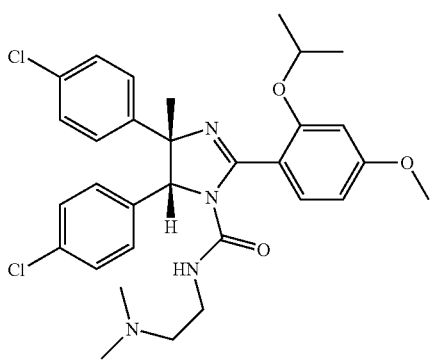

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with N,N-dimethyl-1,2-ethanediamine (Aldrich) to give the title compound. LC-MS: 583.2 [(M+H)⁺]

EXAMPLE 197 rac-1-[(4S*,5R*)-4,5-Bis-(4-chloro-phenyl)-2-(2-isopropoxy-4-methoxy-phenyl)-4-methyl-4,5-dihydro-imidazole-1-carbonyl]-piperidine-4-carboxylic acid amide

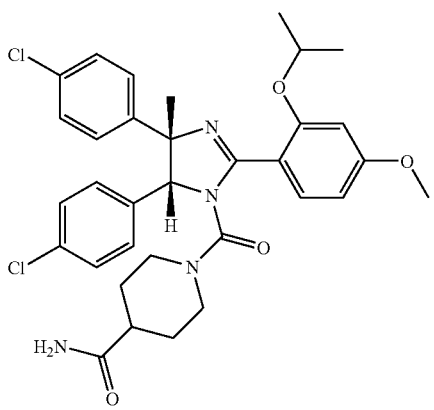

In a manner analogous to the method described in example 5, rac-(4S*,5R*)-4,5-bis-(4-chloro-phenyl)-2-(2-isopropoxy-4-methoxy-phenyl)-4-methyl-4,5-dihydro-imidazole-1-carbonyl chloride was reacted with 1-piperidin-4-yl-ethanone (Aldrich) to give the title compound. LC-MS: 623.3 [(M+H)⁺]

EXAMPLE 198 rac-4-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperazin-2-one

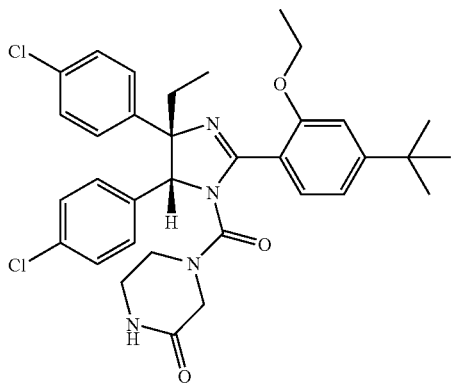

rac-(4S*,5R*)-2-(4-tert-butyl-2-ethoxy-phenyl)-4,5-bis-(4-chloro-phenyl)-4-ethyl-4,5-dihydro-1H-imidazole was prepared from rac-(1R*,2S*)-1,2-bis-(4-chloro-phenyl)-butane-1,2-diamine (prepared from 3,4-bis-aryl-1,2,5-thiadiazole-1,1-dioxide and ethylmagnesium bromide as described in example 170) and methyl 2-isopropoxy-4-methoxy-benzoate in the presence of trimethylaluminum using the procedure as described in example 2. It was then reacted with phosgene in the presence of triethylamine to give rac-(4S*,5R*)-2-(4-tert-butyl-2-ethoxy-phenyl)-4,5-bis-(4-chloro-phenyl)-4-ethyl-4,5-dihydro-imidazole-1-carbonyl chloride.

In a manner analogous to the method described in example 5, rac-(4S*,5R*)-2-(4-tert-butyl-2-ethoxy-phenyl)-4,5-bis-(4-chloro-phenyl)-4-ethyl-4,5-dihydro-imidazole-1-carbonyl chloride was reacted with 2-piperazinone (Avocado Organics) to give the title compound. LC-MS: 621.2 [(M+H)⁺]

EXAMPLE 199 rac-1-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperidine-4-carboxylic acid amide

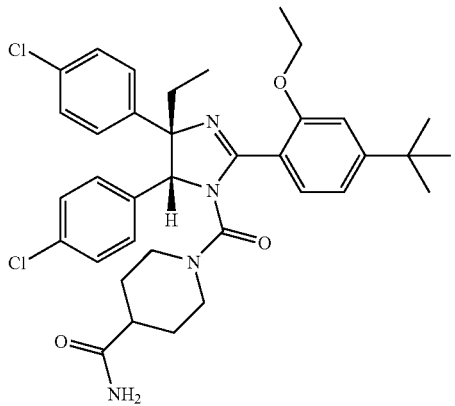

In a manner analogous to the method described in example 5, rac-(4S*,5R*)-2-(4-tert-butyl-2-ethoxy-phenyl)-4,5-bis-(4-chloro-phenyl)-4-ethyl-4,5-dihydro-imidazole-1-carbonyl chloride was reacted with 1-piperidin-4-yl-ethanone (Aldrich) to give the title compound. LC-MS: 649.3 [(M+H)+]

EXAMPLE 200 rac-[(4S*,5R*)-4,5-Bis-(4-chloro-phenyl)-4-ethyl-2-(2-isopropoxy-4-methoxy-phenyl)-4,5-dihydro-imidazol-1-yl]-[4-(tetrahydro-furan-2-carbonyl)-piperazin-1-yl]-methanone

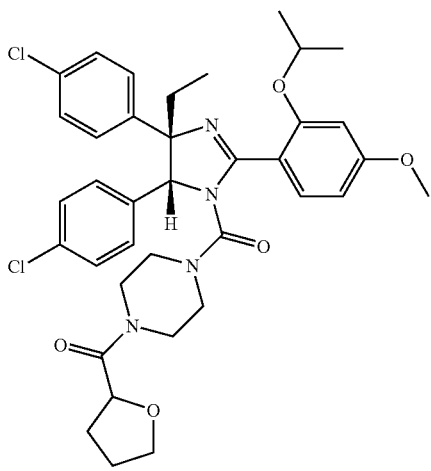

In a manner analogous to the method described in example 5, rac-(4S*,5R*)-4,5-bis-(4-chloro-phenyl)-4-ethyl-2-(2-isopropoxy-4-methoxy-phenyl)-4,5-dihydro-imidazole-1-carbonyl chloride was reacted with piperazin-1-yl-(tetrahydro-furan-2-yl)-methanone (Aldrich) to give the title compound. LC-MS: 693.3 [(M+H)+]

EXAMPLE 201 rac-2-{4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazin-1-yl}-1-morpholin-4-yl-ethanone

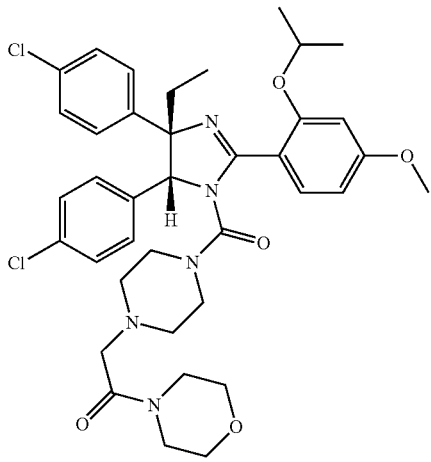

In a manner analogous to the method described in example 5, rac-(4S*,5R*)-4,5-bis-(4-chloro-phenyl)-4-ethyl-2-(2-isopropoxy-4-methoxy-phenyl)-4,5-dihydro-imidazole-1-carbonyl chloride was reacted with 1-morpholin-4-yl-2-piperazin-1-yl-ethanone (Oakwood Products) to give the title compound. LC-MS: 722.3 [(M+H)+]

EXAMPLE 202 rac-4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazine-1-carboxylic acid dimethylamide

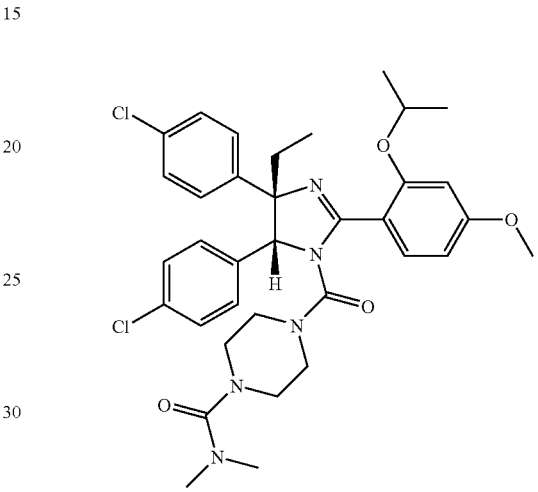

In a manner analogous to the method described in example 5, rac-(4S*,5R*)-4,5-bis-(4-chloro-phenyl)-4-ethyl-2-(2-isopropoxy-4-methoxy-phenyl)-4,5-dihydro-imidazole-1-carbonyl chloride was reacted with piperazine-1-carboxylic acid dimethylamide (Aldrich) to give the title compound. LC-MS: 666.3 [(M+H)+]

EXAMPLE 203

[(4S,5R)-2-(4-tert-Butyl-2-ethoxy-phenyl)-4,5-bis-(4-fluoro-phenyl)-4,5-dimethyl-4,5-dihydro-imidazol-1-yl]-[4-(3-methanesulfonyl-propyl)-piperazin-1-yl]-methanone

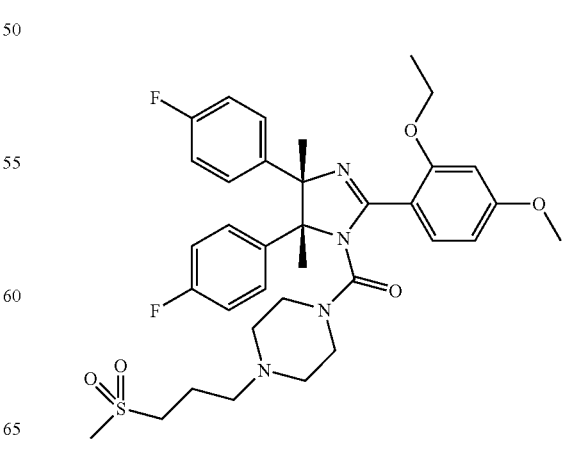

meso-2,3-bis-(4-fluorophenyl)-2,3-butanediamine was prepared from 4,4'-difluorobenzyl in an analogous manner as described in examples 169 and 170. It was then reacted with 2-ethoxy-benzoyl chloride using the procedure as described in example 2 (method 1) to give rac-(4S*,5R*)-2-(4-tert-butyl-2-ethoxy-phenyl)-4,5-bis-(4-fluoro-phenyl)-4,5-dimethyl-4,5-dihydro-1H-imidazole.

rac-(4S*,5R*)-2-(4-tert-Butyl-2-ethoxy-phenyl)-4,5-bis-(4-fluoro-phenyl)-4,5-dimethyl-4,5-dihydro-1H-imidazole was then reacted with phosgene in the presence of triethylamine to give rac-(4S*,5R*)-2-(4-tert-butyl-2-ethoxy-phenyl)-4,5-bis-(4-fluoro-phenyl)-4,5-dimethyl-4,5-dihydro-imidazole-1-carbonyl chloride.

In a manner analogous to the method described in example 5, rac-(4S*,5R*)-2-(4-tert-butyl-2-ethoxy-phenyl)-4,5-bis-(4-fluoro-phenyl)-4,5-dimethyl-4,5-dihydro-imidazole-1-carbonyl chloride was reacted with 1-(3-methanesulfonyl-propyl)-piperazine dihydrochloride (prepared as described in Fotouhi, N. et al. WO 2005110996) to give the title compound as a racemic mixture. The enantiomers were separated by supercritical fluid chromatography (Berger Instrument Multi-Gram II, Daicel ChiralPak OD-H 3×25 cm, 35° C. at 100 bar, eluting with 30% methanol in carbon dioxide) gave the title compound. HR-MS (ES, m/z) calculated for $C_{38}H_{49}N_4O_4SF_2$ $[(M+H)^+]$ 695.3437, observed 695.3433.

EXAMPLE 204

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing: 90 nM biotinylate peptide, 160 ng/mL GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/mL working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

$IC_{50}$s showing biological activity that applies to compounds of the subject matter of this invention ranges from about 1 nM to about 1000 nM. Specific data for some examples are as follows:

| Example | $IC_{50}$ (µM) |
|---|---|
| 5 | 0.019 |
| 6 | 0.344 |
| 8 | 0.046 |
| 35 | 0.017 |
| 177 | 0.107 |
| 190 | 0.048 |

What is claimed:
1. A compound of the formula

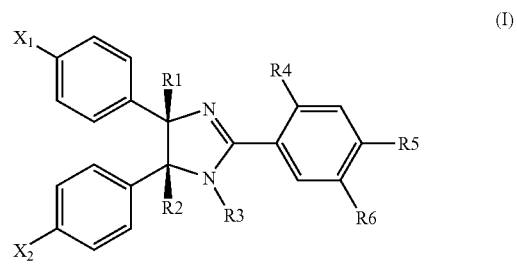

(I)

wherein $X_1$ and $X_2$ are halogen, acetylene, cyano, trifluoromethyl or nitro;
$R^1$ and $R^2$ are selected from the group consisting of H, $CH_3$, $CH_2CH_3$, $CH_2OH$ and $CH_2OCH_3$ with the proviso that $R^1$ and $R^2$ are not both hydrogen;
$R^3$ is H or —C(=O)—$R^7$;
and where $R^6$ is hydrogen then
  $R^4$ is —$OCH_3$, —$OCH_2CH_3$, —$OCH_2CH_2F$, —$OCH_2CH_2OCH_3$, or —$OCH(CH_3)_2$;
  $R^5$ is
  —H
  -halogen,
  —$CH_3$,
  —$CF_3$,
  —$OCH_3$,
  —$C(CH_3)_2$,
  -cyclopropyl,
  -cyano,
  —$C(CH_3)_3$,
  —$C(CH_3)_2$OR (where R is H, $CH_3$ or $CH_2CH_3$),
  —$C(CH_3)_2$CH—OR (where R is H, $CH_3$, $CH(CH_3)_2$, $CH_2CH_2OH$ or $CH_2CH_2OCH_3$),
  —$C(CH_3)_2$CN,
  —$C(CH_3)_2$COR (where R is $CH_3$),
  —$C(CH_3)_2$COOR (where R is H, $CH_3$, $CH_2CH_3$ or $CH(CH_3)_2$),
  —$C(CH_3)_2$CONR$^a$R$^b$ (where R$^a$ is H or $CH_3$ and R$^b$=H or $CH_3$),
  —SR (where R is $CH_3$ or $CH_2CH_3$), or
  —$SO_2$R (where R is $CH_3$, $CH_2CH_3$, 1-pyrrolidine, NH-tert-butyl or N($CH_3$)$_2$);
and where $R^6$ is not hydrogen then
  $R^4$ is —$OCH_3$, —$OCH_2CH_3$, —$OCH_2CH_2F$, —$OCH_2CH_2OCH_3$, or —$OCH(CH_3)_2$;
  $R^5$ is hydrogen, —Cl, —$OCH_3$, tert-butyl or —N($CH_3$)$_2$;
  $R^6$ is —Cl, cyclopropyl, —$SO_2$R (where R is $CH_3$, $CH_2CH_3$, 1-pyrrolidine, NH-tert-butyl, $NH_2$, or N($CH_3$)$_2$);
and $R^7$ is selected from the group consisting of i) —CH$_3$, —CH(CH$_3$)$_2$, —CH$_2$CH(CH$_3$)$_2$, cyclopropyl, cyclobutyl, —CH$_2$CH$_2$Ph, 2-furanyl, phenyl, or phenyl substituted by chloro, OCH$_3$ or cyano,
ii) 4-morpholinyl, 1-piperidinyl, 4-thiomorpholinyl, or 4-thiomorpholinyl-1,1-dioxide,
iii) —NR$^c_2$ (wherein R$^c$ is hydrogen, —CH$_3$, —CH$_2$CH$_3$, —CH$_2$CH$_2$OH, —CH$_2$CH$_2$OCH$_3$, or —CH$_2$CH(OH)CH$_2$OH),
iv) a substituted piperazine of the formula

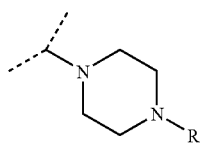

wherein R is selected from the group consisting of
a) hydrogen,
b) lower alkyl,
c) CH(CH$_3$)$_2$,
d) CH(CH$_2$CH$_3$)$_2$,
e) cyclopentyl,
f) —CH$_2$CH(OH)CH$_3$,
g) —CH$_2$CF$_3$,
h) —CH$_2$CH(OH)CF$_3$,
i) —CH$_2$C(CH$_3$)$_2$OH,
j) —CH$_2$-[4-N-methylpiperidinyl],
k) —CH$_2$CH$_2$R$^d$ (wherein R$^d$ is —OH, —OCH$_3$, —OCH$_2$CH$_2$OH, —OCH$_2$CH$_2$OCH$_3$, —CN, —CF$_3$, —SO$_2$CH$_3$, —SO$_2$NH$_2$, —SO$_2$N(CH$_3$)$_2$, —CONH$_2$, —CON(CH$_3$)$_2$, —NH$_2$, —NHCOCH$_3$, —NHSO$_2$CH$_3$, —N(CH$_3$)$_2$, —N(CH$_2$CH$_3$)$_2$, —N(CH$_2$CH$_2$CH$_3$)$_2$, 1-pyrrolidinyl, 1-piperidinyl, 4-morpholinyl, 2-isothiazolidinyl-1,1-dioxide, or 2-tetrahydrofuranyl),
l) —CH$_2$CH$_2$CH$_2$R$^e$ (wherein R$^e$ is —OH, —OCH$_3$, —SO$_2$CH$_3$, —SO$_2$CH$_2$CH$_3$, —SO$_2$N(CH$_3$)$_2$, —CN, —N(CH$_3$)$_2$, —N(CH$_2$CH$_3$)$_2$, 1-imidazoyl, 1-pyrrolidinyl, 1-piperidinyl, 4-morpholinyl, —COOCH$_3$, —COOCH$_2$CH$_3$, —COOC(CH$_3$)$_3$, —CON(CH$_3$)$_2$, —CO—R$^f$ (wherein R$^f$ is CH$_3$, CH$_2$CH$_3$, cyclopropyl, phenyl, 2-thienyl, 3-thienyl, 2-furanyl, 3-furanyl), —COCH$_2$—R$^g$ (wherein R$^g$ is H, —NHCH$_2$CH$_2$OH, —NHCH$_2$CH$_2$OCH$_3$, —NHCH$_2$CH$_2$N(CH$_3$)$_2$, 1-piperidinyl, 1-(piperidinyl-4-methanol), 4-morpholinyl, or —N(CH$_3$)-(3-(1-methylpyrrolidinyl))),
m) —CH$_2$—CO—R$^h$ (wherein R$^h$ is —OCH$_3$, OCH$_2$CH$_3$, —NH$_2$, —NHCH$_2$CH(CH$_3$)$_2$, —NHCH$_2$CF$_3$, —NH-cyclopropyl, —NH-tert-butyl, —NHCH$_2$CH$_2$OH, —N(CH$_3$)$_2$, —N(CH$_2$CH$_3$)$_2$, —N(CH$_2$CH$_2$OH)$_2$, —N(CH$_2$CH$_2$OCH$_3$)$_2$, —N(CH$_3$)CH$_2$CH$_2$OH, —N(CH$_3$)CH$_2$CH$_2$OCH$_3$, —NHCH$_2$CH$_2$OCH$_3$, 1-pyrrolidinyl, 1-piperidinyl, 1-(piperidinyl-4-methanol), 1-(piperidinyl-3-carboxamide), 4-morpholinyl, 4-thiomorpholinyl, 4-thiomorpholinyl-1,1-dioxide, 1-piperazinyl, 1-(4-acetylpiperazinyl), 1-(3-oxopiperazinyl),
n) —SO$_2$R$^i$ (wherein R$^i$ is —CH$_3$, —CH$_2$CH$_3$, —CH(CH$_3$)$_2$, phenyl, 4-methylphenyl, 4-propylphenyl, CF$_3$, 2-thienyl, 3-thienyl, NH$_2$, NHCH$_3$, N(CH$_3$)$_2$, NHCH$_2$CH$_2$OCH$_3$, N(CH$_2$CH$_2$OCH$_3$)$_2$, 1-pyrrolidinyl, 1-piperidinyl, 4-morpholinyl, 1-piperazyl-4-ethanol, 1-(4-acetylpiperazinyl), 1-(3-oxopiperazinyl)),
o) —COR$^j$ (wherein R$^j$ is —CH$_3$, —CH$_2$CH$_3$, —CH(CH$_3$)$_2$, 2-tetrahydrofuranyl, 2-thienyl, 3-thienyl, NH$_2$, NHCH$_3$, N(CH$_3$)$_2$, 1-pyrrolidinyl, 1-piperidinyl, 4-morpholinyl, 1-piperazinyl-4-ethanol, 1-(4-acetylpiperazinyl), or 1-(3-oxopiperazinyl)),
p) 4-tetrahydro-2H-thiopyranyl-1,1-dioxide,
q) 4-piperidinyl-1-acetyl,
r) 4-piperidinyl-1-dimethylcarboxamide, and
s) 3-tetrahydro-thiophenyl-1,1-dioxide;
v) a substituted oxopiperazine of the formula

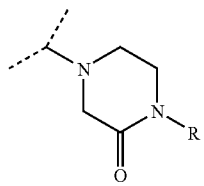

wherein R is H, —CH$_3$, —CH$_2$CH$_3$, —CH$_2$CH$_2$CH$_3$, —CH$_2$CH$_2$OH, or —CH$_2$CH$_2$OCH$_3$
and
vi) a substituted piperidine of the formula

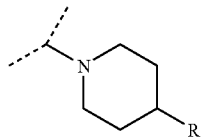

wherein R is H, COOCH$_3$, COOCH$_2$CH$_3$, CONH$_2$, —OH, CH$_2$OH, CH$_2$CH$_2$OH, CH$_2$—N(CH$_2$CH$_3$)$_2$, —CH$_2$-(1-piperazinyl), CH$_2$-(1-(3-oxopiperazinyl)), NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$-(1-piperidinecarboxamide), NHCOCH$_2$—(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$, 1-pyrrolidinyl, 1-piperidinyl, 1-(4-methylpiperazinyl), or 4-morpholinyl;
and the pharmaceutically acceptable salts and esters thereof.

2. Compound of claim 1 wherein X$_1$ and X$_2$ are —Cl.

3. Compound of claim 2 wherein R$^3$ is —C(=O)—R$^7$.

4. Compound of claim 3 where R$^6$ is hydrogen; R$^4$ is —OCH$_3$, —OCH$_2$CH$_3$, or —OCH(CH$_3$)$_2$; and R$^5$ is —C(CH$_3$)$_3$, —C(CH$_3$)$_2$OR (where R is H or CH$_3$), —C(CH$_3$)$_2$CH—OR (where R is H or CH$_3$), —C(CH$_3$)$_2$CN, —C(CH$_3$)$_2$COR (where R is CH$_3$), —SO$_2$R (where R is CH$_3$, 1-pyrrolidine, NH-tert-butyl or N(CH$_3$)$_2$).

5. The compound of claim 3 where R$^4$ is —OCH$_3$, —OCH$_2$CH$_3$, or —OCH(CH$_3$)$_2$; R$^5$ is —Cl; and R$^6$ is —SO$_2$R (where R is CH$_3$, 1-pyrrolidine, NH-tert-butyl, NH$_2$, or N(CH$_3$)$_2$).

6. The compound of claim 3 wherein R$^7$ is

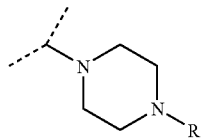

and wherein R is —CHCOR$^h$.

7. The compound of claim 6 wherein $R^h$ is 4-morpholinyl, 1-pyrrolidinyl, 1-piperidinyl, $NH_2$, or $N(CH_3)_2$.

8. The compound of claim 3 wherein $R^7$ is

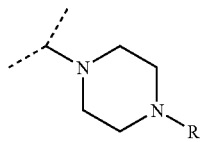

and wherein R is —$CH_2CH_2CH_2R^e$.

9. The compound of claim 8 wherein $R^e$ is —$SO_2CH_3$ or —$SO_2CH_2CH_3$.

10. The compound of claim 3 wherein $R^7$ is

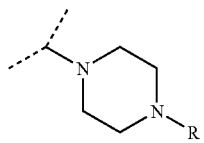

and wherein R is —$CH_2CH_2R^d$.

11. The compound of claim 10 wherein $R^d$ is —$SO_2CH_3$, —$NHSO_2CH_3$, —$NHCOCH_3$, or $CF_3$.

12. The compound of claim 3 wherein $R^7$ is

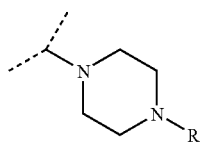

and R is 4-tetrahydro-2H-thiopyranyl-1,1-dioxide.

13. A compound of claim 1 selected from the group consisting of:
- rac-(4S*,5R*)-4,5-Bis(4-chlorophenyl)-2-(4-(tert-butyl)-2-ethoxy-phenyl)-4,5-dimethyl-4,5-dihydro-1H-imidazole,
- (4S,5R)-4-[[4-[[4,5-Bis(4-chlorophenyl)-2-[4-(tert-butyl)-2-ethoxy-phenyl]-4,5-dimethyl-4,5-dihydro-1H-imidazol-1-yl]carbonyl]-1-piperazinyl]acetyl]-morpholine,
- (4S,5R)-4-[[4-[[4,5-bis(4-chlorophenyl)-2-[4-(tert-butyl)-2-ethoxy-phenyl]-4,5-dimethyl-4,5-dihydro-1H-imidazol-1-yl]carbonyl]-1-piperidine,
- ((4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3,3,3-trifluoropropyl]-piperazine,
- 2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-acetamide,
- 2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-1-pyrrolidin-1-yl-ethanone and
- N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-acetamide.

14. A compound of claim 1 selected from the group consisting of
- N-(2-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethyl)-methanesulfonamide,
- [(4S,5R)-2-(4-tert-Butyl-2-ethoxy-phenyl)-4,5-bis-(4-chloro-phenyl)-4,5-dimethyl-4,5-dihydro-imidazol-1-yl]-[4-(2-hydroxy-ethyl)-piperazin-1-yl]-methanone,
- (S)-4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-1-methyl-piperazine-2-carboxylic acid methyl ester,
- 5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-2-tert-butyl-4-ethoxy-N,N-dimethyl-benzenesulfonamide,
- rac-2-{4-[(4S*,5R*)-4,5-Bis-(4-chloro-phenyl)-4,5-dimethyl-4,5-dihydro-1H-imidazol-2-yl]-3-ethoxy-phenyl}-2-methyl-propionitrile,
- 2-(4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-2-methyl-propionitrile,
- N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-methanesulfonamide,
- N-[2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-ethyl]-acetamide and
- 2-(4-{(4S,5R)-4,5-Bis-(4-chloro-phenyl)-1-[4-(2-hydroxy-ethyl)-piperazine-1-carbonyl]-4,5-dimethyl-4,5-dihydro-1H-imidazol-2-yl}-3-ethoxy-phenyl)-2-methyl-propionitrile.

15. A compound of claim 1 selected from the group consisting of
- 2-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-2-methyl-propionitrile,
- 2-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-acetamide,
- 2-[4-((4S,5R)-4,5-Bis-(4-chloro-phenyl)-1-{4-[2-(1,1-dioxo-isothiazolidine-2-yl)-ethyl]-piperazine-1-carbonyl}-4,5-dimethyl-4,5-dihydro-1H-imidazol-2-yl)-3-ethoxy-phenyl]-2-methyl-propionitrile,
- 2-(4-{(4S,5R)-4,5-Bis-(4-chloro-phenyl)-4,5-dimethyl-1-[4-(2-oxo-2-pyrrolidin-1-yl-ethyl)-piperazine-1-carbonyl]-4,5-dihydro-1H-imidazol-2-yl}-3-ethoxy-phenyl)-2-methyl-propionitrile,
- 2-{4-[(4S,5R)-1-[4-(1-Acetyl-piperidin-4-yl)-piperazine-1-carbonyl]-4,5-bis-(4-chloro-phenyl)-4,5-dimethyl-4,5-dihydro-1H-imidazol-2-yl]-3-ethoxy-phenyl}-2-methyl-propionitrile,
- 4-(4-{(4S,5R)-4,5-Bis-(4-chloro-phenyl)-2-[4-(cyano-dimethyl-methyl)-2-ethoxy-phenyl]-4,5-dimethyl-4,5-dihydro-imidazole-1-carbonyl}-piperazin-1-yl)-piperidine-1-carboxylic acid isopropylamide,
- rac-(4S*,5R*)-4,5-Bis-(4-chloro-phenyl)-2-[2-ethoxy-4-(pyrrolidine-1-sulfonyl)-phenyl]-4,5-dimethyl-4,5-dihydro-1H-imidazole and rac-(4S*,5R*)-4-[(4,5-Bis-(4-chloro-phenyl)-4,5-dimethyl-4,5-dihydro-1H-imidazol-2-yl]-N-tert-butyl-3-ethoxy-benzenesulfonamide.

16. A compound of claim 1 selected from the group consisting of
{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(3-methanesulfonyl-propyl)-piperazin-1-yl]-methanone,
2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-acetamide,
2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-1-pyrrolidin-1-yl-ethanone,
N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-methanesulfonamide,
N-[2-(4-{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazole-1-carbonyl}-piperazin-1-yl)-ethyl]-acetamide,
{(4S,5R)-4,5-Bis-(4-chloro-phenyl)-2-[2-ethoxy-4-(pyrrolidine-1-sulfonyl)-phenyl]-4,5-dimethyl-4,5-dihydro-imidazol-1-yl}-[4-(2-hydroxy-ethyl)-piperazin-1-yl]-methanone,
4-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-3-ethoxy-benzenesulfonamide,
2-{4-[(4S,5R)-2-(4-tert-Butylsulfamoyl-2-ethoxy-phenyl)-4,5-bis-(4-chloro-phenyl)-4,5-dimethyl-4,5-dihydro-imidazole-1-carbonyl]-piperazin-1-yl}-acetamide,
rac-(4S*,5R*)-5-[4,5-Bis-(4-chlorophenyl)-4,5-dimethyl-4,5-dihydro-1H-imidazol-2-yl]-N-tert-butyl-2-chloro-4-ethoxybenzenesulfonamide and
5-{(4S,5R)-4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-N-tert-butyl-2-chloro-4-ethoxy-benzenesulfonamide.

17. A compound of claim 1 selected from the group consisting of
5-{(4S,5R)-4,5-Bis-(4-chlorophenyl)-1-[4-(2-methanesulfonylaminoethyl)piperazine-1-carbonyl]-4,5-dimethyl-4,5-dihydro-1H-imidazol-2-yl}-N-tert-butyl-2-chloro-4-ethoxybenzenesulfonamide,
N-{(4S,5R)-(2-{4-[2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}ethyl)acetamide,
5-{(4S,5R)-4,5-Bis-(4-chlorophenyl)-1-[4-(2-hydroxyethyl)piperazine-1-carbonyl]-4,5-dimethyl-4,5-dihydro-1H-imidazol-2-yl}-N-tert-butyl-2-chloro-4-ethoxybenzenesulfonamide,
5-{(4S,5R)-4,5-Bis-(4-chlorophenyl)-4,5-dimethyl-1-[4-(2-oxo-2-pyrrolidin-1-yl-ethyl)-piperazine-1-carbonyl]-4,5-dihydro-1H-imidazol-2-yl}-N-tert-butyl-2-chloro-4-ethoxybenzenesulfonamide,
2-{4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-piperazin-1-yl}-acetamide,
(S)-4-[(4S,5R)-2-(5-tert-Butylsulfamoyl-4-chloro-2-ethoxyphenyl)-4,5-bis-(4-chlorophenyl)-4,5-dimethyl-4,5-dihydroimidazole-1-carbonyl]-1-methylpiperazine-2-carboxylic acid methyl ester,
rac-(4S*,5R*)-2-[4-Chloro-2-ethoxy-5-(pyrrolidine-1-sulfonyl)phenyl]-4,5-bis-(4-chlorophenyl)-4,5-dimethyl-4,5-dihydro-1H-imidazole,
5-{(4S,5R)-2-[4-Chloro-2-ethoxy-5-(pyrrolidine-1-sulfonyl)phenyl]-4,5-bis-(4-chloro-phenyl)-4,5-dimethyl-4,5-dihydroimidazol-1-yl]-[4-(3-methanesulfonylpropyl)-piperazin-1-yl]methanone and
rac-(4S*,5R*)-4,5-Bis-(4-chlorophenyl)-2-[2-ethoxy-4-methoxy-5-(pyrrolidine-1-sulfonyl)phenyl]-4,5-dimethyl-4,5-dihydro-1H-imidazole.

18. A compound of claim 1 selected from the group consisting of
{(4S,5R)-4,5-Bis-(4-chlorophenyl)-2-[2-ethoxy-4-methoxy-5-(pyrrolidine-1-sulfonyl)-phenyl]-4,5-dimethyl-4,5-dihydroimidazol-1-yl}-[4-(3-methanesulfonylpropyl)-piperazin-1-yl]methanone,
rac-(4S*,5R*)-2-(4-Chloro-2-ethoxy-5-methanesulfonylphenyl)-4,5-bis-(4-chlorophenyl)-4,5-dimethyl-4,5-dihydro-1H-imidazole,
[(4S,5R)-2-(4-Chloro-2-ethoxy-5-methanesulfonyl-phenyl)-4,5-bis-(4-chlorophenyl)-4,5-dimethyl-4,5-dihydroimidazol-1-yl]-[4-(3-methanesulfonylpropyl)-piperazin-1-yl]methanone,
rac-(4S*,5R*)-4,5-Bis-(4-chlorophenyl)-2-[2-ethoxy-5-(pyrrolidine-1-sulfonyl)phenyl]-4,5-dimethyl-4,5-dihydro-1H-imidazole,
{(4S,5R)-4,5-Bis-(4-chlorophenyl)-2-[2-ethoxy-5-(pyrrolidine-1-sulfonyl)phenyl]-4,5-dimethyl-4,5-dihydroimidazol-1-yl}-[4-(3-methanesulfonylpropyl)-piperazin-1-yl]methanone,
rac-4-[(4S*,5R*)-4,5-Bis-(4-chloro-phenyl)-4,5-dimethyl-4,5-dihydro-1H-imidazol-2-yl]-3-ethoxy-benzonitrile and
4-{(4S,5R)-4,5-Bis-(4-chlorophenyl)-1-[4-(3-methanesulfonylpropyl)-piperazine-1-carbonyl]-4,5-dimethyl-4,5-dihydro-1H-imidazol-2-yl}-3-ethoxybenzonitrile.

19. A compound of claim 1 selected from the group consisting of
[(4S,5R)-2-(4-tert-Butyl-2-ethoxy-phenyl)-4,5-bis-(4-chloro-phenyl)-4,5-dimethyl-4,5-dihydro-imidazol-1-yl]-piperazin-1-yl-methanone,
1-{4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-piperazin-1-yl}-ethanone,
N-tert-Butyl-2-{4-[(4S,5R)-2-(4-tert-butyl-2-ethoxy-phenyl)-4,5-bis-(4-chloro-phenyl)-4,5-dimethyl-4,5-dihydro-imidazole-1-carbonyl]-piperazin-1-yl}-acetamide,
rac-(4S*,5R*)-2-(4-Bromo-2-ethoxy-phenyl)-4,5-bis-(4-chloro-phenyl)-4,5-dimethyl-4,5-dihydro-1H-imidazole,
rac-(4S*,5R*)-2-(4-Bromo-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,
rac-2-{4-[(4S*,5R*)-4,5-Bis-(4-chloro-phenyl)-4,5-dimethyl-4,5-dihydro-1H-imidazol-2-yl]-3-ethoxy-phenyl}-propan-2-ol and
[(4S,5R)-4,5-Bis-(4-chloro-phenyl)-2-(2-ethoxy-phenyl)-4,5-dimethyl-4,5-dihydro-imidazol-1-yl]-[4-(3-methanesulfonyl-propyl)-piperazin-1-yl]-methanone.

20. A compound of claim 1 selected from the group consisting of
2-{4-[(4S,5R)-4,5-Bis-(4-chloro-phenyl)-2-(2-ethoxy-phenyl)-4,5-dimethyl-4,5-dihydro-imidazole-1-carbonyl]-piperazin-1-yl}-acetamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(3-methanesulfonyl-propyl)-piperazin-1-yl]-methanone, 2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-acetamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(2-hydroxy-ethyl)-piperazin-1-yl]-methanone, 2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-1-pyrrolidin-1-yl-ethanone, N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-acetamide, N-[2-(4-{(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazole-1-carbonyl}-piperazin-1-yl)-ethyl]-methanesulfonamide, {(4S,5R)-4,5-Bis-(4-chloro-phenyl)-2-[2-ethoxy-4-(1-hydroxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone, rac-(4S*,5R*)-4,5-Bis-(4-chloro-phenyl)-2-(2-isopropoxy-4-methoxy-phenyl)-4,5-dimethyl-4,5-dihydro-1H-imidazole.

21. A compound of claim 1 selected from the group consisting of rac-(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(3-methanesulfonyl-propyl)-piperazin-1-yl]-methanone, rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-acetamide, rac-2-{4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-1-yl}-1-morpholin-4-yl-ethanone, rac-4-[(4S*,5R*)-4,5-Bis-(4-chloro-phenyl)-2-(2-isopropoxy-4-methoxy-phenyl)-4,5-dimethyl-4,5-dihydro-imidazole-1-carbonyl]-piperazin-2-one, rac-[(4S*,5R*)-4,5-Bis-(4-chloro-phenyl)-2-(2-isopropoxy-4-methoxy-phenyl)-4,5-dimethyl-4,5-dihydro-imidazol-1-yl]-[4-(2-methanesulfonyl-ethyl)-piperazin-1-yl]-methanone, rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-1H-imidazole, 2-(4-{(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazole-1-carbonyl}-piperazin-1-yl)-acetamide, {rac-(4S*,5R*)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(3-methanesulfonyl-propyl)-piperazin-1-yl]-methanone and {(4S,5R)-4,5-Bis-(4-chloro-phenyl)-2-[2-ethoxy-4-(1-methoxy-1-methyl-ethyl)-phenyl]-4,5-dimethyl-4,5-dihydro-imidazol-1-yl}-[4-(1,1-dioxo-tetrahydro-2H-thiopyran-4-yl)-piperazin-1-yl]-methanone.

22. A compound of claim 1 selected from the group consisting of rac-1-[(4S*,5R*)-2-(4-tert-Butyl-2-ethoxy-phenyl)-4,5-bis-(4-chloro-phenyl)-4,5-dimethyl-4,5-dihydro-imidazol-1-yl]-ethanone, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-2-methyl-propan-1-one,

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclopropyl-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-cyclobutyl-methanone, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-methyl-butan-1-one, 1-[(4S,5R)-2-(4-tert-Butyl-2-ethoxy-phenyl)-4,5-bis-(4-chloro-phenyl)-4,5-dimethyl-4,5-dihydro-imidazol-1-yl]-3-phenyl-propan-1-one, 4-[(4S,5R)-2-(4-tert-Butyl-2-ethoxy-phenyl)-4,5-bis-(4-chloro-phenyl)-4,5-dimethyl-4,5-dihydro-imidazole-1-carbonyl]-benzonitrile,

[(4S,5R)-2-(4-tert-Butyl-2-ethoxy-phenyl)-4,5-bis-(4-chloro-phenyl)-4,5-dimethyl-4,5-dihydro-imidazol-1-yl]-furan-2-yl-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-phenyl-methanone and rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-methoxy-phenyl)-methanone.

23. A compound of claim 1 selected from the group consisting of rac-[(4S*,5R*)-2-(4-tert-Butyl-2-ethoxy-phenyl)-4,5-bis-(4-chloro-phenyl)-4,5-dimethyl-4,5-dihydro-imidazol-1-yl]-(4-chloro-phenyl)-methanone, rac-(4S*,5R*)-2-(4-tert-Butyl-5-chloro-2-ethoxy-phenyl)-4,5-bis-(4-chloro-phenyl)-4,5-dimethyl-4,5-dihydro-1H-imidazole,

[(4S,5R)-2-(4-tert-Butyl-5-chloro-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone, 2-{4-[(4S,5R)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-acetamide, rac-(2-{4-[(4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperazin-1-yl}-1-morpholin-4-yl-ethanone, rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-dimethylamino-piperidin-1-yl)-methanone, rac-[(4S*,5R*)-2-(4-tert-Butyl-5-chloro-2-ethoxy-phenyl)-4,5-bis-(4-chloro-phenyl)-4,5-dimethyl-4,5-dihydro-imidazol-1-yl]-(4-pyrrolidin-1-yl-piperidin-1-yl)-methanone, rac-[1,4']Bipiperidinyl-1'-yl-[(4S*,5R*)-2-(4-tert-butyl-5-chloro-2-ethoxy-phenyl)-4,5-bis-(4-chloro-phenyl)-4,5-dimethyl-4,5-dihydro-imidazol-1-yl]-methanone and rac-{1-[(4S*,5R*)-2-(4-tert-Butyl-5-chloro-2-ethoxy-phenyl)-4,5-bis-(4-chloro-phenyl)-4,5-dimethyl-4,5-dihydro-imidazole-1-carbonyl]-piperidin-4-yl}-carbamic acid tert-butyl ester.

24. A compound of claim 1 selected from the group consisting of

- rac-(4S*,5R*)-4,5-Bis-(4-chloro-phenyl)-2-(2-ethoxy-4-trifluoromethyl-phenyl)-4,5-dimethyl-4,5-dihydro-1H-imidazole,
- rac-4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-2-one,
- rac-1-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-ethanone,
- [(4S,5R)-4,5-Bis-(4-chloro-phenyl)-2-(2-ethoxy-4-trifluoromethyl-phenyl)-4,5-dimethyl-4,5-dihydro-imidazol-1-yl]-[4-(3-methanesulfonyl-propyl)-piperazin-1-yl]-methanone,
- rac-2-{4-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperazin-1-yl}-1-morpholin-4-yl-ethanone,
- rac-(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-ethanesulfonyl-piperazin-1-yl)-methanone,
- rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (1-methanesulfonyl-piperidin-4-yl)-amide,
- rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(4-methyl-piperazin-1-yl)-piperidin-1-yl]-methanone and
- rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-morpholin-4-yl-piperidin-1-yl)-methanone.

25. A compound of claim 1 selected from the group consisting of

- rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxy-piperidin-1-yl)-methanone,
- rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-(4-hydroxymethyl-piperidin-1-yl)-methanone,
- rac-[(4S*,5R*)-4,5-Bis-(4-chloro-phenyl)-2-(2-ethoxy-4-trifluoromethyl-phenyl)-4,5-dimethyl-4,5-dihydro-imidazol-1-yl]-[4-(2-hydroxy-ethyl)-piperidin-1-yl]-methanone,
- rac-1-[(4S*,5R*)-4,5-Bis-(4-chloro-phenyl)-2-(2-ethoxy-4-trifluoromethyl-phenyl)-4,5-dimethyl-4,5-dihydro-imidazole-1-carbonyl]-piperidine-4-carboxylic acid amide,
- rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid bis-(2-hydroxy-ethyl)-amide,
- rac-(4S*,5R*)-4,5-Bis-(4-chloro-phenyl)-2-(2-ethoxy-4-trifluoromethyl-phenyl)-4,5-dimethyl-4,5-dihydro-imidazole-1-carboxylic acid (2,3-dihydroxy-propyl)-amide,
- 3-{4-[4,5-Bis-(4-chloro-phenyl)-4,5-dimethyl-4,5-dihydro-1H-imidazol-2-yl]-3-ethoxy-phenyl}-3-methyl-butan-2-one,
- 3-(4-{4,5-Bis-(4-chloro-phenyl)-1-[4-(3-methanesulfonyl-propyl)-piperazine-1-carbonyl]-4,5-dimethyl-4,5-dihydro-1H-imidazol-2-yl}-3-ethoxy-phenyl)-3-methyl-butan-2-one and
- 3-(4-{(4S,5R)-4,5-Bis-(4-chloro-phenyl)-1-[4-(1,1-dioxo-tetrahydro-2H-thiopyran-4-yl)-piperazine-1-carbonyl]-4,5-dimethyl-4,5-dihydro-1H-imidazol-2-yl}-3-ethoxy-phenyl)-3-methyl-butan-2-one.

26. A compound of claim 1 selected from the group consisting of

- 2-(4-{(4S,5R)-4,5-Bis-(4-chloro-phenyl)-2-[4-(1,1-dimethyl-2-oxo-propyl)-2-ethoxy-phenyl]-4,5-dimethyl-4,5-dihydro-imidazole-1-carbonyl}-piperazin-1-yl)-acetamide,
- rac-(4S*,5R*)-2-(4-tert-Butyl-2-isopropoxy-phenyl)-4,5-bis-(4-chloro-phenyl)-4,5-dimethyl-4,5-dihydro-1H-imidazole,
- rac-1-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-ethanone,
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(4-isopropyl-piperazin-1-yl)-methanone,
- rac-4-{4-[(4S*,5R*)-2-(4-tert-Butyl-2-isopropoxy-phenyl)-4,5-bis-(4-chloro-phenyl)-4,5-dimethyl-4,5-dihydro-imidazole-1-carbonyl]-piperazin-1-yl}-butyronitrile,
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(3-methoxy-propyl)-piperazin-1-yl]-methanone,
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-morpholin-4-yl-ethyl)-piperazin-1-yl]-methanone,
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(tetrahydro-furan-2-ylmethyl)-piperazin-1-yl]-methanone and
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(hexahydro-pyrrolo[1,2-a]pyrazin-2-yl)-methanone.

27. A compound of claim 1 selected from the group consisting of

- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-(octahydro-pyrido[1,2-a]pyrazin-2-yl)-methanone,
- rac-(4S*,5R*)-2-(4-tert-Butyl-2-isopropoxy-phenyl)-4,5-bis-(4-chloro-phenyl)-4,5-dimethyl-4,5-dihydro-imidazole-1-carboxylic acid bis-(2-methoxy-ethyl)-amide,
- rac-[(4S*,5R*)-2-(4-tert-Butyl-2-isopropoxy-phenyl)-4,5-bis-(4-chloro-phenyl)-4,5-dimethyl-4,5-dihydro-imidazol-1-yl]-[4-(2-methoxy-ethyl)-piperazin-1-yl]-methanone,
- [(4S,5R)-2-(4-tert-Butyl-2-isopropoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,
- [(4S,5R)-4,5-Bis-(4-chloro-phenyl)-2-(2-ethoxy-4-isopropyl-phenyl)-4,5-dimethyl-4,5-dihydro-imidazol-1-yl]-[4-(3-methanesulfonyl-propyl)-piperazin-1-yl]-methanone,
- [(4S,5R)-2-(5-tert-Butyl-2-ethoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-5-methanesulfonyl-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-4-methanesulfonyl-phenyl)-4,5-dimethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(4-cyclopropyl-2-ethoxy-phenyl)-4,5-dimethyl-4,5-dihydro-imidazol-1-yl]-[4-(3-methanesulfonyl-propyl)-piperazin-1-yl]-methanone and

[(4S,5R)-4,5-Bis-(4-chloro-phenyl)-2-(5-cyclopropyl-2-ethoxy-phenyl)-4,5-dimethyl-4,5-dihydro-imidazol-1-yl]-[4-(3-methanesulfonyl-propyl)-piperazin-1-yl]-methanone.

28. A compound of claim 1 selected from the group consisting of

[(4S,5R)-4,5-Bis-(4-chloro-phenyl)-2-(4-ethanesulfonyl-2-ethoxy-phenyl)-4,5-dimethyl-4,5-dihydro-imidazol-1-yl]-[4-(3-methanesulfonyl-propyl)-piperazin-1-yl]-methanone,

[(4S,5R)-2-(4-tert-Butyl-2-ethoxy-phenyl)-4,5-bis-(4-chloro-phenyl)-4,5-diethyl-4,5-dihydro-imidazol-1-yl]-[4-(3-methanesulfonyl-propyl)-piperazin-1-yl]-methanone,

[(4S,5R)-4,5-Bis-(4-chloro-phenyl)-2-(2-ethoxy-4-ethylsulfanyl-phenyl)-4,5-dimethyl-4,5-dihydro-imidazol-1-yl]-[4-(3-methanesulfonyl-propyl)-piperazin-1-yl]-methanone,

[(4S,5R)-2-(4-tert-Butyl-2-methoxy-phenyl)-4,5-bis-(4-chloro-phenyl)-4,5-dimethyl-4,5-dihydro-imidazol-1-yl]-[4-(3-methanesulfonyl-propyl)-piperazin-1-yl]-methanone,

[(4S,5R)-2-(4-Chloro-2-ethoxy-5-methanesulfonyl-phenyl)-4,5-bis-(4-chloro-phenyl)-4,5-dimethyl-4,5-dihydro-imidazol-1-yl]-[4-(1,1-dioxo-tetrahydro-2H-thiopyran-4-yl)-piperazin-1-yl]-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(1,1-dioxo-tetrahydro-thiophen-3-yl)-piperazin-1-yl]-methanone,

[(4S,5R)-2-(4-tert-Butyl-2-ethoxy-phenyl)-4,5-bis-(4-chloro-phenyl)-4,5-dimethyl-4,5-dihydro-imidazol-1-yl]-[4-(3-ethanesulfonyl-propyl)-piperazin-1-yl]-methanone, 2-(4-{(4S,5R)-4,5-Bis-(4-chloro-phenyl)-1-[4-(3-ethanesulfonyl-propyl)-piperazine-1-carbonyl]-4,5-dimethyl-4,5-dihydro-1H-imidazol-2-yl}-3-ethoxy-phenyl)-2-methyl-propionitrile, (4S,5R)-2-(4-tert-Butyl-2-ethoxy-phenyl)-4,5-bis-(4-chloro-phenyl)-4-methyl-4,5-dihydro-1H-imidazole.

29. A compound of claim 1 selected from the group consisting of

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone,

[(4S,5R)-2-(4-tert-Butyl-2-ethoxy-phenyl)-4,5-bis-(4-chloro-phenyl)-4-methyl-4,5-dihydro-imidazol-1-yl]-piperazin-1-yl-methanone, 1-[(4S,5R)-2-(4-tert-Butyl-2-ethoxy-phenyl)-4,5-bis-(4-chloro-phenyl)-4-methyl-4,5-dihydro-imidazole-1-carbonyl]-piperidine-4-carboxylic acid amide, 1-{4-[(4S,5R)-2-(4-tert-Butyl-2-ethoxy-phenyl)-4,5-bis-(4-chloro-phenyl)-4-methyl-4,5-dihydro-imidazole-1-carbonyl]-piperazin-1-yl}-ethanone, rac-(4S*,5R*)-2-(4-tert-Butyl-2-ethoxy-phenyl)-4,5-bis-(4-chloro-phenyl)-4-methyl-4,5-dihydro-imidazole-1-carboxylic acid (2-dimethylamino-ethyl)-amide, rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-2-one, rac-2-{4-[(4S,5R)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-morpholin-4-yl-ethanone, rac-[(4S,5R)-2-(4-tert-Butyl-2-ethoxy-phenyl)-4,5-bis-(4-chloro-phenyl)-4-methyl-4,5-dihydro-imidazol-1-yl]-(4-methanesulfonyl-piperazin-1-yl)-methanone, rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-1-pyrrolidin-1-yl-ethanone and rac-[(4S*,5R*)-2-(4-tert-Butyl-2-ethoxy-phenyl)-4,5-bis-(4-chloro-phenyl)-4-methyl-4,5-dihydro-imidazol-1-yl]-[4-(tetrahydro-furan-2-carbonyl)-piperazin-1-yl]-methanone.

30. A compound of claim 1 selected from the group consisting of rac-4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazine-1-carboxylic acid dimethylamide, rac-2-{4-[(4S*,5R*)-2-(4-tert-Butyl-2-ethoxy-phenyl)-4,5-bis-(4-chloro-phenyl)-4-methyl-4,5-dihydro-imidazole-1-carbonyl]-piperazin-1-yl}-acetamide, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-pyrrolidin-1-yl-ethanone, rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-2-one, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-1-morpholin-4-yl-ethanone, rac-[(4S*,5R*)-4,5-Bis-(4-chloro-phenyl)-2-(2-isopropoxy-4-methoxy-phenyl)-4-methyl-4,5-dihydro-imidazol-1-yl]-(4-methanesulfonyl-piperazin-1-yl)-methanone, rac-1-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-ethanone, rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(tetrahydro-furan-2-carbonyl)-piperazin-1-yl]-methanone, rac-2-{4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazin-1-yl}-acetamide and rac-4-[(4S*,5R*)-4,5-Bis-(4-chloro-phenyl)-2-(2-isopropoxy-4-methoxy-phenyl)-4-methyl-4,5-dihydro-imidazole-1-carbonyl]-piperazine-1-carboxylic acid dimethylamide.

31. A compound of claim 1 selected from the group consisting of rac-[(4S*,5R*)-4,5-Bis-(4-chloro-phenyl)-2-(2-isopropoxy-4-methoxy-phenyl)-4-methyl-4,5-dihydro-imidazol-1-yl]-[4-(3-methanesulfonyl-propyl)-piperazin-1-yl]-methanone, rac-[(4S*,5R*)-4,5-Bis-(4-chloro-phenyl)-2-(2-isopropoxy-4-methoxy-phenyl)-4-methyl-4,5-dihydro-imidazol-1-yl]-piperazin-1-yl-methanone, rac-(4S*,5R*)-4,5-Bis-(4-chloro-phenyl)-2-(2-isopropoxy-4-methoxy-phenyl)-4-methyl-4,5-dihydro-imidazole-1-carboxylic acid (2-dimethylamino-ethyl)-amide, rac-1-[(4S*,5R*)-4,5-Bis-(4-chloro-phenyl)-2-(2-isopropoxy-4-methoxy-phenyl)-4-methyl-4,5-dihydro-imidazole-1-carbonyl]-piperidine-4-carboxylic acid amide, rac-4-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperazin-2-one, rac-1-[(4S*,5R*)-2-(4-tert-Butyl-2-ethoxy-phenyl)-4,5-bis-(4-chloro-phenyl)-4-ethyl-4,5-dihydro-imidazole-1-carbonyl]-piperidine-4-carboxylic acid amide, rac-[(4S*,5R*)-4,5-Bis-(4-chloro-phenyl)-4-ethyl-2-(2-isopropoxy-4-methoxy-phenyl)-4,5-dihydro-imidazol-1-yl]-[4-(tetrahydro-furan-2-carbonyl)-piperazin-1-yl]-methanone, rac-2-{4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazin-1-yl}-1-morpholin-4-yl-ethanone and rac-4-[(4S*,5R*)-4,5-Bis-(4-chloro-phenyl)-4-ethyl-2-(2-isopropoxy-4-methoxy-phenyl)-4,5-dihydro-imidazole-1-carbonyl]-piperazine-1-carboxylic acid dimethylamide.

32. A compound of the formula:
(4S,5R)-1-[[4-[[4,5-bis(4-chlorophenyl)-2-[4-(tert-butyl)-2-ethoxy-phenyl]-4,5-dimethyl-4,5-dihydro-1H-imidazol-1-yl]]-carbonyl]-4-[3-(methylsulfonyl)propyl]-piperazine and the pharmaceutically acceptable salts thereof.

33. A pharmaceutical composition comprising a compound of the formula

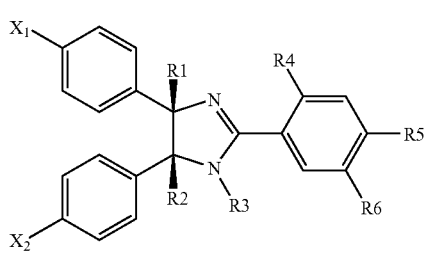

(I)

wherein $X_1$ and $X_2$ are halogen, acetylene, cyano, trifluoromethyl or nitro;

$R^1$ and $R^2$ are selected from the group consisting of H, $CH_3$, $CH_2CH_3$, $CH_2OH$ and $CH_2OCH_3$ with the proviso that $R^1$ and $R^2$ are not both hydrogen;

$R^3$ is H or —C(=O)—$R^7$;

and where $R^6$ is hydrogen then
$R^4$ is —$OCH_3$, —$OCH_2CH_3$, —$OCH_2CH_2F$, —$OCH_2CH_2OCH_3$, or —$OCH(CH_3)_2$;

$R^5$ is
—H
-halogen,
—$CH_3$,
—$CF_3$,
—$OCH_3$,
—$C(CH_3)_2$,
-cyclopropyl,
-cyano,
—$C(CH_3)_3$,
—$C(CH_3)_2$OR (where R is H, $CH_3$ or $CH_2CH_3$),
—$C(CH_3)_2$CH—OR (where R is H, $CH_3$, $CH(CH_3)_2$, $CH_2CH_2OH$ or $CH_2CH_2OCH_3$),
—$C(CH_3)_2$CN,
—$C(CH_3)_2$COR (where R is $CH_3$),
—$C(CH_3)_2$COOR (where R is H, $CH_3$, $CH_2CH_3$ or $CH(CH_3)_2$),
—$C(CH_3)_2$CONR$^a$R$^b$ (where R$^a$ is H or $CH_3$ and R$^b$=H or $CH_3$),
—SR (where R is $CH_3$ or $CH_2CH_3$), or
—$SO_2$R (where R is $CH_3$, $CH_2CH_3$, 1-pyrrolidine, NH-tert-butyl or N($CH_3$)$_2$);

and where $R^6$ is not hydrogen then
$R^4$ is —$OCH_3$, —$OCH_2CH_3$, —$OCH_2CH_2F$, —$OCH_2CH_2OCH_3$, or —$OCH(CH_3)_2$;

$R^5$ is hydrogen, —Cl, —$OCH_3$, tert-butyl or —N($CH_3$)$_2$;

$R^6$ is —Cl, cyclopropyl, —$SO_2$R (where R is $CH_3$, $CH_2CH_3$, 1-pyrrolidine, NH-tert-butyl, $NH_2$, or N($CH_3$)$_2$);

and $R^7$ is selected from the group consisting of
i) —$CH_3$, —$CH(CH_3)_2$, —$CH_2CH(CH_3)_2$, cyclopropyl, cyclobutyl, —$CH_2CH_2$Ph, 2-furanyl, phenyl, or phenyl substituted by chloro, $OCH_3$ or cyano,
ii) 4-morpholinyl, 1-piperidinyl, 4-thiomorpholinyl, or 4-thiomorpholinyl-1,1-dioxide,
iii) —NR$^c_2$ (wherein R$^c$ is hydrogen, —$CH_3$, —$CH_2CH_3$, —$CH_2CH_2OH$, —$CH_2CH_2OCH_3$, or —$CH_2CH(OH)CH_2OH$),
iv) a substituted piperazine of the formula

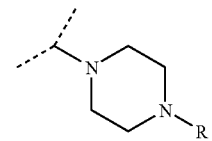

wherein R is selected from the group consisting of
a) hydrogen,
b) lower alkyl,
c) $CH(CH_3)_2$,
d) $CH(CH_2CH_3)_2$,
e) cyclopentyl,
f) —$CH_2CH(OH)CH_3$,
g) —$CH_2CF_3$,
h) —$CH_2CH(OH)CF_3$,
i) —$CH_2C(CH_3)_2OH$,
j) —$CH_2$-[4-N-methylpiperidinyl],
k) —$CH_2CH_2R^d$ (wherein R$^d$ is —OH, —$OCH_3$, —$OCH_2CH_2OH$, —$OCH_2CH_2OCH_3$, —CN, —$CF_3$, —$SO_2CH_3$, —$SO_2NH_2$, —$SO_2N(CH_3)_2$, —$CONH_2$, —$CON(CH_3)_2$, —$NH_2$, —$NHCOCH_3$, —$NHSO_2CH_3$, —$N(CH_3)_2$, —$N(CH_3)_2$, —$N(CH_2CH_3)_2$, 1-pyrrolidinyl, 1-piperidinyl, 4-morpholinyl, 2-isothiazolidinyl-1,1-dioxide, or 2-tetrahydrofuranyl), l) —CH$_2$CH$_2$CH$_2$R$^e$ (wherein R$^e$ is —OH, —OCH$_3$, —SO$_2$CH$_3$, —SO$_2$CH$_2$CH$_3$, —SO$_2$N(CH$_3$)$_2$, —CN, —N(CH$_3$)$_2$, —N(CH$_2$CH$_2$CH$_3$)$_2$, 1-imidazoyl, 1-pyrrolidinyl, 1-piperidinyl, 4-morpholinyl, —COOCH$_3$, —COOCH$_2$CH$_3$, —COOC(CH$_3$)$_3$, —CON(CH$_3$)$_2$, —CO—RF (wherein R$^f$ is CH$_3$, CH$_2$CH$_3$, cyclopropyl, phenyl, 2-thienyl, 3-thienyl, 2-furanyl, 3-furanyl), —COCH$_2$—R$^g$ (wherein R$^g$ is H, —NHCH$_2$CH$_2$OH, —NHCH$_2$CH$_2$OCH$_3$, —NHCH$_2$CH$_2$N(CH$_3$)$_2$, 1-piperidinyl, 1-(piperidinyl-4-methanol), 4-morpholinyl, or —N(CH$_3$)-(3-(1-methylpyrrolidinyl)), m) —CH$_2$—CO—R$^h$ (wherein R$^h$ is —OCH$_3$, OCH$_2$CH$_3$, —NH$_2$, —NHCH$_2$CH(CH$_3$)$_2$, —NHCH$_2$CF$_3$, —NH-cyclopropyl, —NH-tert-butyl, —NHCH$_2$CH$_2$CH$_2$OH, —N(CH$_3$)$_2$, —N(CH$_2$CH$_3$)$_2$, —N(CH$_2$CH$_2$OH)$_2$, —N(CH$_2$CH$_2$OCH$_3$)$_2$, —N(CH$_3$)CH$_2$CH$_2$OH, —N(CH$_3$)CH$_2$CH$_2$OCH$_3$, —NHCH$_2$CH$_2$OCH$_3$, 1-pyrrolidinyl, 1-piperidinyl, 1-(piperidinyl-4-methanol), 1-(piperidinyl-3-carboxamide), 4-morpholinyl, 4-thiomorpholinyl, 4-thiomorpholinyl-1,1-dioxide, 1-piperazinyl, 1-(4-acetylpiperazinyl), 1-(3-oxopiperazinyl), n) —SO$_2$R$^i$ (wherein R$^i$ is —CH$_3$, —CH$_2$CH$_3$, —CH(CH$_3$)$_2$, phenyl, 4-methylphenyl, 4-propylphenyl, CF$_3$, 2-thienyl, 3-thienyl, NH$_2$, NHCH$_3$, N(CH$_3$)$_2$, NHCH$_2$CH$_2$OCH$_3$, N(CH$_2$CH$_2$OCH$_3$)$_2$, 1-pyrrolidinyl, 1-piperidinyl, 4-morpholinyl, 1-piperazyl-4-ethanol, 1-(4-acetylpiperazinyl), 1-(3-oxopiperazinyl)), o) —COR$^j$ (wherein R$^j$ is —CH$_3$, —CH$_2$CH$_3$, —CH(CH$_3$)$_2$, 2-tetrahydrofuranyl, 2-thienyl, 3-thienyl, NH$_2$, NHCH$_3$, N(CH$_3$)$_2$, 1-pyrrolidinyl, 1-piperidinyl, 4-morpholinyl, 1-piperazinyl-4-ethanol, 1-(4-acetylpiperazinyl), or 1-(3-oxopiperazinyl)), p) 4-tetrahydro-2H-thiopyranyl-1,1-dioxide, q) 4-piperidinyl-1-acetyl, r) 4-piperidinyl-1-dimethylcarboxamide, and s) 3-tetrahydro-thiophenyl-1,1-dioxide;

v) a substituted oxopiperazine of the formula

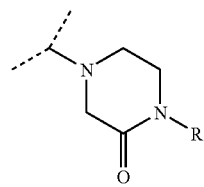

wherein R is H, —CH$_3$, —CH$_2$CH$_3$, —CH$_2$CH$_2$CH$_3$, —CH$_2$CH$_2$OH, or —CH$_2$CH$_2$OCH$_3$ and vi) a substituted piperidine of the formula

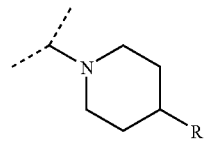

wherein R is H, COOCH$_3$, COOCH$_2$CH$_3$, CONH$_2$, —OH, CH$_2$OH, CH$_2$CH$_2$OH, CH$_2$—N(CH$_2$CH$_3$)$_2$, —CH$_2$-(1-piperazinyl), CH$_2$-(1-(3-oxopiperazinyl)), NH$_2$, NHCOCH$_3$, NHCOCH$_2$NH$_2$, NHCOCH$_2$NHCH$_3$, NHCOCH$_2$N(CH$_3$)$_2$, NHCOCH$_2$N(CH$_2$CH$_2$OH)$_2$, NHCOCH$_2$N(CH$_2$CH$_2$OCH$_3$)$_2$, NHCOCH$_2$NHCH$_2$CH$_2$OH, NHCOCH$_2$-(1-(4-acetylpiperazinyl)), NHCOCH$_2$-(1-(3-oxopiperazinyl)), NHCOCH$_2$-(1-piperidinecarboxamide), NHCOCH$_2$—(N,N-diethyl-1-piperidinylcarboxamide), NHCOCH$_2$-(1-(3-hydroxypiperidinyl)), NHCOCH$_2$-(1-(piperidinyl-4-methanol)), NHCON(CH$_3$)$_2$, NHCSNHCH$_3$, NHCSNHPh, NHCH$_2$CONH$_2$, 1-pyrrolidinyl, 1-piperidinyl, 1-(4-methylpiperazinyl), or 4-morpholinyl;

and the pharmaceutically acceptable salts and esters thereof together with a pharmaceutically acceptable excipient.

* * * * *